United States Patent [19]
Thomas et al.

[11] Patent Number: 6,025,130
[45] Date of Patent: *Feb. 15, 2000

[54] HEREDITARY HEMOCHROMATOSIS GENE

[75] Inventors: Winston J. Thomas; Dennis T. Drayna, both of San Mateo; John N. Feder, Mountain View; Andreas Gnirke, San Carlos; David Ruddy, San Francisco; Zenta Tsuchihashi, Menlo Park; Roger K. Wolff, Belmont, all of Calif.

[73] Assignee: Mercator Genetics, Inc., Menlo Park, Calif.

[ * ] Notice: This patent is subject to a terminal disclaimer.

[21] Appl. No.: 08/652,265

[22] Filed: May 23, 1996

Related U.S. Application Data

[63] Continuation-in-part of application No. 08/632,673, Apr. 6, 1996, which is a continuation-in-part of application No. 08/630,912, Apr. 4, 1996, abandoned.

[51] Int. Cl.[7] .............................. C12Q 1/68; C12P 19/34; C07H 21/04; C12N 15/00
[52] U.S. Cl. ......................... 435/6; 435/91.1; 435/91.2; 536/23.1; 536/23.5; 536/24.31; 536/24.33; 935/1; 935/8; 935/9; 935/76; 935/77
[58] Field of Search .............................. 435/6, 91.1, 91.2, 435/183; 536/23.1, 23.5, 24.31, 24.33; 935/1, 8, 9, 76, 77, 78

[56] References Cited

PUBLICATIONS

Beutler, et al., "A Strategy for Cloning the Hereditary Hemochromatosis Gene," Blood, Cells, Molecules, and Diseases vol. 21, No. 21, pp. 206–216, Nov. 1995.
ATCC/NIH Repository Catalogue of Human and Mouse DNA Probes and Libraries, Eighth Edition, pp. 1–70, 1994.
Barton, J.C. et al., "Hemochromatosis: The genetic disorder of the twenty–first century," Nature Medicine 2(4):394–395 (1996).
Calandro, L.M. et al., "Characterization of a recombinant that locates the hereditary hemochromatosis gene telomeric to HLA–F," Hum. Genet. 96:339–342 (1995).
de Sousa, M. et al., Iron overload in $\beta_2$–microglobulin–deficient mice, Immun. Lett. 39:105:111 (1994).
Dugast, I.J. et al., Identification of Two Human Ferritin H Genes on the Short Arm of Chromosome 6, Genomics 6:204–211 (1990).
Edwards, C.Q. et al., "The locus for hereditary hemochromatosis maps between HLA–A and HLA–B," Cytogenet. Cell Genet. 40:620 (1985).
El Kahloun, A. et al., "Localization of seven new genes around the HLA–A locus," Hum Molec. Genet. 2(1):55–60 (1992).
Gasparini, P. et al., "Linkage analysis of 6p21 polymorphic markers and the hereditary hemochromatosis: locatization of the gene centromeric to HLA–F," Hum. Molec. Genet. 2(5):571–576 (1993).
Gasparini, P. et al., "Where does the gene for hemochromatosis lie in relation to HLA–A," Hematology 19:1050–1056 (1994).
Goei, V.L. et al., "Isolation of Novel Non–HLA Gene Fragments from the Hemochromatosis Region (6p21.3) by cDNA Hybridization Selection," Am. J. Hum. Genet. 54:244–251 (1994).

(List continued on next page.)

Primary Examiner—Bradley L. Sisson
Attorney, Agent, or Firm—Pennie & Edmonds LLP

[57] ABSTRACT

The invention relates generally to the gene, and mutations thereto, that are responsible for the disease hereditary hemochromatosis (HH). More particularly, the invention relates to the identification, isolation, and cloning of the DNA sequence corresponding to the normal and mutant HH genes, as well as the characterization of their transcripts and gene products. The invention also relates to methods and the like for screening for HH homozygotes and further relates to HH diagnosis, prenatal screening and diagnosis, and therapies of HH disease, including gene therapeutics, protein and antibody based therapeutics, and small molecule therapeutics.

67 Claims, 22 Drawing Sheets

OTHER PUBLICATIONS

Gruen, J.R. et al., "Physical and Genetic Mapping of the Telmoeric Major Histocompatibility Complex Region in Man and Relevance to the Primary Hemochromatosis," *Genomics* 14:232–240 (1992).

Gyapay, G. et al., "The 1993–94 Genethon human genetic linkage map," *Nature Genetics* 7:246–339 (1994).

Jazwinska, E.C. et al., "Localization of the Hemochromatosis Gene Close to D6S105," *Am. J. Hum. Genet.* 53:347–352 (1993).

Jazwinska, E.C. et al., "Haplotype Analysis in Australian Hemochromatosis Patients: Evidence for a Predominant Ancestral Haplotype Exclusively Associated with Hemochromatosis," *Am J. Hum. Genet.* 56:428–433 (1995).

Raha–Chowdhury, R. et al., "New polymorphic microsatellite markers place the haemochromatosis gene telomeric to D6S105," *Hum. Mole. Genet.* 4(10):1869–1874 (1995).

Raha–Chowdhury, R. et al., "Allelic associations and homozygosity at loci from HLA–B to D6S299 in genetic haemochromatosis," *J. Med. Genet.* 32:446–452 (1995).

Rothenberg, B.E. et al., "The molecular mechanisms of iron overload: an animal model for hemochromatosis," *FASEB J.* 8. Abstract No. 5217, p. A900 (1994).

Rothenberg, B.E. et al., "$\beta_2$ Knockout mice develop parenchymal iron overload: A putative role for class I genes of the major histocompatibility complex in iron metabolism," *Proc. Natl. Acad. Sci. U.S.A.* 93:1529–1534 (1996).

Stone, C. et al., "Isolation of CA dinucleotide repeats close to D6S105; linkage disequilibrium with haemochromatosis," *Hum Molec.Genet.* 3:2043–2046 (1994).

Summers, K.M. et al., "Fine mapping of a human chromosome 6 ferritin heavy chain pseudogene: relevance to haemochromatosis," *Hum Genet.* 88:175–178 (1991).

Worwood, M. et al., "Alleles at D6S265 and D6S105 define a haemochromatosis–specific genotype," *Brit. J. Hematol.* 86:863–866 (1994).

| PATIENTS | 241-4 | 65-2 | 65-1 | 241-6 | 241-29 | 24d1 | 241-5 | 63-3 | 63-1 | 63-2 | 373-8 |
|---|---|---|---|---|---|---|---|---|---|---|---|
| HC2 | 144 / 144 | 161 / 159 | 208 / 206 | 193 / 205 | 117 / 113 | A / A | 108 / 108 | 169 / 169 | 151 / 151 | 113 / 113 | 151 / 151 |
| HC22 | 144 / 144 | 159 / 161 | 206 / 208 | 205 / 193 | 113 / 117 | A / A | 108 / 108 | 169 / 169 | 151 / 151 | 113 / 113 | 151 / 151 |
| HC25 | 144 / 144 | 167 / 159 | 210 / 206 | 205 / 205 | 113 / 113 | A / A | 108 / 108 | 169 / 169 | 151 / 151 | 113 / 113 | 159 / 151 |
| HC29 | 144 / 144 | 159 / 159 | 206 / 208 | 205 / 205 | 113 / 113 | A / A | 108 / 108 | 169 / 169 | 135 / 151 | 133 / 113 | 155 / 151 |
| HC41 | 144 / 144 | 159 / 159 | 206 / 206 | 205 / 205 | 113 / 113 | A / A | 108 / 108 | 169 / 169 | 151 / 151 | 113 / 113 | 151 / 151 |
| HC50 | 144 / 144 | 161 / 159 | 210 / 206 | 193 / 205 | 119 / 113 | A / A | 108 / 108 | 169 / 169 | 151 / 151 | 113 / 113 | 151 / 151 |
| HC75 | 144 / 144 | 159 / 159 | 206 / 206 | 205 / 205 | 113 / 113 | A / A | 108 / 108 | 167 / 169 | 139 / 151 | 131 / 113 | 153 / 149 |
| HC87 | 144 / 144 | 161 / 159 | 208 / 206 | 193 / 205 | 117 / 113 | A / A | 108 / 108 | 169 / 169 | 151 / 151 | 113 / 113 | 147 / 151 |
| HC91 | 144 / 144 | / 159 | 208 / 206 | 193 / 205 | 117 / 113 | A / A | 108 / 108 | 169 / 169 | 151 / 151 | 113 / 113 | 155 / 149 |
| HC125 | 146 / 144 | 161 / 159 | 210 / 206 | 205 / 205 | 115 / 113 | A / A | 108 / 108 | 169 / 169 | 151 / 151 | 113 / 113 | 153 / 151 |
| HC143 | 146 / 146 | 161 / 159 | 210 / 206 | 193 / 205 | 117 / 113 | A / A | 108 / 108 | 169 / 169 | 151 / 151 | 113 / 113 | 151 / 151 |

MARKERS

FIG.2

```
-360  tctaaggttg  agataaaatt  tttaaatgta  tgattgaatt  ttgaaaatca
-310  taaatattta  aatatctaaa  gttcagatca  gaacattgcg  aagctacttt
-260  ccccaatcaa  caacacccct  tcaggattta  aaaaccaagg  gggacactgg
-210  atcacctagt  gtttcacaag  caggtacctt  ctgctgtagg  agagagagaa
-160  ctaaagttct  gaaagacctg  ttgcttttca  ccaggaagtt  ttactgggca
-110  tctcctgagc  ctaggcaata  gctgtagggt  gacttctgga  gccatcccg
-60   tttcccgcc   ccccaaaaga  agcggagatt  taacggggac  gtgcggccag
-10   agctggggaa
 1    ATGGCCCGC   GAGCCAGGCC  GGCGCTTCTC  CTCCTGATGC  TTTTGCAGAC
 51   CGCGGGTCCTG CAGGGGGCGCT TGCTGCgtga gtccgagggc tgcgggcgaa
101   ctaggggcgc  ggcgggggtg  gaaaaatcga  aactagcttt  ttctttgcgc
151   ttgggagttt  gctaactttg  gaggacctgc  tcaaccctat  ccgcaagccc
201   ctctccctac  tttctgcgtc  cagaccccgt  gaggagtgc   ctaccactga
251   actgcagata  ggggtccctc  gccccaggac  ctgccccctc  cccggctgt
301   cccggctctg  cggagtgact  tttggaaccg  cccactccct  tccccaact
351   agaatgcttt  taaataaatc  tcgtagttcc  tcacttgagc  tgagctaagc
401   ctgggctcc   ttgaacctgg  aactcggtt   tatttccaat  gtcagctgtg
451   cagtttttc   cccagtcatc  tccaaacagg  aagttcttcc  ctgagtgctt
501   gccgagaagg  ctgagcaag   tccaaacagg  atccgcacgg  ggtttccacc
551   tcagaacgaa  tgcgttggc   ggtgggggcg  cgaaagagtg  gcgttgggga
```

FIG. 3A

```
 601 tctgaattct tcaccattcc acccactttt ggtgagacct gggtggagg
 651 tctctaggt gggaggctcc tgagagaggc ctacctcggg cctttcccca
 701 ctcttgcaa ttgttctttt gcctggaaaa ttaagtatat gttagttttg
 751 aacgtttgaa ctgaacaatt ctcttttcgg ctaggcttta ttgattgca
 801 atgtgctgtg taattaagag gcctctctac aaagtactga taatgaacat
 851 gtaagcaatg cactcacttc taagttacat tcatatctga tcttatttga
 901 ttttcactag gcataggag gtaggagcta ataatacgtt tattttacta
 951 gaagttaact ggaattcaga ttatataact ctttttcaggt tacaaagaac
1001 ataaataatc tggttttctg atgttatttc aagtactaca gctgcttcta
1051 atcttagttg acagtgattt tgccctgtag tgtagcacag tgttctgtgg
1101 gtcacacgcc ggcctcagca cagcactttg agtttttggta ctacgtgtat
1151 ccacatttta cacatgacaa gaatgaggcc tggcacggcc tgcttcctgg
1201 caaatttatt caatggtaca ctgggctttg gtggcagagc tcatgtctcc
1251 acttcatagc tatgattctt aaacatcaca ctgcattaga ggttgaataa
1301 taaaatttca acagtgattcag tgtttagcag tgtttacaag tgtaaatgag
1351 tcccagccat gtgtttgcact gttcaagccc caagggagag agcagggaaa
1401 caagtcttta cccttgata ttttgcattc tagtgggaga gatgacaata
1451 agcaaatgag cagaaagata tacaacatca ggaaatcatg ggtgttgtga
1501 gaagcagaga agtcagggca agtcactctg gggctgacac ttgagcagag
1551 acatgaagga aataagaatg atattgactg atattttacaag ttcccaggca
```

FIG. 3B

```
1501 aactgagtgg gcctgcaag ttggattaaa aagcgggttt tctcagcact
1551 actcatgtgt gtgtgtgtgg gtgtctgtag gggggggggg cggcgtgggg gtgggaaggg
1701 ggactaccat ctgcatgtag gatgtctagc agtatcctgt cctccctact
1751 cactaggtgc taggagcact cccccagtct tgacaaccaa aaatgtctct
1801 aaactttgcc acatgtcacc tagtagacaa actcctggtt aagaagctcg 1851 ggttgaaaaa aataaacaag tagtgctggg gagtagaggc caagaagtag
1901 gtaatgggct cagaagagga gccacaaaca aggttgtgca ggcgcctgta
1951 ggctgtggtg tgaattctag ccaaggagta acagtgatct gtcacaggct
2001 tttaaaagat tgctctggct gctatgtgga aagcagaatg aagggagcaa
2051 cagtaaaagc agggagccca gccaggaagc tgttacacag tccaggcaag 2101 aggtagtgga gtgggctggg tgggaacaga aaagggagtg acaaaccatt
2151 gtctcctgaa tatattctga aggaagttgc tgaaggattc tatgttgtgt
2201 gagagaaaga gaagaattgg ctgggtgtag tagctcatgc caaggaggag
2251 gccaaggaga gcagattcct gagctcagga gttcaagacc agcctgggca
2301 acacagcaaa acccctctc tacaaaaaat acaaaaatta gctgggtgtg 2351 gtggcatgca cctgtgatcc tagctactcg ggaggctgag gtggagggta
2401 ttgcttgagc ccaggaagtt gaggctgcag tgagccatga ctgtgccact
2451 gtacttcagc ctaggtgaca gagcaagacc ctgtctcccc tgacccctg
2501 aaaaagagaa gagttaaagt tgacttttgt ttttattttta atttttattgg
2551 cctgagcagt ggggtaattg gcaatgccat ttctgagatg gtgaaggcag
```

FIG. 3C

```
2601  aggaaagagc  agtttggggt  aaatcaagga  tctgcatttg  ggacatgtta
2651  agtttgagat  tccagtcagg  cttccaagtg  gtgaggccac  ataggcagtt
2701  cagtgtaaga  attcaggacc  aaggctgggc  acggtggctc  acttctgtaa
2751  tcccagcact  ttggtggctg  aggcaggtag  atcatttgag  gtcaggagtt
2801  tgagacaagc  ttggccaaca  tggtgaaacc  ccatgtctac  taaaaataca
2851  aaaattagcc  tggtgtggtg  gcgcacgcct  atagtcccag  gtttcagga
2901  ggcttaggta  ggagaatccc  ttgaacccag  gaggtgcagg  ttgcagtgag
2951  ctgagattgt  gccactgcac  tccagcctgg  gtgatagagt  gagactctgt
3001  ctcaaaaaaa  aaaaaaaaaa  aaaaaaaaaa  aactgaagga  attattcctc
3051  aggatttggg  tctaatttgc  cctgagcacc  aactcctgag  ttcaactacc
3101  atggctagac  acacccttaaac  attttctaga  atccaccagc  tttagtggag
3151  tctgtctaat  catgagtatt  ggaataggat  ctggggggcag  tgaggggggtg
3201  gcagccacgt  gtggcagaga  aaagcacaca  aggaaagagc  accaggact
3251  gtcatatgga  agaaagacag  gactgcaact  caccccttcac  aaaatgagga
3301  ccagacacag  ctgatggtat  gagttgatgc  aggtgtgtgg  agcctcaaca
3351  tcctgctccc  ctcctactac  acatggttaa  ggcctgttgc  tctgtctcca
3401  gGTTCACACT  CTCTGCACTA  CCTCTTCATG  GGTGCCTCAG  AGCAGGACCT
3451  TGGTCTTTCC  TTGTTTGAAG  CTTTGGGCTA  CGTGGATGAC  CAGCTGTTCG
                                G         T
3501  TGTTCTATGA  TCATGAGAGT  CGCCGTGTGG  AGCCCCGAAC  TCCATGGTT
3551  TCCAGTAGAA  TTTCAAGCCA  GATGTGGCTG  CAGCTGAGTC  AGAGTCTGAA
```

FIG. 3D

```
3601 AGGGTGGGAT CACACATGTTCA CTGTTGACTT CTGGACTATT ATGGAAAATC
3651 ACAACCACAG CAAGgtatg tgtctttttc gcctcacctt cctgaggttg
3701 tcagagcttt tcatctttc atgcatcttg aaggaaacag ctggaagtct
3751 gaggtcttgt gggagcaggg aagagggaag gaatttgctt cctgagatca
3801 tttggtcctt ggggatggtg gaaataggga cctattcctt tggttgcagt 3851 taacaaggct ggggattttt ccagAGTCCC ACACCCTGCA GGTCATCCTG
3901 GGCTGTGAAA TGCAAGAAGA CAACAGTACC GAGGGCTACT GGAAGTACGG
3951 GTATGATGGG CAGGACCACC TTGAATTCTG CCCTGACACA CTGGATTGGA
4001 GAGCAGCAGA ACCCAGGGCC TGGCCCACCA AGCTGGAGTG GGAAAGGCAC
4051 AAGATTCGGG CCAGGCAGAA CAGGGCCTAC CTGGAGAGGG ACTGCCCTGC 4101 ACAGCTGCAG CAGTTGCTGG AGCTGGGGAG AGGTGTTTTG GACCAACAAG
4151 gtatggtgga aacacactc tgccctata ctctagtggc agagtggagg
4201 aggttgcagg gcacggaatc cctggttgga gtttcagagg tggctgaggc
4251 tgtgtgcctc tccaaattct gggaagggac tttctcaatc ctagagtctc
4301 tacctttata ttgagatgta tgagacagcc acaagtcatg ggttaattt 4351 cttttctcca tgcatatggc tcaaagggaa gtgtctatgg ccctgcttt
4401 ttatttaacc aataatcttt tgtatattta tacctgttaa aaattcagaa
4451 atgtcaaggc cgggcacggt ggctcaccc tgtaatccca gcactttggg
4501 aggccgaggc gggtggtcac aaggtcagga gtttgagacc agcctgacca
4551 acatggtgaa acccgtctct aaaaaatac aaaaattagc tggtcacagt
```

FIG. 3E

```
4601  catgcgcacc  tgtagtccca  gctaattgga  aggctgaggc  aggagcatcg
4651  cttgaacctg  ggaagcggaa  gttgcactga  gccaagatcg  cgccactgca
4701  ctccagccta  ggcagcagag  tgagactcca  tcttaaaaaa  aaaaaaaaaa
4751  aaaaaaagag  aattcagaga  tctcagctat  catatgaata  ccaggacaaa
4801  atatcaagtg  aggccactta  tcagagtaga  agaatccttt  aggttaaaag 4851  tttctttcat  agaacatagc  aataatcact  gaagctacct  atcttacaag
4901  tccgcttctt  ataacaatgc  ctcctaggtt  gacccaggtg  aaactgacca
4951  tctgtattca  atcatttca   atgcacataa  agggcaattt  tatctatcag
5001  aacaagaac   atgggtaaca  gatatgtata  tttacatgtg  aggagaacaa
5051  gctgatctga  ctgctctcca  agtgacactg  tgttagagtc  caatcttagg 5101  acacaaaatg  gtgtctctcc  tgtagcttgt  ttttttctga  aaagggtatt
5151  tccttcctcc  aacctataga  aggaagtgaa  agttccagtc  ttcctgcaa
5201  gggtaaacag  atccccctc   ctcatccttc  ctctttcctg  tcaagTGCCT
5251  CCTTTGGTGA  AGGTGACACA  TCATGTGACC  TCTTCAGTGA  CCACTCTACG
5301  GTGTCGGGCC  TTGAACTACT  ACCCCCAGAA  CATCACCATG  AAGTGGCTGA 5351  AGGATAAGCA  CAGAGATATA  CGTGCCAGGT  GGAGCACCCA  AGACGTATTG
5401  CCCAATGGGG  ATGGGACCTA  CCAGGGCTGG  ATAACCTTGG  CTGTACCCCC
                A 5451  TGGGAAGAG   CAGAGAGT    TGTGATCTGG  GGAGCACCCA  GGCCTGGATC
5501  AGCCCCTCAT  TGTGATCTGG  Ggtatgtgac  tgatgagagc  caggagctga
5551  gaaatctat   tggggttga   gaggagtgcc  tgaggaggta  attatggcag
```

FIG. 3F

```
5601 tgagatgagg atctgctctt tgttagggg tgggctgagg gtggcaatca
5651 aaggctttaa cttgctttt ctgttttagA GCCCTCACCG TCTGGCACCC
5701 TAGTCATTGG AGTCATCAGT GGAATTGCTG TTTTTGTCGT CATCTTGTTC
5751 ATTGGAATTT TGTTCATAAT ATTAAGGAAG AGGCAGGGTT CAAgtgagta
5801 ggaacaaggg ggaagtctct tagtacctct gccccagggc acagtgggaa 5851 gagggcaga ggggatctgg catccatggg aagcattttt ctcatttata
5901 ttcttttgggg acaccagcag ctccctggga gacagaaaat aatgttctc
5951 cccagaatga aagtctctaa ttcaacaaac atcttcagag cacctactat
6001 tttgcaagag ctgtttaagg tagtacaggg gctttgaggt tgagaagtca
6051 ctgtggctat tctcagaacc caaatctggt agggaatgaa attgatagca 6101 agtaaatgta gttaaagaag acccatgag gtcctaaagc aggcaggaag
6151 caaatgctta gggtgtcaaa atcacattca gctgggatc
6201 aagatagcct tctggatctt gaaggagaag ctggattcca ttaggtgagg
6251 ttgaagatga tgggaggtct acacagacgg agcaaccatg ccaagtagga
6301 gagtataagg catactggga gattagaaat aattactgta ccttaaccct 6351 gagtttgcgt agctatcact caccaattat gcatttctac cccctgaaca
6401 tctgtggtgt agggaaaaga gaatcagaaa gaagccagct catacagagt
6451 ccaaggtct tttgggatat tgggttatga tcactgggt gtcattgaag
6501 gatcctaaga aaggaggacc acgatctccc ttatatggtg aatgtgttgt
6551 taagaagtta gatgagaggt gaggagacca gttagaaagc caataagcat
```

FIG. 3G

```
6601 ttccagatga gagataatgg ttccttgaaat ccaatagtgc ccaggtctaa
6651 attgagatgg gtgaatgagg aaaataagga agagagaaga ggcaagatgg
6701 tgcctaggtt tgtgatgcct ctttcctggg tctccttgtct ccacagGAGG
6751 AGCCATGGGG CACTACGTCT TAGCTGAACG TGAGTGAcac gcagcctgca
6801 gactcactgt gggaaggaga caaaactaga gactcaaaga gggagtgcat 6851 ttatgagctc ttcatgtttc aggagagagt tgaacctaaa catagaaatt
6901 gcctgacgaa ctccttgatt ttagccttct ctgttcattt cctcaaaaag
6951 attcccccat ttagtttctc gagttcctgc atgccggtga tccctagctg
7001 tgacctctcc cctgaactg tctctcatga acctcaagct gcatctagag
7051 gcttccttca tttcctccgt cacctcagag acatacacct atgtcatttc 7101 atttcctatt tttggaagag gactccttaa atttggggga cttacatgat
7151 tcattttaac atctgagaaa agctttgaac cctggacgt ggctagtcat
7201 aaccttacca gattttaca catgtatcta tgcatttct ggaccgttc
7251 aactttcct ttgaatcctc tctctgtgtt acccagtaac tcatctgtca
7301 ccaagcctg gggattcttc catctgattg tgatgtgagt tgcacagcta 7351 tgaaggctgt acactgcacg aatggaagag gcacctgtcc cagaaaaagc
7401 atcatggcta tctgtgggta gtatgatggg tgttttagc aggtaggagg
7451 caaatatctt gaaaggggtt gtgaagaggt gttttccta attggcatga
7501 aggtgtcata cagattttgca aagtttaatg gtgccttcat ttgggatgct
7551 actctagtat tccagacctg aagaatcaca ataatttct acctggtctc
```

FIG. 3H

```
7601  tccttgttct  gataatgaaa  attatgataa  ggatgataaa  agcacttact
7651  tcgtgtccga  ctcttctgag  cacctactta  catgcattac  tgcatgcact
7701  tcttacaata  attctatgag  atagtacta   ttatcccat   ttcttttta
7751  aatgaagaaa  gtgaagtagg  ccgggcacgg  tggctcacgc  ctgtaatccc
7801  agcactttgg  gaggccaaag  cgggtggatc  acgaggtcag  gagatcgaga 7851  ccatcctggc  taacatggtg  aaacccatc   tctaataaaa  atacaaaaaa
7901  ttagctgggc  gtggtggcag  acgcctgtag  tcccagctac  tcggaaggct
7951  gaggcaggag  aatggcatga  acccaggagg  cagagcttgc  agtgagccga
8001  gtttgcgcca  ctgcactcca  gcctaggtga  cagagtgaga  ctccatctca
8051  aaaaaataa   aataaaaata  aaaaaaaga   aagtgaagta 8101  tagagtatct  catagtttgt  cagtgataga  aaacagtttc  aaactcagtc
8151  aatctgaccg  tttgatacat  ctcagacacc  actacattca  gtagtttaga
8201  tgcctagaat  aaatagagaa  ggaaggagat  ggctcttctc  ttgtctcatt
8251  gtgttcttc   tgagtgagct  tgaatcacat  gaagggaac   agcagaaaac
8301  aaccaactga  tcctcagctg  tcatgtttcc  tttaaaagtc  cctgaaggaa 8351  ggtcctggaa  tgtgactccc  ttgctcctct  gttgctctct  ttggcattca
8401  ttttcttga   ccctacgcaa  ggactgtaat  tggtggggac  agctagtggc
8451  cctgctgggc  ttcacacacg  gtgtcctccc  taggccagtg  cctctggagt
8501  cagaactctg  gtggtatttc  cctcaatgaa  gtggagtaag  ctctctcatt
8551  ttgagatggt  ataatggaag  ccaccaagtg  gcttagagga  tgcccaggtc
```

FIG. 3I

```
8601 cttccatgga gccactgggg ttccggtgca aaaatctaac
8651 caggacattc aggaattgct agattgct cattaaaaaaa accatgttca
8701 aaagagtctt tttttttt ttgagactct aaatcagttc ctggagtgca
8751 atggcatgat ctcggctcac tgtaacctct attgcccagg ttcaagcgat
8801 tctcctgtct cagcctccca agtagctggg gcctcccagg tgcaccacca 8851 tgcccggcta attttgtat tttagtaga cacagggttt caccatgttg
8901 gccaggctgg tctcgaactc tcctgacctc gtgatccgcc tgcctcggcc
8951 tcccaaagtg ctgagattac aggtgtgagc cacctgcc agccgtcaaa
9001 agagtcttaa tatatatc gagatggcat gtgtttactt tatgttacta
9051 catgcacttg gctgcataaa tgtggtacaa gcattctgtc ttgaagggca 9101 ggtgcttcag gataccatat acagctcaga agtttcttct ttaggcatta
9151 aattttagca aagatatctc atctctttct ttaaaccatt ttcttttttt
9201 gtggttagaa aagttatgta gaaaaaagta aatgtgattt acgctcattg
9251 tagaaaagct ataaaattaa tacaattaaa gctgttattt aattagccag
9301 tgaaaaacta ttaacaactt gtctattacc tgttagtatt attgttgcat 9351 taaaaatgca tatactttaa taaatgtata ttgtattgta tactgcatga
9401 ttttattgaa gttcttgttc atcttgtgta tacttaatt cgctttgtca
9451 ttttggagac atttatttg cttctaattt cttacattt tgtcttacgg
9501 aatattca ttcaactgtg gtagccgaat taatcgtgtt tcttcactct
9551 agggacattg tcgtctaagt tgtaagacat tggttatttt accagcaaac
```

FIG. 3J

```
9601   cattctgaaa  gcatatgaca  aattattcct  ctcttaatat  cttactatac
9651   tgaaagcaga  ctgctataag  gcttcactta  ctcttctacc  tcataaggaa
9701   tatgttacaa  ttaatttatt  aggtaagcat  ttgttttata  ttggttttat
9751   ttcacctggg  ctgagatttc  aagaaacacc  ccagtcttca  cagtaacaca
9801   tttcactaac  acattacta   aacatcagca  actgtggcct  gttaattttt 9851   ttaatagaaa  ttttaagtcc  tcattttctt  tcggtgtttt  ttaagcttaa
9901   tttttctggc  ttattcata   aattcttaag  gtcaactaca  tttgaaaaat
9951   caaagacctg  catttaaat   tcttattcac  ctctggcaaa  accattcaca
10001  aaccatggta  gtaaagagaa  gggtgacacc  tggtggccat  aggtaaatgt
10051  accacggtgg  tccggtgacc  agagatgcag  cgctgagggt  tttcctgaag 10101  gtaaaggaat  aaagaatggg  tggaggggcg  tgcactggaa  atcacttgta
10151  gagaaaagcc  cctgaaaatt  tgagaaaaca  aacaagaaac  tacttaccag
10201  ctatttgaat  tgctggaatc  acaggccatt  gctgagctgc  ctgaactggg
10251  aacacaacag  aaggaaaaca  aggaaaaaca  atatcattg   agtcaagtac
10301  agcaggtgat  tgaggactgc  tgagaggtac  aggccaaaat  tcttatgttg 10351  tattataata  atgtcatctt  ataatactgt  cagtatttta  taaaacattc
10401  ttcacaaact  cacacacatt  taaaaacaaa  acactgtctc  taaaatcccc
10451  aaattttca   taaac
```

FIG. 3K

```
gggacactg gatcacctag tgtttcacaa gcaggtacct tctgctgtag gagagagaga
actaagttc tgaaagacct gttgctttc accaggaagt tttactggc atctcctgag
cctaggcaat agctgtaggg tgacttctgg agccatcccc gtttcccgc cccccaaaag
aagcggagat ttaacgggga cgtgcggcca gagctggggga a
                                              atgggcccg cgagccaggc
                                              M  G  P    R  A  R cggcgcttct cctcctgatg cttttgcaga ccgcgtcct gcaggggcgc ttgctgcgtt
P  A  L  L    L  L  M   L  L  Q     T  A  V  L    Q  G  R    L  L  R cacactctct gcactacctc ttcatgggtg cctcagagca ggaccttggt ctttccttgt
S  H  S  L    H  Y  L    F  M  G    A  S  E  Q    D  L  G    L  S  L
                                                   24d2G         T 24d7
ttgaagcttt gggctacgtg gatgaccagc tgttcgtgtt ctatgatcat gagagtcgcc
F  E  A  L    G  Y  V    D  D  Q    L  F  V  F    Y  D  H    E  S  R
                                                   24d2           C gtgtggagcc ccgaactcca tgggtttcca gtagaattc aagccagatg tggctgcagc
R  V  E  P    R  T  P    W  V  S    S  R  I  S    S  Q  M    W  L  Q tgagtcagag tctgaaaggg tgggatcaca tgttcactgt tgacttctgg actattatgg
L  S  Q  S    L  K  G    W  D  H    M  F  T  V    D  F  W    T  I  M
```

FIG. 4A

```
aaaatcacaa  ccacagcaag  gagtcccaca  ccctgcaggt  catcctgggc  tgtgaaatgc
 E  N  H  N  H  S  K     E  S  H     T  L  Q  V  I  L  G     C  E  M aagaagacaa  cagtaccgag  ggctactgga  agtacgggta  tgatgggcag  gaccacttg
 Q  E  D     S  T  E     G  Y  W     K  Y  G  Y  D  G  Q    D  H  L aattctgccc  tgacacactg  gattggagag  cagcagaaac  cagggcctgg  cccaccaagc
 E  F  C  P  D  T  L     D  W  R     A  A  E  P  R  A  W     P  T  K tggagtggga  aaggcacaag  attcgggcca  ggcagaacag  ggcctacctg  gagaggact
 L  E  W  E  R  H  K     I  R  A     R  Q  N  R  A  Y  L     E  R  D gccctgcaca  gctgcagcag  ttgctggagc  tggggagagg  tgttttggac  caacaagtgc
 C  P  A  Q  L  Q  Q     L  L  E     L  G  R  G  V  L  D     Q  Q  V ctccttttgt  gaaggtgaca  catcatgtga  cctcttcagt  gaccactcta  cggtgtcggg
 P  P  L  V  K  V  T     H  H  V     T  S  S  V  T  T  L     R  C  R ccttgaacta  ctaccccag   aacatcacca  tgaagtggct  gaaggataag  cagccaatgg
 A  L  N  Y  Y  P  Q     N  I  T     M  K  W  L  K  D  K     Q  P  M atgccaagga  gttcgaacct  aaagacgtat  tgcccaatgg  ggatgggacc  taccagggct
 D  A  K  E  F  E  P     K  D  V     L  P  N  G  D  G  T     Y  Q  G
```

FIG. 4B

```
ggataacctt ggctgtaccc cctggggaag agcagagata tacg|A|24d1|gtggagcacc
W  I  T  L  A  V  P    P  G  E    E  Q  R  Y    T  C  Q    V  E  H
                                                  Y
caggcctgga tcagcccctc attgtgatct gggagccctc accgtctggc accctagtca
P  G  L  D  Q  P  L    I  V  I    W  E  P  S    P  P  S  G  T  L  V ttggagtcat cagtggaatt gctgtttttg tcgtcatctt gttcattgga atttgttca
I  G  V  I  S  G  I    A  V  F    V  V  I  L    F  I  G    I  L  F taatattaag gaagaggcag ggttcaagag gagccatggg gcactacgtc ttagctgaac
I  I  L  R  K  R  Q    G  S  R    G  A  M  G    H  Y  V    L  A  E gtgagtga
R  E  * ca cgcagcctgc agactcactg tgggaaggag acaaaactag agactcaaag
agggagtgca tttatgagct cttcatgttt caggagagag ttgaacctaa acatagaaat
tgcctgacga actccttgat tttagccttc tctgttcatt tcctcaaaaa gatttcccca
```

FIG.4C

PCR Primers used for Amplification Of 24d1 Alleles

24d1.P1   (forward primer)
   5'-TGGCAAGGGTAAACAGATCC-3'   (SEQ ID NO:13)

24d1.P2   (reverse primer)
   5'-CTCAGGCACTCCTCTCAACC-3'   (SEQ ID NO:14)

OLA Oligonucleotides for 24d1

Upstream Oligonucleotides (5'-biotinylated)

24d1.A   (common allele)
   5'-bio-GGAAGAGCAGAGATATACGTG-3'   (SEQ ID NO:15)

24d1.B   (hemochromatosis allele)
   5'-bio-GGAAGAGCAGAGATATACGTA-3'   (SEQ ID NO:16)

Downstream Oligonucleotides (5'-phosphorylated)

24d1.X   5'-p-CCAGGTGGGAGCACCCAGG-dig-3'
   (SEQ ID NO:17)

FIG. 5

5'-TATTCCTTCCTCCAACCTATAGAAGGAAGTGAAAGTTCCAGTCTTCCTGGCAAGGGTAAACAGATCCCC
<u>TCTCCTCATCCTTCCTCTCTTCCTGTCAAGTGCCTCTCCTTGGTGAAGGTGACACATCATGTGACCTCTTCAG</u>
<u>24d1.P1</u>
TGACCACTCTACGGTGTCGGGCCTTGAACTACTACCCCCAGAACATCACCATGAAGTGGCTGAAGGATA
AGCAGCCAATGGATGCCAAGGAGTTCGAACCTAAAGACGTATTGCCCAATGGGGATGGGGACCTACCAGG
GCTGGATAACCTTGGCTGTACCCCCTGGGGAAGAGCAGAGATATACGTGCCAGGTGGGAGCACCCAGGC
CTGGATCAGCCCCTCATTGTGATCTGGGTATGTGACTGATGAGAGCCAGGAGCTGAGAAAATCTATTGG
<u>GGGTTGAGAGGAGTGCCTGAGGAGGAGGTAATTATGGCAGTGAGAGGATCTGCTCTTTGTAGGGGGTG</u>
<u>24d1.P2</u>
GGCTGAGGGTGGCAATCAAAGGCTTTAACTT-3'

(SEQ ID NO:20)

FIG. 6A

5'-TATTTCCTTCCTCCAACCTATAGAAGGAAGTGAAAGTTCCAGTCTTCCTGGCAAGGGTAAACAGATCCCC
                                                               24d1.P1
TCTCCTCATCCTTCCTCTCTTCCTGTCAAGTGCCTCCTTGGTGAAGGTGACACATCATGTGACCTCTTCAG
TGACCACTCTACGGTGTCGGGCCCTGAACTACTACCCCCAGAACATCACCATGAAGTGGCTGAAGGATA
AGCAGCCAATGGATGCCAAGGAGTTCGAACCTAAAGACGTATTGCCCAATGGGGATGGGACCTACCAGG
GCTGGATAACCTTGGCTGTACCCCCTGGGAAGAGCAGAGATATACGTACCAGGTGGAGCACCCAGGC
CTGGATCAGCCCCTCATTGTGATCTGGGTATGTGACTGATGAGAGCCAGGAGCTGAGAAAATCTATTGG
GGGTTGAGAGGAGTGCCTGAGGAGGAGTAATTATGCCAGTGAGATGAGGATCTGCTCTTGTTAGGGGGTG
   24d1.P2
GGCTGAGGGTGGCAATCAAAGGCTTTAACTT-3'                    (SEQ ID NO:21)

FIG. 6B

```
HH Protein    MGPRARPALLLMLLQTAVLQGRLLRSHSLHYLFMGASEQDLGLSLFEALGYVDDQLFVF
RLA          -MGSIPPRTLLLLAGALTLKDTQAGSHSMRYFYTSVSRPGLGEPRFIIVGYVDDTQFVR
hMHC         -MAVMAPRTLVLLLSGALALTQTWAGSHSMRYFFTSVSRPGRGEPRFIAVGYVDDTQFVR HH Protein    YDHE--SRRVEPRTPWSSRISSQMWLQLSQSLKGWDHMFTVDFWTIMENHNHS-KESHT
RLA          FDSDAASPRMEQRAPWMG-QVEPEYWDQQTQIAKDTAQTFRVNLNTALRYYNQSAAGSHT
hMHC         FDSDAASQRMEPRAPWIE-QEGPEYWDGETRKVKAHSQTHRVDLGTLRGYYNQSEAGSHT HH Protein    LQVILGCEMQEDN-STEGYWKYGYDGQDHLEFCPDTLDWRAAEPRAWPTKLEWERHKIRA
RLA          FQTMFGCEVWADGRFFHGYRQYAYDGADYIALNEDLRSWTAADTAAQNTQRKWEAAGEAE
hMHC         LQMMFGCDVGSDWRFLRGYHQYAYDGKDYIALKEDLRSWTAADMAAQTKHKWEAAHVAE HH Protein    RQNRAYLERDCPAQLQQLLELGRGVLDQQVPPLVKVTHHVTSIS-VTTLRCRALNYYPQNI
RLA          R-HRAYLERECVEWLRRYLEMGKETLQRADPPKAHVTHHPASDREATLRCWALGFYPAEI
hMHC         Q-LRAYLEGTCVEWLRRYLENGKETLQRTDAPKTHMTHHAVSDHEATLRCWALSFYPAEI HH Protein    TMKWLKD--KQPMDAKEFEPKDVLPNGDGTYQGWITLAVPPGEEQRYTCQVEHPGLDQPL
RLA          SLTWQRDGEDQTQDTELVETR---PGGDGTFQKWAAVVVPSGEEQRYTCRVQHEGLPEPL
hMHC         TLTWQRDGEDQTQDTELVETR---PAGDGTFQKWAAVVVPSGQEQRYTCHVQHEGLPKPL HH Protein    IVIWEPSPS-GTLVIGVISGIAVFVILFIGILFILRKRQGSRGAMGHYVLAER-----
RLA          TLTWEPPAQPTALIVGIVAG-VLGVLLLILGAVVAVVRRKKHSSDGKGGRYTPAAGGHRDQ
hMHC         TLRWEPSSQPTIPIVGIIAGLVLFGAVITGAVVAAVMWRRKSSDRKGGSYSQAASSDSAQ HH Protein    ---------
RLA          GSDDSLMP---
hMHC         GSDVSLTACKV
```

FIG. 7

PCR Primers used for Amplification Of 24d2 Alleles

24.P2.1 (forward primer)
5'-ACATGGTTAAGGCCTGTTGC-3' (SEQ ID NO:24)

24.P2.2 (reverse primer)
5'-GCCACATCTGGCTTGAAATT-3' (SEQ ID NO:25)

OLA Oligonucleotides for 24d2
Upstream Oligonucleotides (5'-biotinylated)

24d2.A (common allele)
5'-bio-AGCTGTTCGTGTTCTATGATC-3' (SEQ ID NO:26)

24d2.B (hemochromatosis allele)
5'-bio-AGCTGTTCGTGTTCTATGATG-3' (SEQ ID NO:27)

Downstream Oligonucleotides (5'-phosphorylated)
24d2.X 5'-p-ATGAGAGTCGGCCGTGTGGA-dig-3' (SEQ ID NO:28)

FIG. 9

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
        (A) LENGTH: 10825 base pairs
        (B) TYPE: nucleic acid
        (C) STRANDEDNESS: single

```
        (D) TOPOLOGY: linear (ii) MOLECULE TYPE: DNA (genomic)

(ix) FEATURE:
        (A) NAME/KEY: CDS
        (B) LOCATION: join(361..436, 3762..4025, 4235..4510, 5606..
            5881, 6040..6153, 7107..7147)
        (D) OTHER INFORMATION: /product= "Hereditary Hemochromatosis
    (HH) protein"
            /note= "Normal or wild-type (unaffected)
            Hereditary Hemochromatosis (HH) gene
            allele"

(ix) FEATURE:
        (A) NAME/KEY: -
        (B) LOCATION: 140..7319
        (D) OTHER INFORMATION: /note= "start and stop positions for
            normal or wild-type (unaffected) allele
            cDNA (SEQ ID NO:9)"

(ix) FEATURE:
        (A) NAME/KEY: -
        (B) LOCATION: 3852..3891
        (D) OTHER INFORMATION: /note= "start and stop positions for
            normal or wild-type (unaffected) genomic
            sequence surrounding variant for 24d2(C)
            allele (SEQ ID NO:41)"

(ix) FEATURE:
        (A) NAME/KEY: -
        (B) LOCATION: 5507..6023
        (D) OTHER INFORMATION: /note= "start and stop positions for
            normal or wild-type (unaffected) genomic
            sequence surrounding variant for 24d1(G)
            allele (SEQ ID NO:20)"

(ix) FEATURE:
        (A) NAME/KEY: allele
        (B) LOCATION: replace(3872, "c")
        (D) OTHER INFORMATION: /phenotype= "normal or wild-type
            (unaffected)"
            /label= 24d2

(ix) FEATURE:
        (A) NAME/KEY: allele
        (B) LOCATION: replace(3878, "a")
        (D) OTHER INFORMATION: /phenotype= "normal or wild-type
            (unaffected)"
            /label= 24d7

(ix) FEATURE:
        (A) NAME/KEY: allele
        (B) LOCATION: replace(5834, "g")
        (D) OTHER INFORMATION: /phenotype= "normal or wild-type
            (unaffected)"
            /label= 24d1

(xi) SEQUENCE DESCRIPTION: SEQ ID NO:1:

TCTAAGGTTG AGATAAAATT TTTAAATGTA TGATTGAATT TTGAAAATCA TAAATATTTA      60

AATATCTAAA GTTCAGATCA GAACATTGCG AAGCTACTTT CCCCAATCAA CAACACCCCT    120

TCAGGATTTA AAAACCAAGG GGGACACTGG ATCACCTAGT GTTTCACAAG CAGGTACCTT    180

CTGCTGTAGG AGAGAGAGAA CTAAAGTTCT GAAAGACCTG TTGCTTTTCA CCAGGAAGTT    240

TTACTGGGCA TCTCCTGAGC CTAGGCAATA GCTGTAGGGT GACTTCTGGA GCCATCCCCG    300

TTTCCCCGCC CCCAAAAGA AGCGGAGATT TAACGGGGAC GTGCGGCCAG AGCTGGGGAA     360

ATG GGC CCG CGA GCC AGG CCG GCG CTT CTC CTC CTG ATG CTT TTG CAG      408
Met Gly Pro Arg Ala Arg Pro Ala Leu Leu Leu Leu Met Leu Leu Gln
 1               5                  10                  15

ACC GCG GTC CTG CAG GGG CGC TTG CTG C GTGAGTCCGA GGGCTGCGGG          456
Thr Ala Val Leu Gln Gly Arg Leu Leu
        20                  25
```

-continued

```
CGAACTAGGG GCGCGGCGGG GGTGGAAAAA TCGAAACTAG CTTTTTCTTT GCGCTTGGGA      516

GTTTGCTAAC TTTGGAGGAC CTGCTCAACC CTATCCGCAA GCCCCTCTCC CTACTTTCTG      576

CGTCCAGACC CCGTGAGGGA GTGCCTACCA CTGAACTGCA GATAGGGGTC CCTCGCCCCA      636

GGACCTGCCC CCTCCCCCGG CTGTCCCGGC TCTGCGGAGT GACTTTTGGA ACCGCCCACT      696

CCCTTCCCCC AACTAGAATG CTTTTAAATA AATCTCGTAG TTCCTCACTT GAGCTGAGCT      756

AAGCCTGGGG CTCCTTGAAC CTGGAACTCG GGTTTATTTC CAATGTCAGC TGTGCAGTTT      816

TTTCCCCAGT CATCTCCAAA CAGGAAGTTC TTCCCTGAGT GCTTGCCGAG AAGGCTGAGC      876

AAACCCACAG CAGGATCCGC ACGGGGTTTC CACCTCAGAA CGAATGCGTT GGGCGGTGGG      936

GGCGCGAAAG AGTGGCGTTG GGGATCTGAA TTCTTCACCA TTCCACCCAC TTTTGGTGAG      996

ACCTGGGGTG GAGGTCTCTA GGGTGGGAGG CTCCTGAGAG AGGCCTACCT CGGGCCTTTC     1056

CCCACTCTTG GCAATTGTTC TTTTGCCTGG AAAATTAAGT ATATGTTAGT TTGAACGTT      1116

TGAACTGAAC AATTCTCTTT TCGGCTAGGC TTTATTGATT TGCAATGTGC TGTGTAATTA     1176

AGAGGCCTCT CTACAAAGTA CTGATAATGA ACATGTAAGC AATGCACTCA CTTCTAAGTT     1236

ACATTCATAT CTGATCTTAT TTGATTTTCA CTAGGCATAG GGAGGTAGGA GCTAATAATA     1296

CGTTTATTTT ACTAGAAGTT AACTGGAATT CAGATTATAT AACTCTTTTC AGGTTACAAA     1356

GAACATAAAT AATCTGGTTT TCTGATGTTA TTTCAAGTAC TACAGCTGCT TCTAATCTTA     1416

GTTGACAGTG ATTTTGCCCT GTAGTGTAGC ACAGTGTTCT GTGGGTCACA CGCCGGCCTC     1476

AGCACAGCAC TTTGAGTTTT GGTACTACGT GTATCCACAT TTTACACATG ACAAGAATGA     1536

GGCATGGCAC GGCCTGCTTC CTGGCAAATT TATTCAATGG TACACTGGGC TTTGGTGGCA     1596

GAGCTCATGT CTCCACTTCA TAGCTATGAT TCTTAAACAT CACACTGCAT TAGAGGTTGA     1656

ATAATAAAAT TTCATGTTGA GCAGAAATAT TCATTGTTTA CAAGTGTAAA TGAGTCCCAG     1716

CCATGTGTTG CACTGTTCAA GCCCCAAGGG AGAGAGCAGG GAAACAAGTC TTTACCCTTT     1776

GATATTTTGC ATTCTAGTGG GAGAGATGAC AATAAGCAAA TGAGCAGAAA GATATACAAC     1836

ATCAGGAAAT CATGGGTGTT GTGAGAAGCA GAGAAGTCAG GGCAAGTCAC TCTGGGGCTG     1896

ACACTTGAGC AGAGACATGA AGGAAATAAG AATGATATTG ACTGGGAGCA GTATTTCCCA     1956

GGCAAACTGA GTGGGCCTGG CAAGTTGGAT TAAAAAGCGG GTTTTCTCAG CACTACTCAT     2016

GTGTGTGTGT GTGGGGGGGG GGGCGGCGT GGGGGTGGGA AGGGGACTA CCATCTGCAT       2076

GTAGGATGTC TAGCAGTATC CTGTCCTCCC TACTCACTAG GTGCTAGGAG CACTCCCCCA     2136

GTCTTGACAA CCAAAAATGT CTCTAAACTT TGCCACATGT CACCTAGTAG ACAAACTCCT     2196

GGTTAAGAAG CTCGGGTTGA AAAAAATAAA CAAGTAGTGC TGGGGAGTAG AGGCCAAGAA     2256

GTAGGTAATG GGCTCAGAAG AGGAGCCACA AACAAGGTTG TGCAGGCGCC TGTAGGCTGT     2316

GGTGTGAATT CTAGCCAAGG AGTAACAGTG ATCTGTCACA GGCTTTTAAA AGATTGCTCT     2376

GGCTGCTATG TGGAAAGCAG AATGAAGGGA GCAACAGTAA AAGCAGGGAG CCCAGCCAGG     2436

AAGCTGTTAC ACAGTCCAGG CAAGAGGTAG TGGAGTGGGC TGGGTGGGAA CAGAAAAGGG     2496

AGTGACAAAC CATTGTCTCC TGAATATATT CTGAAGGAAG TTGCTGAAGG ATTCTATGTT     2556

GTGTGAGAGA AAGAGAAGAA TTGGCTGGGT GTAGTAGCTC ATGCCAAGGA GGAGGCCAAG     2616

GAGAGCAGAT TCCTGAGCTC AGGAGTTCAA GACCAGCCTG GGCAACACAG CAAAACCCCT     2676

TCTCTACAAA AAATACAAAA ATTAGCTGGG TGTGGTGGCA TGCACCTGTG ATCCTAGCTA     2736

CTCGGGAGGC TGAGGTGGAG GGTATTGCTT GAGCCCAGGA AGTTGAGGCT GCAGTGAGCC     2796
```

```
ATGACTGTGC CACTGTACTT CAGCCTAGGT GACAGAGCAA GACCCTGTCT CCCCTGACCC    2856

CCTGAAAAAG AGAAGAGTTA AAGTTGACTT TGTTCTTTAT TTTAATTTTA TTGGCCTGAG    2916

CAGTGGGGTA ATTGGCAATG CCATTTCTGA GATGGTGAAG GCAGAGGAAA GAGCAGTTTG    2976

GGGTAAATCA AGGATCTGCA TTTGGGACAT GTTAAGTTTG AGATTCCAGT CAGGCTTCCA    3036

AGTGGTGAGG CCACATAGGC AGTTCAGTGT AAGAATTCAG GACCAAGGCT GGGCACGGTG    3096

GCTCACTTCT GTAATCCCAG CACTTTGGTG GCTGAGGCAG GTAGATCATT TGAGGTCAGG    3156

AGTTTGAGAC AAGCTTGGCC AACATGGTGA AACCCCATGT CTACTAAAAA TACAAAAATT    3216

AGCCTGGTGT GGTGGCGCAC GCCTATAGTC CCAGGTTTTC AGGAGGCTTA GGTAGGAGAA    3276

TCCCTTGAAC CCAGGAGGTG CAGGTTGCAG TGAGCTGAGA TTGTGCCACT GCACTCCAGC    3336

CTGGGTGATA GAGTGAGACT CTGTCTCAAA AAAAAAAAAA AAAAAAAAA AAAAAACTGA    3396

AGGAATTATT CCTCAGGATT TGGGTCTAAT TTGCCCTGAG CACCAACTCC TGAGTTCAAC    3456

TACCATGGCT AGACACACCT AACATTTTC TAGAATCCAC CAGCTTTAGT GGAGTCTGTC    3516

TAATCATGAG TATTGGAATA GGATCTGGGG GCAGTGAGGG GGTGGCAGCC ACGTGTGGCA    3576

GAGAAAAGCA CACAAGGAAA GAGCACCCAG GACTGTCATA TGGAAGAAAG ACAGGACTGC    3636

AACTCACCCT TCACAAAATG AGGACCAGAC ACAGCTGATG GTATGAGTTG ATGCAGGTGT    3696

GTGGAGCCTC AACATCCTGC TCCCCTCCTA CTACACATGG TTAAGGCCTG TTGCTCTGTC    3756

TCCAG   GT TCA CAC TCT CTG CAC TAC CTC TTC ATG GGT GCC TCA GAG       3802
        Arg Ser His Ser Leu His Tyr Leu Phe Met Gly Ala Ser Glu
                          30                  35

CAG GAC CTT GGT CTT TCC TTG TTT GAA GCT TTG GGC TAC GTG GAT GAC      3850
Gln Asp Leu Gly Leu Ser Leu Phe Glu Ala Leu Gly Tyr Val Asp Asp
 40              45                  50                  55

CAG CTG TTC GTG TTC TAT GAT CAT GAG AGT CGC CGT GTG GAG CCC CGA      3898
Gln Leu Phe Val Phe Tyr Asp His Glu Ser Arg Arg Val Glu Pro Arg
                 60                  65                  70

ACT CCA TGG GTT TCC AGT AGA ATT TCA AGC CAG ATG TGG CTG CAG CTG      3946
Thr Pro Trp Val Ser Ser Arg Ile Ser Ser Gln Met Trp Leu Gln Leu
             75                  80                  85

AGT CAG AGT CTG AAA GGG TGG GAT CAC ATG TTC ACT GTT GAC TTC TGG      3994
Ser Gln Ser Leu Lys Gly Trp Asp His Met Phe Thr Val Asp Phe Trp
         90                  95                 100

ACT ATT ATG GAA AAT CAC AAC CAC AGC AAG G GTATGTGGAG AGGGGGCCTC      4045
Thr Ile Met Glu Asn His Asn His Ser Lys
    105                 110

ACCTTCCTGA GGTTGTCAGA GCTTTTCATC TTTTCATGCA TCTTGAAGGA AACAGCTGGA    4105

AGTCTGAGGT CTTGTGGGAG CAGGGAAGAG GGAAGGAATT TGCTTCCTGA GATCATTTGG    4165

TCCTTGGGGA TGGTGGAAAT AGGGACCTAT TCCTTTGGTT GCAGTTAACA AGGCTGGGGA    4225

TTTTTCCAG  AG TCC CAC ACC CTG CAG GTC ATC CTG GGC TGT GAA ATG        4272
           Glu Ser His Thr Leu Gln Val Ile Leu Gly Cys Glu Met
                   115                 120                 125

CAA GAA GAC AAC AGT ACC GAG GGC TAC TGG AAG TAC GGG TAT GAT GGG      4320
Gln Glu Asp Asn Ser Thr Glu Gly Tyr Trp Lys Tyr Gly Tyr Asp Gly
             130                 135                 140

CAG GAC CAC CTT GAA TTC TGC CCT GAC ACA CTG GAT TGG AGA GCA GCA      4368
Gln Asp His Leu Glu Phe Cys Pro Asp Thr Leu Asp Trp Arg Ala Ala
         145                 150                 155

GAA CCC AGG GCC TGG CCC ACC AAG CTG GAG TGG GAA AGG CAC AAG ATT      4416
Glu Pro Arg Ala Trp Pro Thr Lys Leu Glu Trp Glu Arg His Lys Ile
     160                 165                 170

CGG GCC AGG CAG AAC AGG GCC TAC CTG GAG AGG GAC TGC CCT GCA CAG      4464
```

```
Arg Ala Arg Gln Asn Arg Ala Tyr Leu Glu Arg Asp Cys Pro Ala Gln
175                 180                 185                 190

CTG CAG CAG TTG CTG GAG CTG GGG AGA GGT GTT TTG GAC CAA CAA G          4510
Leu Gln Gln Leu Leu Glu Leu Gly Arg Gly Val Leu Asp Gln Gln
                195                 200                 205

GTATGGTGGA AACACACTTC TGCCCCTATA CTCTAGTGGC AGAGTGGAGG AGGTTGCAGG      4570

GCACGGAATC CCTGGTTGGA GTTTCAGAGG TGGCTGAGGC TGTGTGCCTC TCCAAATTCT      4630

GGGAAGGGAC TTTCTCAATC CTAGAGTCTC TACCTTATAA TTGAGATGTA TGAGACAGCC      4690

ACAAGTCATG GGTTTAATTT CTTTTCTCCA TGCATATGGC TCAAAGGGAA GTGTCTATGG      4750

CCCTTGCTTT TTATTTAACC AATAATCTTT TGTATATTTA TACCTGTTAA AAATTCAGAA      4810

ATGTCAAGGC CGGGCACGGT GGCTCACCCC TGTAATCCCA GCACTTTGGG AGGCCGAGGC      4870

GGGTGGTCAC AAGGTCAGGA GTTTGAGACC AGCCTGACCA ACATGGTGAA ACCCGTCTCT      4930

AAAAAAATAC AAAAATTAGC TGGTCACAGT CATGCGCACC TGTAGTCCCA GCTAATTGGA      4990

AGGCTGAGGC AGGAGCATCG CTTGAACCTG GAAGCGGAA GTTGCACTGA GCCAAGATCG      5050

CGCCACTGCA CTCCAGCCTA GGCAGCGAG TGAGACTCCA TCTTAAAAAA AAAAAAAAA       5110

AAAAAAGAG AATTCAGAGA TCTCAGCTAT CATATGAATA CCAGGACAAA ATATCAAGTG       5170

AGGCCACTTA TCAGAGTAGA AGAATCCTTT AGGTTAAAAG TTTCTTTCAT AGAACATAGC     5230

AATAATCACT GAAGCTACCT ATCTTACAAG TCCGCTTCTT ATAACAATGC CTCCTAGGTT     5290

GACCCAGGTG AAACTGACCA TCTGTATTCA ATCATTTTCA ATGCACATAA AGGGCAATTT     5350

TATCTATCAG AACAAAGAAC ATGGGTAACA GATATGTATA TTTACATGTG AGGAGAACAA     5410

GCTGATCTGA CTGCTCTCCA AGTGACACTG TGTTAGAGTC CAATCTTAGG ACACAAAATG     5470

GTGTCTCTCC TGTAGCTTGT TTTTTTCTGA AAAGGGTATT TCCTTCCTCC AACCTATAGA     5530

AGGAAGTGAA AGTTCCAGTC TTCCTGGCAA GGGTAAACAG ATCCCCTCTC CTCATCCTTC     5590

CTCTTTCCTG TCAAG  TG CCT CCT TTG GTG AAG GTG ACA CAT CAT GTG ACC      5640
                Val Pro Pro Leu Val Lys Val Thr His His Val Thr
                            210                 215

TCT TCA GTG ACC ACT CTA CGG TGT CGG GCC TTG AAC TAC TAC CCC CAG       5688
Ser Ser Val Thr Thr Leu Arg Cys Arg Ala Leu Asn Tyr Tyr Pro Gln
        220                 225                 230

AAC ATC ACC ATG AAG TGG CTG AAG GAT AAG CAG CCA ATG GAT GCC AAG       5736
Asn Ile Thr Met Lys Trp Leu Lys Asp Lys Gln Pro Met Asp Ala Lys
    235                 240                 245

GAG TTC GAA CCT AAA GAC GTA TTG CCC AAT GGG GAT GGG ACC TAC CAG       5784
Glu Phe Glu Pro Lys Asp Val Leu Pro Asn Gly Asp Gly Thr Tyr Gln
250                 255                 260                 265

GGC TGG ATA ACC TTG GCT GTA CCC CCT GGG GAA GAG CAG AGA TAT ACG       5832
Gly Trp Ile Thr Leu Ala Val Pro Pro Gly Glu Glu Gln Arg Tyr Thr
                270                 275                 280

TGC CAG GTG GAG CAC CCA GGC CTG GAT CAG CCC CTC ATT GTG ATC TGG G     5881
Cys Gln Val Glu His Pro Gly Leu Asp Gln Pro Leu Ile Val Ile Trp
                285                 290                 295

GTATGTGACT GATGAGAGCC AGGAGCTGAG AAAATCTATT GGGGGTTGAG AGGAGTGCCT     5941

GAGGAGGTAA TTATGGCAGT GAGATGAGGA TCTGCTCTTT GTTAGGGGGT GGGCTGAGGG     6001

TGGCAATCAA AGGCTTTAAC TTGCTTTTTC TGTTTTAG  AG CCC TCA CCG TCT         6053
                                          Glu Pro Ser Pro Ser
                                                          300

GGC ACC CTA GTC ATT GGA GTC ATC AGT GGA ATT GCT GTT TTT GTC GTC       6101
Gly Thr Leu Val Ile Gly Val Ile Ser Gly Ile Ala Val Phe Val Val
            305                 310                 315
```

-continued

```
ATC TTG TTC ATT GGA ATT TTG TTC ATA ATA TTA AGG AAG AGG CAG GGT         6149
Ile Leu Phe Ile Gly Ile Leu Phe Ile Ile Leu Arg Lys Arg Gln Gly
    320                 325                 330

TCA A GTGAGTAGGA ACAAGGGGGA AGTCTCTTAG TACCTCTGCC CCAGGGCACA           6203
Ser
335

GTGGGAAGAG GGGCAGAGGG GATCTGGCAT CCATGGGAAG CATTTTTCTC ATTTATATTC      6263

TTTGGGGACA CCAGCAGCTC CCTGGGAGAC AGAAAATAAT GGTTCTCCCC AGAATGAAAG      6323

TCTCTAATTC AACAAACATC TTCAGAGCAC CTACTATTTT GCAAGAGCTG TTTAAGGTAG      6383

TACAGGGGCT TTGAGGTTGA GAAGTCACTG TGGCTATTCT CAGAACCCAA ATCTGGTAGG      6443

GAATGAAATT GATAGCAAGT AAATGTAGTT AAAGAAGACC CCATGAGGTC CTAAAGCAGG      6503

CAGGAAGCAA ATGCTTAGGG TGTCAAAGGA AGAATGATC ACATTCAGCT GGGGATCAAG       6563

ATAGCCTTCT GGATCTTGAA GGAGAAGCTG GATTCCATTA GGTGAGGTTG AAGATGATGG      6623

GAGGTCTACA CAGACGGAGC AACCATGCCA AGTAGGAGAG TATAAGGCAT ACTGGGAGAT      6683

TAGAAATAAT TACTGTACCT TAACCCTGAG TTTGCGTAGC TATCACTCAC CAATTATGCA      6743

TTTCTACCCC CTGAACATCT GTGGTGTAGG GAAAAGAGAA TCAGAAAGAA GCCAGCTCAT      6803

ACAGAGTCCA AGGGTCTTTT GGGATATTGG GTTATGATCA CTGGGGTGTC ATTGAAGGAT      6863

CCTAAGAAAG GAGGACCACG ATCTCCCTTA TATGGTGAAT GTGTTGTTAA GAAGTTAGAT      6923

GAGAGGTGAG GAGACCAGTT AGAAAGCCAA TAAGCATTTC CAGATGAGAG ATAATGGTTC      6983

TTGAAATCCA ATAGTGCCCA GGTCTAAATT GAGATGGGTG AATGAGGAAA ATAAGGAAGA      7043

GAGAAGAGGC AAGATGGTGC CTAGGTTTGT GATGCCTCTT TCCTGGGTCT CTTGTCTCCA      7103

CAG  GA GGA GCC ATG GGG CAC TAC GTC TTA GCT GAA CGT GAG                7144
     Arg Gly Ala Met Gly His Tyr Val Leu Ala Glu Arg Glu
             340                 345

TGACACGCAG CCTGCAGACT CACTGTGGGA AGGAGACAAA ACTAGAGACT CAAAGAGGGA      7204

GTGCATTTAT GAGCTCTTCA TGTTTCAGGA GAGAGTTGAA CCTAAACATA GAAATTGCCT      7264

GACGAACTCC TTGATTTTAG CCTTCTCTGT TCATTTCCTC AAAAAGATTT CCCCATTTAG      7324

GTTTCTGAGT TCCTGCATGC CGGTGATCCC TAGCTGTGAC CTCTCCCCTG GAACTGTCTC      7384

TCATGAACCT CAAGCTGCAT CTAGAGGCTT CCTTCATTTC CTCCGTCACC TCAGAGACAT      7444

ACACCTATGT CATTTCATTT CCTATTTTTG GAAGAGGACT CCTTAAATTT GGGGGACTTA      7504

CATGATTCAT TTTAACATCT GAGAAAAGCT TTGAACCCTG GGACGTGGCT AGTCATAACC      7564

TTACCAGATT TTTACACATG TATCTATGCA TTTTCTGGAC CCGTTCAACT TTTCCTTTGA      7624

ATCCTCTCTC TGTGTTACCC AGTAACTCAT CTGTCACCAA GCCTTGGGGA TTCTTCCATC      7684

TGATTGTGAT GTGAGTTGCA CAGCTATGAA GGCTGTACAC TGCACGAATG GAAGAGGCAC      7744

CTGTCCCAGA AAAAGCATCA TGGCTATCTG TGGGTAGTAT GATGGGTGTT TTTAGCAGGT      7804

AGGAGGCAAA TATCTTGAAA GGGGTTGTGA AGAGGTGTTT TTTCTAATTG GCATGAAGGT      7864

GTCATACAGA TTTGCAAAGT TTAATGGTGC CTTCATTTGG GATGCTACTC TAGTATTCCA      7924

GACCTGAAGA ATCACAATAA TTTTCTACCT GGTCTCTCCT TGTTCTGATA ATGAAAATTA      7984

TGATAAGGAT GATAAAAGCA CTTACTTCGT GTCCGACTCT TCTGAGCACC TACTTACATG      8044

CATTACTGCA TGCACTTCTT ACAATAATTC TATGAGATAG GTACTATTAT CCCCATTTCT      8104

TTTTTAAATG AAGAAAGTGA AGTAGGCCGG GCACGGTGGC TCACGCCTGT AATCCCAGCA      8164

CTTTGGGAGG CCAAAGCGGG TGGATCACGA GGTCAGGAGA TCGAGACCAT CCTGGCTAAC      8224

ATGGTGAAAC CCCATCTCTA ATAAAATAC AAAAAATTAG CTGGGCGTGG TGGCAGACGC       8284
```

```
CTGTAGTCCC AGCTACTCGG AAGGCTGAGG CAGGAGAATG GCATGAACCC AGGAGGCAGA    8344

GCTTGCAGTG AGCCGAGTTT GCGCCACTGC ACTCCAGCCT AGGTGACAGA GTGAGACTCC    8404

ATCTCAAAAA AATAAAAATA AAAATAAAAA AATGAAAAAA AAAAGAAAGT GAAGTATAGA    8464

GTATCTCATA GTTTGTCAGT GATAGAAACA GGTTTCAAAC TCAGTCAATC TGACCGTTTG    8524

ATACATCTCA GACACCACTA CATTCAGTAG TTTAGATGCC TAGAATAAAT AGAGAAGGAA    8584

GGAGATGGCT CTTCTCTTGT CTCATTGTGT TTCTTCTGAG TGAGCTTGAA TCACATGAAG    8644

GGGAACAGCA GAAAACAACC AACTGATCCT CAGCTGTCAT GTTTCCTTTA AAAGTCCCTG    8704

AAGGAAGGTC CTGGAATGTG ACTCCCTTGC TCCTCTGTTG CTCTCTTTGG CATTCATTTC    8764

TTTGGACCCT ACGCAAGGAC TGTAATTGGT GGGGACAGCT AGTGGCCCTG CTGGGCTTCA    8824

CACACGGTGT CCTCCCTAGG CCAGTGCCTC TGGAGTCAGA ACTCTGGTGG TATTTCCCTC    8884

AATGAAGTGG AGTAAGCTCT CTCATTTTGA GATGGTATAA TGGAAGCCAC CAAGTGGCTT    8944

AGAGGATGCC CAGGTCCTTC CATGGAGCCA CTGGGGTTCC GGTGCACATT AAAAAAAAAA    9004

TCTAACCAGG ACATTCAGGA ATTGCTAGAT TCTGGGAAAT CAGTTCACCA TGTTCAAAAG    9064

AGTCTTTTTT TTTTTTTTGA GACTCTATTG CCCAGGCTGG AGTGCAATGG CATGATCTCG    9124

GCTCACTGTA ACCTCTGCCT CCCAGGTTCA AGCGATTCTC CTGTCTCAGC CTCCCAAGTA    9184

GCTGGGATTA CAGGCGTGCA CCACCATGCC CGGCTAATTT TTGTATTTTT AGTAGAGACA    9244

GGGTTTCACC ATGTTGGCCA GGCTGGTCTC GAACTCCT GACCTCGTGA TCCGCCTGCC    9304

TCGGCCTCCC AAAGTGCTGA GATTACAGGT GTGAGCCACC CTGCCCAGCC GTCAAAAGAG    9364

TCTTAATATA TATATCCAGA TGGCATGTGT TTACTTTATG TTACTACATG CACTTGGCTG    9424

CATAAATGTG GTACAAGCAT TCTGTCTTGA AGGGCAGGTG CTTCAGGATA CCATATACAG    9484

CTCAGAAGTT TCTTCTTTAG GCATTAAATT TTAGCAAAGA TATCTCATCT CTTCTTTTAA    9544

ACCATTTTCT TTTTTGTGG TTAGAAAAGT TATGTAGAAA AAAGTAAATG TGATTTACGC     9604

TCATTGTAGA AAAGCTATAA AATGAATACA ATTAAAGCTG TTATTTAATT AGCCAGTGAA    9664

AAACTATTAA CAACTTGTCT ATTACCTGTT AGTATTATTG TTGCATTAAA AATGCATATA    9724

CTTTAATAAA TGTATATTGT ATTGTATACT GCATGATTTT ATTGAAGTTC TTGTTCATCT    9784

TGTGTATATA CTTAATCGCT TTGTCATTTT GGAGACATTT ATTTTGCTTC TAATTTCTTT    9844

ACATTTGTC TTACGGAATA TTTTCATTCA ACTGTGGTAG CCGAATTAAT CGTGTTTCTT     9904

CACTCTAGGG ACATTGTCGT CTAAGTTGTA AGACATTGGT TATTTTACCA GCAAACCATT    9964

CTGAAAGCAT ATGACAAATT ATTTCTCTCT TAATATCTTA CTATACTGAA AGCAGACTGC   10024

TATAAGGCTT CACTTACTCT TCTACCTCAT AAGGAATATG TTACAATTAA TTTATTAGGT   10084

AAGCATTGT TTTATATTGG TTTTATTTCA CCTGGGCTGA GATTTCAAGA AACACCCCAG    10144

TCTTCACAGT AACACATTTC ACTAACACAT TTACTAAACA TCAGCAACTG TGGCCTGTTA   10204

ATTTTTTTAA TAGAAATTTT AAGTCCTCAT TTTCTTTCGG TGTTTTTTAA GCTTAATTTT   10264

TCTGGCTTTA TTCATAAATT CTTAAGGTCA ACTACATTTG AAAAATCAAA GACCTGCATT   10324

TTAAATTCTT ATTCACCTCT GGCAAAACCA TTCACAAACC ATGGTAGTAA AGAGAAGGGT   10384

GACACCTGGT GGCCATAGGT AAATGTACCA CGGTGGTCCG GTGACCAGAG ATGCAGCGCT   10444

GAGGGTTTTC CTGAAGGTAA AGGAATAAAG AATGGGTGGA GGGGCGTGCA CTGGAAATCA   10504

CTTGTAGAGA AAAGCCCCTG AAAATTTGAG AAAACAAACA AGAAACTACT TACCAGCTAT   10564

TTGAATTGCT GGAATCACAG GCCATTGCTG AGCTGCCTGA ACTGGGAACA CAACAGAAGG   10624
```

-continued

```
AAAACAAACC ACTCTGATAA TCATTGAGTC AAGTACAGCA GGTGATTGAG GACTGCTGAG      10684

AGGTACAGGC CAAAATTCTT ATGTTGTATT ATAATAATGT CATCTTATAA TACTGTCAGT      10744

ATTTTATAAA ACATTCTTCA CAAACTCACA CACATTTAAA AACAAAACAC TGTCTCTAAA      10804

ATCCCCAAAT TTTTCATAAA C                                               10825
```

(2) INFORMATION FOR SEQ ID NO:2:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
            20                  25                  30

Leu Phe Met Gly Ala Ser Glu Gln Asp Leu Gly Leu Ser Leu Phe Glu
        35                  40                  45

Ala Leu Gly Tyr Val Asp Asp Gln Leu Phe Val Phe Tyr Asp His Glu
    50                  55                  60

Ser Arg Arg Val Glu Pro Arg Thr Pro Trp Val Ser Ser Arg Ile Ser
65                  70                  75                  80

Ser Gln Met Trp Leu Gln Leu Ser Gln Ser Leu Lys Gly Trp Asp His
                85                  90                  95

Met Phe Thr Val Asp Phe Trp Thr Ile Met Glu Asn His Asn His Ser
            100                 105                 110

Lys Glu Ser His Thr Leu Gln Val Ile Leu Gly Cys Glu Met Gln Glu
        115                 120                 125

Asp Asn Ser Thr Glu Gly Tyr Trp Lys Tyr Gly Tyr Asp Gly Gln Asp
    130                 135                 140

His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
                165                 170                 175

Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Cys Gln Val Glu His Pro Gly
        275                 280                 285

Leu Asp Gln Pro Leu Ile Val Ile Trp Glu Pro Ser Pro Ser Gly Thr
    290                 295                 300

Leu Val Ile Gly Val Ile Ser Gly Ile Ala Val Phe Val Val Ile Leu
305                 310                 315                 320
```

```
Phe Ile Gly Ile Leu Phe Ile Ile Leu Arg Lys Arg Gln Gly Ser Arg
            325                 330                 335

Gly Ala Met Gly His Tyr Val Leu Ala Glu Arg Glu
            340                 345

(2) INFORMATION FOR SEQ ID NO:3:

(i) SEQUENCE CHARACTERISTICS:
        (A) LENGTH: 10825 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(361..436, 3762..4025, 4235..4510, 5606..
            5881, 6040..6153, 7107..7147)
        (D) OTHER INFORMATION: /product= "Hereditary Hemochromatosis
        (HH) protein containing the 24d1
            mutation"
            /note= "Hereditary Hemochromatosis (HH)
            gene 24d1 allele"

(ix) FEATURE:
        (A) NAME/KEY: -
        (B) LOCATION: 140..7319
        (D) OTHER INFORMATION: /note= "start and stop positions for
            24d1 allele cDNA (SEQ ID NO:10)"

(ix) FEATURE:
        (A) NAME/KEY: -
        (B) LOCATION: 3852..3891
        (D) OTHER INFORMATION: /note= "start and stop positions for
            genomic sequence surrounding variant
            for 24d2(C) allele (SEQ ID NO:41)"

(ix) FEATURE:
        (A) NAME/KEY: -
        (B) LOCATION: 5507..6023
        (D) OTHER INFORMATION: /note= "start and stop positions for
            genomic sequence surrounding variant
            for 24d1(A) allele (SEQ ID NO:21)"

(ix) FEATURE:
        (A) NAME/KEY: allele
        (B) LOCATION: replace(5834, "a")
        (D) OTHER INFORMATION: /phenotype= "Hereditary Hemochromatosis
            (HH)"/label= 24d1

(xi) SEQUENCE DESCRIPTION: SEQ ID NO:3:

TCTAAGGTTG AGATAAAATT TTTAAATGTA TGATTGAATT TTGAAAATCA TAAATATTTA      60

AATATCTAAA GTTCAGATCA GAACATTGCG AAGCTACTTT CCCCAATCAA CAACACCCCT    120

TCAGGATTTA AAAACCAAGG GGGACACTGG ATCACCTAGT GTTTCACAAG CAGGTACCTT    180

CTGCTGTAGG AGAGAGAGAA CTAAAGTTCT GAAAGACCTG TTGCTTTTCA CCAGGAAGTT    240

TTACTGGGCA TCTCCTGAGC CTAGGCAATA GCTGTAGGGT GACTTCTGGA GCCATCCCCG    300

TTTCCCCGCC CCCAAAAGA AGCGGAGATT TAACGGGGAC GTGCGGCCAG AGCTGGGGAA     360

ATG GGC CCG CGA GCC AGG CCG GCG CTT CTC CTC CTG ATG CTT TTG CAG     408
Met Gly Pro Arg Ala Arg Pro Ala Leu Leu Leu Leu Met Leu Leu Gln
  1               5                  10                  15

ACC GCG GTC CTG CAG GGG CGC TTG CTG C GTGAGTCCGA GGGCTGCGGG          456
Thr Ala Val Leu Gln Gly Arg Leu Leu
                20                  25

CGAACTAGGG GCGCGGCGGG GGTGGAAAAA TCGAAACTAG CTTTTTCTTT GCGCTTGGGA    516

GTTTGCTAAC TTTGGAGGAC CTGCTCAACC CTATCCGCAA GCCCCTCTCC CTACTTTCTG    576
```

```
CGTCCAGACC CCGTGAGGGA GTGCCTACCA CTGAACTGCA GATAGGGGTC CCTCGCCCCA     636

GGACCTGCCC CCTCCCCCGG CTGTCCCGGC TCTGCGGAGT GACTTTTGGA ACCGCCCACT     696

CCCTTCCCCC AACTAGAATG CTTTTAAATA AATCTCGTAG TTCCTCACTT GAGCTGAGCT     756

AAGCCTGGGG CTCCTTGAAC CTGGAACTCG GGTTTATTTC CAATGTCAGC TGTGCAGTTT     816

TTTCCCCAGT CATCTCCAAA CAGGAAGTTC TTCCCTGAGT GCTTGCCGAG AAGGCTGAGC     876

AAACCCACAG CAGGATCCGC ACGGGGTTTC CACCTCAGAA CGAATGCGTT GGGCGGTGGG     936

GGCGCGAAAG AGTGGCGTTG GGGATCTGAA TTCTTCACCA TTCCACCCAC TTTTGGTGAG     996

ACCTGGGGTG GAGGTCTCTA GGGTGGGAGG CTCCTGAGAG AGGCCTACCT CGGGCCTTTC    1056

CCCACTCTTG GCAATTGTTC TTTTGCCTGG AAAATTAAGT ATATGTTAGT TTGAACGTT     1116

TGAACTGAAC AATTCTCTTT TCGGCTAGGC TTTATTGATT TGCAATGTGC TGTGTAATTA    1176

AGAGGCCTCT CTACAAAGTA CTGATAATGA ACATGTAAGC AATGCACTCA CTTCTAAGTT    1236

ACATTCATAT CTGATCTTAT TTGATTTTCA CTAGGCATAG GGAGGTAGGA GCTAATAATA    1296

CGTTTATTTT ACTAGAAGTT AACTGGAATT CAGATTATAT AACTCTTTTC AGGTTACAAA    1356

GAACATAAAT AATCTGGTTT TCTGATGTTA TTTCAAGTAC TACAGCTGCT TCTAATCTTA    1416

GTTGACAGTG ATTTTGCCCT GTAGTGTAGC ACAGTGTTCT GTGGGTCACA CGCCGGCCTC    1476

AGCACAGCAC TTTGAGTTTT GGTACTACGT GTATCCACAT TTTACACATG ACAAGAATGA    1536

GGCATGGCAC GGCCTGCTTC CTGGCAAATT TATTCAATGG TACACTGGGC TTTGGTGGCA    1596

GAGCTCATGT CTCCACTTCA TAGCTATGAT TCTTAAACAT CACACTGCAT TAGAGGTTGA    1656

ATAATAAAAT TTCATGTTGA GCAGAAATAT TCATTGTTTA CAAGTGTAAA TGAGTCCCAG    1716

CCATGTGTTG CACTGTTCAA GCCCCAAGGG AGAGAGCAGG GAAACAAGTC TTTACCCTTT    1776

GATATTTTGC ATTCTAGTGG GAGAGATGAC AATAAGCAAA TGAGCAGAAA GATATACAAC    1836

ATCAGGAAAT CATGGGTGTT GTGAGAAGCA GAGAAGTCAG GGCAAGTCAC TCTGGGGCTG    1896

ACACTTGAGC AGAGACATGA AGGAAATAAG AATGATATTG ACTGGGAGCA GTATTTCCCA    1956

GGCAAACTGA GTGGGCCTGG CAAGTTGGAT TAAAAAGCGG GTTTTCTCAG CACTACTCAT    2016

GTGTGTGTGT GTGGGGGGGG GGGCGGCGT GGGGGTGGGA AGGGGACTA CCATCTGCAT     2076

GTAGGATGTC TAGCAGTATC CTGTCCTCCC TACTCACTAG GTGCTAGGAG CACTCCCCCA    2136

GTCTTGACAA CCAAAAATGT CTCTAAACTT TGCCACATGT CACCTAGTAG ACAAACTCCT    2196

GGTTAAGAAG CTCGGGTTGA AAAAAATAAA CAAGTAGTGC TGGGGAGTAG AGGCCAAGAA    2256

GTAGGTAATG GGCTCAGAAG AGGAGCCACA AACAAGGTTG TGCAGGCGCC TGTAGGCTGT    2316

GGTGTGAATT CTAGCCAAGG AGTAACAGTG ATCTGTCACA GGCTTTTAAA AGATTGCTCT    2376

GGCTGCTATG TGGAAAGCAG AATGAAGGGA GCAACAGTAA AAGCAGGGAG CCCAGCCAGG    2436

AAGCTGTTAC ACAGTCCAGG CAAGAGGTAG TGGAGTGGGC TGGGTGGGAA CAGAAAAGGG    2496

AGTGACAAAC CATTGTCTCC TGAATATATT CTGAAGGAAG TTGCTGAAGG ATTCTATGTT    2556

GTGTGAGAGA AAGAGAAGAA TTGGCTGGGT GTAGTAGCTC ATGCCAAGGA GGAGGCCAAG    2616

GAGAGCAGAT TCCTGAGCTC AGGAGTTCAA GACCAGCCTG GGCAACACAG CAAAACCCCT    2676

TCTCTACAAA AAATACAAAA ATTAGCTGGG TGTGGTGGCA TGCACCTGTG ATCCTAGCTA    2736

CTCGGGAGGC TGAGGTGGAG GGTATTGCTT GAGCCCAGGA AGTTGAGGCT GCAGTGAGCC    2796

ATGACTGTGC CACTGTACTT CAGCCTAGGT GACAGAGCAA GACCCTGTCT CCCCTGACCC    2856

CCTGAAAAAG AGAAGAGTTA AAGTTGACTT TGTTCTTTAT TTTAATTTTA TTGGCCTGAG    2916
```

```
CAGTGGGGTA ATTGGCAATG CCATTTCTGA GATGGTGAAG GCAGAGGAAA GAGCAGTTTG    2976

GGGTAAATCA AGGATCTGCA TTTGGGACAT GTTAAGTTTG AGATTCCAGT CAGGCTTCCA    3036

AGTGGTGAGG CCACATAGGC AGTTCAGTGT AAGAATTCAG GACCAAGGCT GGGCACGGTG    3096

GCTCACTTCT GTAATCCCAG CACTTTGGTG GCTGAGGCAG GTAGATCATT TGAGGTCAGG    3156

AGTTTGAGAC AAGCTTGGCC AACATGGTGA AACCCCATGT CTACTAAAAA TACAAAAATT    3216

AGCCTGGTGT GGTGGCGCAC GCCTATAGTC CCAGGTTTTC AGGAGGCTTA GGTAGGAGAA    3276

TCCCTTGAAC CCAGGAGGTG CAGGTTGCAG TGAGCTGAGA TTGTGCCACT GCACTCCAGC    3336

CTGGGTGATA GAGTGAGACT CTGTCTCAAA AAAAAAAAAA AAAAAAAAA AAAAAACTGA     3396

AGGAATTATT CCTCAGGATT TGGGTCTAAT TTGCCCTGAG CACCAACTCC TGAGTTCAAC    3456

TACCATGGCT AGACACACCT AACATTTTC TAGAATCCAC CAGCTTTAGT GGAGTCTGTC     3516

TAATCATGAG TATTGGAATA GGATCTGGGG GCAGTGAGGG GGTGGCAGCC ACGTGTGGCA    3576

GAGAAAAGCA CACAAGGAAA GAGCACCCAG GACTGTCATA TGGAAGAAAG ACAGGACTGC    3636

AACTCACCCT TCACAAAATG AGGACCAGAC ACAGCTGATG GTATGAGTTG ATGCAGGTGT    3696

GTGGAGCCTC AACATCCTGC TCCCCTCCTA CTACACATGG TTAAGGCCTG TTGCTCTGTC    3756
```

| TCCAG GT TCA CAC TCT CTG CAC TAC CTC TTC ATG GGT GCC TCA GAG<br>   Arg Ser His Ser Leu His Tyr Leu Phe Met Gly Ala Ser Glu<br>         30        35 | 3802 |

```
CAG GAC CTT GGT CTT TCC TTG TTT GAA GCT TTG GGC TAC GTG GAT GAC    3850
Gln Asp Leu Gly Leu Ser Leu Phe Glu Ala Leu Gly Tyr Val Asp Asp
 40              45                  50                  55

CAG CTG TTC GTG TTC TAT GAT CAT GAG AGT CGC CGT GTG GAG CCC CGA    3898
Gln Leu Phe Val Phe Tyr Asp His Glu Ser Arg Arg Val Glu Pro Arg
             60                  65                  70

ACT CCA TGG GTT TCC AGT AGA ATT TCA AGC CAG ATG TGG CTG CAG CTG    3946
Thr Pro Trp Val Ser Ser Arg Ile Ser Ser Gln Met Trp Leu Gln Leu
         75                  80                  85

AGT CAG AGT CTG AAA GGG TGG GAT CAC ATG TTC ACT GTT GAC TTC TGG    3994
Ser Gln Ser Leu Lys Gly Trp Asp His Met Phe Thr Val Asp Phe Trp
     90                  95                 100

ACT ATT ATG GAA AAT CAC AAC CAC AGC AAG G GTATGTGGAG AGGGGGCCTC     4045
Thr Ile Met Glu Asn His Asn His Ser Lys
    105                 110

ACCTTCCTGA GGTTGTCAGA GCTTTTCATC TTTTCATGCA TCTTGAAGGA AACAGCTGGA    4105

AGTCTGAGGT CTTGTGGGAG CAGGGAAGAG GGAAGGAATT TGCTTCCTGA GATCATTTGG    4165

TCCTTGGGGA TGGTGGAAAT AGGGACCTAT TCCTTTGGTT GCAGTTAACA AGGCTGGGGA    4225
```

| TTTTTCCAG  AG TCC CAC ACC CTG CAG GTC ATC CTG GGC TGT GAA ATG<br>     Glu Ser His Thr Leu Gln Val Ile Leu Gly Cys Glu Met<br>        115      120      125 | 4272 |

```
CAA GAA GAC AAC AGT ACC GAG GGC TAC TGG AAG TAC GGG TAT GAT GGG    4320
Gln Glu Asp Asn Ser Thr Glu Gly Tyr Trp Lys Tyr Gly Tyr Asp Gly
            130                 135                 140

CAG GAC CAC CTT GAA TTC TGC CCT GAC ACA CTG GAT TGG AGA GCA GCA    4368
Gln Asp His Leu Glu Phe Cys Pro Asp Thr Leu Asp Trp Arg Ala Ala
        145                 150                 155

GAA CCC AGG GCC TGG CCC ACC AAG CTG GAG TGG GAA AGG CAC AAG ATT    4416
Glu Pro Arg Ala Trp Pro Thr Lys Leu Glu Trp Glu Arg His Lys Ile
    160                 165                 170

CGG GCC AGG CAG AAC AGG GCC TAC CTG GAG AGG GAC TGC CCT GCA CAG    4464
Arg Ala Arg Gln Asn Arg Ala Tyr Leu Glu Arg Asp Cys Pro Ala Gln
175                 180                 185                 190

CTG CAG CAG TTG CTG GAG CTG GGG AGA GGT GTT TTG GAC CAA CAA G      4510
Leu Gln Gln Leu Leu Glu Leu Gly Arg Gly Val Leu Asp Gln Gln
```

```
Leu Gln Gln Leu Leu Glu Leu Gly Arg Gly Val Leu Asp Gln Gln
        195                 200                 205

GTATGGTGGA AACACACTTC TGCCCCTATA CTCTAGTGGC AGAGTGGAGG AGGTTGCAGG      4570

GCACGGAATC CCTGGTTGGA GTTTCAGAGG TGGCTGAGGC TGTGTGCCTC TCCAAATTCT      4630

GGGAAGGGAC TTTCTCAATC CTAGAGTCTC TACCTTATAA TTGAGATGTA TGAGACAGCC      4690

ACAAGTCATG GGTTTAATTT CTTTTCTCCA TGCATATGGC TCAAAGGGAA GTGTCTATGG      4750

CCCTTGCTTT TTATTTAACC AATAATCTTT TGTATATTTA TACCTGTTAA AAATTCAGAA      4810

ATGTCAAGGC CGGGCACGGT GGCTCACCCC TGTAATCCCA GCACTTTGGG AGGCCGAGGC      4870

GGGTGGTCAC AAGGTCAGGA GTTTGAGACC AGCCTGACCA ACATGGTGAA ACCCGTCTCT      4930

AAAAAAATAC AAAAATTAGC TGGTCACAGT CATGCGCACC TGTAGTCCCA GCTAATTGGA      4990

AGGCTGAGGC AGGAGCATCG CTTGAACCTG GGAAGCGGAA GTTGCACTGA GCCAAGATCG      5050

CGCCACTGCA CTCCAGCCTA GGCAGCAGAG TGAGACTCCA TCTTAAAAAA AAAAAAAAAA      5110

AAAAAAGAG AATTCAGAGA TCTCAGCTAT CATATGAATA CCAGGACAAA ATATCAAGTG       5170

AGGCCACTTA TCAGAGTAGA AGAATCCTTT AGGTTAAAAG TTTCTTTCAT AGAACATAGC      5230

AATAATCACT GAAGCTACCT ATCTTACAAG TCCGCTTCTT ATAACAATGC CTCCTAGGTT      5290

GACCCAGGTG AAACTGACCA TCTGTATTCA ATCATTTTCA ATGCACATAA AGGGCAATTT     5350

TATCTATCAG AACAAAGAAC ATGGGTAACA GATATGTATA TTTACATGTG AGGAGAACAA     5410

GCTGATCTGA CTGCTCTCCA AGTGACACTG TGTTAGAGTC CAATCTTAGG ACACAAAATG     5470

GTGTCTCTCC TGTAGCTTGT TTTTTTCTGA AAAGGGTATT TCCTTCCTCC AACCTATAGA     5530

AGGAAGTGAA AGTTCCAGTC TTCCTGGCAA GGGTAAACAG ATCCCCTCTC CTCATCCTTC    5590

CTCTTTCCTG TCAAG  TG CCT CCT TTG GTG AAG GTG ACA CAT CAT GTG ACC     5640
                    Val Pro Pro Leu Val Lys Val Thr His His Val Thr
                                        210                 215

TCT TCA GTG ACC ACT CTA CGG TGT CGG GCC TTG AAC TAC TAC CCC CAG      5688
Ser Ser Val Thr Thr Leu Arg Cys Arg Ala Leu Asn Tyr Tyr Pro Gln
        220                 225                 230

AAC ATC ACC ATG AAG TGG CTG AAG GAT AAG CAG CCA ATG GAT GCC AAG      5736
Asn Ile Thr Met Lys Trp Leu Lys Asp Lys Gln Pro Met Asp Ala Lys
    235                 240                 245

GAG TTC GAA CCT AAA GAC GTA TTG CCC AAT GGG GAT GGG ACC TAC CAG      5784
Glu Phe Glu Pro Lys Asp Val Leu Pro Asn Gly Asp Gly Thr Tyr Gln
250                 255                 260                 265

GGC TGG ATA ACC TTG GCT GTA CCC CCT GGG GAA GAG CAG AGA TAT ACG      5832
Gly Trp Ile Thr Leu Ala Val Pro Pro Gly Glu Glu Gln Arg Tyr Thr
        270                 275                 280

TAC CAG GTG GAG CAC CCA GGC CTG GAT CAG CCC CTC ATT GTG ATC TGG G   5881
Tyr Gln Val Glu His Pro Gly Leu Asp Gln Pro Leu Ile Val Ile Trp
            285                 290                 295

GTATGTGACT GATGAGAGCC AGGAGCTGAG AAAATCTATT GGGGGTTGAG AGGAGTGCCT    5941

GAGGAGGTAA TTATGGCAGT GAGATGAGGA TCTGCTCTTT GTTAGGGGGT GGGCTGAGGG    6001

TGGCAATCAA AGGCTTTAAC TTGCTTTTTC TGTTTTAG AG CCC TCA CCG TCT         6053
                                            Glu Pro Ser Pro Ser
                                                            300

GGC ACC CTA GTC ATT GGA GTC ATC AGT GGA ATT GCT GTT TTT GTC GTC      6101
Gly Thr Leu Val Ile Gly Val Ile Ser Gly Ile Ala Val Phe Val Val
            305                 310                 315

ATC TTG TTC ATT GGA ATT TTG TTC ATA ATA TTA AGG AAG AGG CAG GGT      6149
Ile Leu Phe Ile Gly Ile Leu Phe Ile Ile Leu Arg Lys Arg Gln Gly
        320                 325                 330
```

```
TCA A GTGAGTAGGA CAAGGGGGA AGTCTCTTAG TACCTCTGCC CCAGGGCACA        6203
Ser
335

GTGGGAAGAG GGGCAGAGGG GATCTGGCAT CCATGGGAAG CATTTTTCTC ATTTATATTC   6263

TTTGGGGACA CCAGCAGCTC CCTGGGAGAC AGAAAATAAT GGTTCTCCCC AGAATGAAAG   6323

TCTCTAATTC AACAAACATC TTCAGAGCAC CTACTATTTT GCAAGAGCTG TTTAAGGTAG   6383

TACAGGGGCT TTGAGGTTGA GAAGTCACTG TGGCTATTCT CAGAACCCAA ATCTGGTAGG   6443

GAATGAAATT GATAGCAAGT AAATGTAGTT AAAGAAGACC CCATGAGGTC CTAAAGCAGG   6503

CAGGAAGCAA ATGCTTAGGG TGTCAAAGGA AGAATGATC ACATTCAGCT GGGGATCAAG    6563

ATAGCCTTCT GGATCTTGAA GGAGAAGCTG GATTCCATTA GGTGAGGTTG AAGATGATGG   6623

GAGGTCTACA CAGACGGAGC AACCATGCCA AGTAGGAGAG TATAAGGCAT ACTGGGAGAT   6683

TAGAAATAAT TACTGTACCT TAACCCTGAG TTTGCGTAGC TATCACTCAC CAATTATGCA   6743

TTTCTACCCC CTGAACATCT GTGGTGTAGG GAAAAGAGAA TCAGAAAGAA GCCAGCTCAT   6803

ACAGAGTCCA AGGGTCTTTT GGGATATTGG GTTATGATCA CTGGGGTGTC ATTGAAGGAT   6863

CCTAAGAAAG GAGGACCACG ATCTCCCTTA TATGGTGAAT GTGTTGTTAA GAAGTTAGAT   6923

GAGAGGTGAG GAGACCAGTT AGAAAGCCAA TAAGCATTTC CAGATGAGAG ATAATGGTTC   6983

TTGAAATCCA ATAGTGCCCA GGTCTAAATT GAGATGGGTG AATGAGGAAA ATAAGGAAGA   7043

GAGAAGAGGC AAGATGGTGC CTAGGTTTGT GATGCCTCTT TCCTGGGTCT CTTGTCTCCA   7103

CAG  GA GGA GCC ATG GGG CAC TAC GTC TTA GCT GAA CGT GAG            7144
     Arg Gly Ala Met Gly His Tyr Val Leu Ala Glu Arg Glu
              340                 345

TGACACGCAG CCTGCAGACT CACTGTGGGA AGGAGACAAA ACTAGAGACT CAAAGAGGGA   7204

GTGCATTTAT GAGCTCTTCA TGTTTCAGGA GAGAGTTGAA CCTAAACATA GAAATTGCCT   7264

GACGAACTCC TTGATTTTAG CCTTCTCTGT TCATTTCCTC AAAAAGATTT CCCCATTTAG   7324

GTTTCTGAGT TCCTGCATGC CGGTGATCCC TAGCTGTGAC CTCTCCCCTG GAACTGTCTC   7384

TCATGAACCT CAAGCTGCAT CTAGAGGCTT CCTTCATTTC CTCCGTCACC TCAGAGACAT   7444

ACACCTATGT CATTTCATTT CCTATTTTTG GAAGAGGACT CCTTAAATTT GGGGGACTTA   7504

CATGATTCAT TTTAACATCT GAGAAAAGCT TTGAACCCTG GGACGTGGCT AGTCATAACC   7564

TTACCAGATT TTTACACATG TATCTATGCA TTTTCTGGAC CCGTTCAACT TTTCCTTTGA   7624

ATCCTCTCTC TGTGTTACCC AGTAACTCAT CTGTCACCAA GCCTTGGGGA TTCTTCCATC   7684

TGATTGTGAT GTGAGTTGCA CAGCTATGAA GGCTGTACAC TGCACGAATG AAGAGGCAC    7744

CTGTCCCAGA AAAAGCATCA TGGCTATCTG TGGGTAGTAT GATGGGTGTT TTTAGCAGGT   7804

AGGAGGCAAA TATCTTGAAA GGGGTTGTGA AGAGGTGTTT TTTCTAATTG GCATGAAGGT   7864

GTCATACAGA TTTGCAAAGT TTAATGGTGC CTTCATTTGG GATGCTACTC TAGTATTCCA   7924

GACCTGAAGA ATCACAATAA TTTTCTACCT GGTCTCTCCT TGTTCTGATA ATGAAAATTA   7984

TGATAAGGAT GATAAAAGCA CTTACTTCGT GTCCGACTCT TCTGAGCACC TACTTACATG   8044

CATTACTGCA TGCACTTCTT ACAATAATTC TATGAGATAG GTACTATTAT CCCCATTTCT   8104

TTTTTAAATG AAGAAAGTGA AGTAGGCCGG GCACGGTGGC TCACGCCTGT AATCCCAGCA   8164

CTTTGGGAGG CCAAAGCGGG TGGATCACGA GGTCAGGAGA TCGAGACCAT CCTGGCTAAC   8224

ATGGTGAAAC CCCATCTCTA ATAAAAATAC AAAAAATTAG CTGGGCGTGG TGGCAGACGC   8284

CTGTAGTCCC AGCTACTCGG AAGGCTGAGG CAGGAGAATG GCATGAACCC AGGAGGCAGA   8344

GCTTGCAGTG AGCCGAGTTT GCGCCACTGC ACTCCAGCCT AGGTGACAGA GTGAGACTCC   8404
```

```
ATCTCAAAAA AATAAAAATA AAAATAAAAA AATGAAAAAA AAAAGAAAGT GAAGTATAGA    8464

GTATCTCATA GTTTGTCAGT GATAGAAACA GGTTTCAAAC TCAGTCAATC TGACCGTTTG    8524

ATACATCTCA GACACCACTA CATTCAGTAG TTTAGATGCC TAGAATAAAT AGAGAAGGAA    8584

GGAGATGGCT CTTCTCTTGT CTCATTGTGT TTCTTCTGAG TGAGCTTGAA TCACATGAAG    8644

GGGAACAGCA GAAAACAACC AACTGATCCT CAGCTGTCAT GTTTCCTTTA AAAGTCCCTG    8704

AAGGAAGGTC CTGGAATGTG ACTCCCTTGC TCCTCTGTTG CTCTCTTTGG CATTCATTTC    8764

TTTGGACCCT ACGCAAGGAC TGTAATTGGT GGGGACAGCA GTGGCCCTG CTGGGCTTCA     8824

CACACGGTGT CCTCCCTAGG CCAGTGCCTC TGGAGTCAGA ACTCTGGTGG TATTTCCCTC    8884

AATGAAGTGG AGTAAGCTCT CTCATTTTGA GATGGTATAA TGGAAGCCAC CAAGTGGCTT    8944

AGAGGATGCC CAGGTCCTTC CATGGAGCCA CTGGGGTTCC GGTGCACATT AAAAAAAAAA    9004

TCTAACCAGG ACATTCAGGA ATTGCTAGAT TCTGGGAAAT CAGTTCACCA TGTTCAAAAG    9064

AGTCTTTTTT TTTTTTTTGA GACTCTATTG CCCAGGCTGG AGTGCAATGG CATGATCTCG    9124

GCTCACTGTA ACCTCTGCCT CCCAGGTTCA AGCGATTCTC CTGTCTCAGC CTCCCAAGTA    9184

GCTGGGATTA CAGGCGTGCA CCACCATGCC CGGCTAATTT TTGTATTTTT AGTAGAGACA    9244

GGGTTTCACC ATGTTGGCCA GGCTGGTCTC GAACTCTCCT GACCTCGTGA TCCGCCTGCC    9304

TCGGCCTCCC AAAGTGCTGA GATTACAGGT GTGAGCCACC CTGCCCAGCC GTCAAAAGAG    9364

TCTTAATATA TATATCCAGA TGGCATGTGT TTACTTTATG TTACTACATG CACTTGGCTG    9424

CATAAATGTG GTACAAGCAT TCTGTCTTGA AGGGCAGGTG CTTCAGGATA CCATATACAG    9484

CTCAGAAGTT TCTTCTTTAG GCATTAAATT TTAGCAAAGA TATCTCATCT CTTCTTTTAA    9544

ACCATTTTCT TTTTTTGTGG TTAGAAAAGT TATGTAGAAA AAAGTAAATG TGATTTACGC    9604

TCATTGTAGA AAAGCTATAA AATGAATACA ATTAAAGCTG TTATTTAATT AGCCAGTGAA    9664

AAACTATTAA CAACTTGTCT ATTACCTGTT AGTATTATTG TTGCATTAAA AATGCATATA    9724

CTTTAATAAA TGTATATTGT ATTGTATACT GCATGATTTT ATTGAAGTTC TTGTTCATCT    9784

TGTGTATATA CTTAATCGCT TTGTCATTTT GGAGACATTT ATTTTGCTTC TAATTTCTTT    9844

ACATTTGTC TTACGGAATA TTTTCATTCA ACTGTGGTAG CCGAATTAAT CGTGTTTCTT     9904

CACTCTAGGG ACATTGTCGT CTAAGTTGTA AGACATTGGT TATTTTACCA GCAAACCATT    9964

CTGAAAGCAT ATGACAAATT ATTTCTCTCT TAATATCTTA CTATACTGAA AGCAGACTGC    10024

TATAAGGCTT CACTTACTCT TCTACCTCAT AAGGAATATG TTACAATTAA TTTATTAGGT    10084

AAGCATTTGT TTTATATTGG TTTTATTTCA CCTGGGCTGA GATTTCAAGA ACACCCCAG     10144

TCTTCACAGT AACACATTTC ACTAACACAT TTACTAAACA TCAGCAACTG TGGCCTGTTA    10204

ATTTTTTTAA TAGAAATTTT AAGTCCTCAT TTTCTTTCGG TGTTTTTTAA GCTTAATTTT    10264

TCTGGCTTTA TTCATAAATT CTTAAGGTCA ACTACATTTG AAAAATCAAA GACCTGCATT    10324

TTAAATTCTT ATTCACCTCT GGCAAAACCA TTCACAAACC ATGGTAGTAA AGAGAAGGGT    10384

GACACCTGGT GGCCATAGGT AAATGTACCA CGGTGGTCCG GTGACCAGAG ATGCAGCGCT    10444

GAGGGTTTTC CTGAAGGTAA AGGAATAAAG AATGGGTGGA GGGGCGTGCA CTGGAAATCA    10504

CTTGTAGAGA AAAGCCCCTG AAAATTTGAG AAAACAAACA AGAAACTACT TACCAGCTAT    10564

TTGAATTGCT GGAATCACAG GCCATTGCTG AGCTGCCTGA ACTGGGAACA CAACAGAAGG    10624

AAAACAAACC ACTCTGATAA TCATTGAGTC AAGTACAGCA GGTGATTGAG GACTGCTGAG    10684

AGGTACAGGC CAAAATTCTT ATGTTGTATT ATAATAATGT CATCTTATAA TACTGTCAGT    10744
```

```
ATTTTATAAA ACATTCTTCA CAAACTCACA CACATTTAAA AACAAAACAC TGTCTCTAAA    10804

ATCCCCAAAT TTTTCATAAA C                                              10825
```

(2) INFORMATION FOR SEQ ID NO:4:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
                20                  25                  30

Leu Phe Met Gly Ala Ser Glu Gln Asp Leu Gly Leu Ser Leu Phe Glu
         35                  40                  45

Ala Leu Gly Tyr Val Asp Asp Gln Leu Phe Val Phe Tyr Asp His Glu
 50                  55                  60

Ser Arg Arg Val Glu Pro Arg Thr Pro Trp Val Ser Ser Arg Ile Ser
 65                  70                  75                  80

Ser Gln Met Trp Leu Gln Leu Ser Gln Ser Leu Lys Gly Trp Asp His
                85                  90                  95

Met Phe Thr Val Asp Phe Trp Thr Ile Met Glu Asn His Asn His Ser
            100                 105                 110

Lys Glu Ser His Thr Leu Gln Val Ile Leu Gly Cys Glu Met Gln Glu
        115                 120                 125

Asp Asn Ser Thr Glu Gly Tyr Trp Lys Tyr Gly Tyr Asp Gly Gln Asp
130                 135                 140

His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
                165                 170                 175

Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Tyr Gln Val Glu His Pro Gly
        275                 280                 285

Leu Asp Gln Pro Leu Ile Val Ile Trp Glu Pro Ser Pro Ser Gly Thr
    290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335
```

Gly Ala Met Gly His Tyr Val Leu Ala Glu Arg Glu
                340                 345

(2) INFORMATION FOR SEQ ID NO:5:

(i) SEQUENCE CHARACTERISTICS:
       (A) LENGTH: 10825 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: join(361..436, 3762..4025, 4235..4510, 5606..
           5881, 6040..6153, 7107..7147)
       (D) OTHER INFORMATION: /product= "Hereditary Hemochromatosis
       (HH) protein containing the 24d2
           mutation"
           /note= "Hereditary Hemochromatosis (HH)
           gene 24d2 allele"

(ix) FEATURE:
       (A) NAME/KEY: -
       (B) LOCATION: 140..7319
       (D) OTHER INFORMATION: /note= "start and stop positions for
           24d2 allele cDNA (SEQ ID NO:11)"

(ix) FEATURE:
       (A) NAME/KEY: -
       (B) LOCATION: 3852..3891
       (D) OTHER INFORMATION: /note= "start and stop positions for
           genomic sequence surrounding variant
           for 24d2(G) allele (SEQ ID NO:42)"

(ix) FEATURE:
       (A) NAME/KEY: -
       (B) LOCATION: 5507..6023
       (D) OTHER INFORMATION: /note= "start and stop positions for
           genomic sequence surrounding variant
           for 24d1(G) allele (SEQ ID NO:20)"

(ix) FEATURE:
       (A) NAME/KEY: allele
       (B) LOCATION: replace(3872, "g")
       (D) OTHER INFORMATION: /phenotype= "Hereditary Hemochromatosis
       (HH)"/label= 24d2

(xi) SEQUENCE DESCRIPTION: SEQ ID NO:5:

```
TCTAAGGTTG AGATAAAATT TTTAAATGTA TGATTGAATT TTGAAAATCA TAAATATTTA      60

AATATCTAAA GTTCAGATCA GAACATTGCG AAGCTACTTT CCCCAATCAA CACACCCCT      120

TCAGGATTTA AAAACCAAGG GGGACACTGG ATCACCTAGT GTTTCACAAG CAGGTACCTT     180

CTGCTGTAGG AGAGAGAGAA CTAAAGTTCT GAAAGACCTG TTGCTTTTCA CCAGGAAGTT     240

TTACTGGGCA TCTCCTGAGC CTAGGCAATA GCTGTAGGGT GACTTCTGGA GCCATCCCCG     300

TTTCCCCGCC CCCAAAAGA AGCGGAGATT TAACGGGGAC GTGCGGCCAG AGCTGGGAA       360

ATG GGC CCG CGA GCC AGG CCG GCG CTT CTC CTC CTG ATG CTT TTG CAG      408
Met Gly Pro Arg Ala Arg Pro Ala Leu Leu Leu Leu Met Leu Leu Gln
  1               5                  10                  15

ACC GCG GTC CTG CAG GGG CGC TTG CTG C GTGAGTCCGA GGGCTGCGGG          456
Thr Ala Val Leu Gln Gly Arg Leu Leu
              20                  25

CGAACTAGGG GCGCGGCGGG GGTGGAAAAA TCGAAACTAG CTTTTTCTTT GCGCTTGGGA    516

GTTTGCTAAC TTTGGAGGAC CTGCTCAACC CTATCCGCAA GCCCCTCTCC CTACTTTCTG    576

CGTCCAGACC CCGTGAGGGA GTGCCTACCA CTGAACTGCA GATAGGGGTC CCTCGCCCCA    636

GGACCTGCCC CCTCCCCCGG CTGTCCCGGC TCTGCGGAGT GACTTTTGGA ACCGCCCACT    696
```

-continued

```
CCCTTCCCCC AACTAGAATG CTTTTAAATA AATCTCGTAG TTCCTCACTT GAGCTGAGCT    756

AAGCCTGGGG CTCCTTGAAC CTGGAACTCG GGTTTATTTC CAATGTCAGC TGTGCAGTTT    816

TTTCCCCAGT CATCTCCAAA CAGGAAGTTC TTCCCTGAGT GCTTGCCGAG AAGGCTGAGC    876

AAACCCACAG CAGGATCCGC ACGGGGTTTC CACCTCAGAA CGAATGCGTT GGGCGGTGGG    936

GGCGCGAAAG AGTGGCGTTG GGGATCTGAA TTCTTCACCA TTCCACCCAC TTTTGGTGAG    996

ACCTGGGGTG GAGGTCTCTA GGGTGGGAGG CTCCTGAGAG AGGCCTACCT CGGGCCTTTC   1056

CCCACTCTTG GCAATTGTTC TTTTGCCTGG AAAATTAAGT ATATGTTAGT TTTGAACGTT   1116

TGAACTGAAC AATTCTCTTT TCGGCTAGGC TTTATTGATT TGCAATGTGC TGTGTAATTA   1176

AGAGGCCTCT CTACAAAGTA CTGATAATGA ACATGTAAGC AATGCACTCA CTTCTAAGTT   1236

ACATTCATAT CTGATCTTAT TTGATTTTCA CTAGGCATAG GGAGGTAGGA GCTAATAATA   1296

CGTTTATTTT ACTAGAAGTT AACTGGAATT CAGATTATAT AACTCTTTTC AGGTTACAAA   1356

GAACATAAAT AATCTGGTTT TCTGATGTTA TTTCAAGTAC TACAGCTGCT TCTAATCTTA   1416

GTTGACAGTG ATTTTGCCCT GTAGTGTAGC ACAGTGTTCT GTGGGTCACA CGCCGGCCTC   1476

AGCACAGCAC TTTGAGTTTT GGTACTACGT GTATCCACAT TTTACACATG ACAAGAATGA   1536

GGCATGGCAC GGCCTGCTTC CTGGCAAATT TATTCAATGG TACACTGGGC TTTGGTGGCA   1596

GAGCTCATGT CTCCACTTCA TAGCTATGAT TCTTAAACAT CACACTGCAT TAGAGGTTGA   1656

ATAATAAAAT TCATGTTGA GCAGAAATAT TCATTGTTTA CAAGTGTAAA TGAGTCCCAG    1716

CCATGTGTTG CACTGTTCAA GCCCCAAGGG AGAGAGCAGG GAAACAAGTC TTTACCCTTT   1776

GATATTTTGC ATTCTAGTGG GAGAGATGAC AATAAGCAAA TGAGCAGAAA GATATACAAC   1836

ATCAGGAAAT CATGGGTGTT GTGAGAAGCA GAGAAGTCAG GGCAAGTCAC TCTGGGGCTG   1896

ACACTTGAGC AGAGACATGA AGGAAATAAG AATGATATTG ACTGGGAGCA GTATTTCCCA   1956

GGCAAACTGA GTGGGCCTGG CAAGTTGGAT TAAAAAGCGG GTTTTCTCAG CACTACTCAT   2016

GTGTGTGTGT GTGGGGGGGG GGGCGGCGT GGGGGTGGGA AGGGGACTA CCATCTGCAT    2076

GTAGGATGTC TAGCAGTATC CTGTCCTCCC TACTCACTAG GTGCTAGGAG CACTCCCCCA   2136

GTCTTGACAA CCAAAAATGT CTCTAAACTT TGCCACATGT CACCTAGTAG ACAAACTCCT   2196

GGTTAAGAAG CTCGGGTTGA AAAAAATAAA CAAGTAGTGC TGGGGAGTAG AGGCCAAGAA   2256

GTAGGTAATG GGCTCAGAAG AGGAGCCACA AACAAGGTTG TGCAGGCGCC TGTAGGCTGT   2316

GGTGTGAATT CTAGCCAAGG AGTAACAGTG ATCTGTCACA GGCTTTTAAA AGATTGCTCT   2376

GGCTGCTATG TGGAAAGCAG AATGAAGGGA GCAACAGTAA AAGCAGGGAG CCCAGCCAGG   2436

AAGCTGTTAC ACAGTCCAGG CAAGAGGTAG TGGAGTGGGC TGGGTGGGAA CAGAAAAGGG   2496

AGTGACAAAC CATTGTCTCC TGAATATATT CTGAAGGAAG TTGCTGAAGG ATTCTATGTT   2556

GTGTGAGAGA AAGAGAAGAA TTGGCTGGGT GTAGTAGCTC ATGCCAAGGA GGAGGCCAAG   2616

GAGAGCAGAT TCCTGAGCTC AGGAGTTCAA GACCAGCCTG GGCAACACAG CAAAACCCCT   2676

TCTCTACAAA AAATACAAAA ATTAGCTGGG TGTGGTGGCA TGCACCTGTG ATCCTAGCTA   2736

CTCGGGAGGC TGAGGTGGAG GGTATTGCTT GAGCCCAGGA AGTTGAGGCT GCAGTGAGCC   2796

ATGACTGTGC CACTGTACTT CAGCCTAGGT GACAGAGCAA GACCCTGTCT CCCCTGACCC   2856

CCTGAAAAAG AGAAGAGTTA AAGTTGACTT TGTTCTTTAT TTTAATTTTA TTGGCCTGAG   2916

CAGTGGGGTA ATTGGCAATG CCATTTCTGA GATGGTGAAG GCAGAGGAAA GAGCAGTTTG   2976

GGGTAAATCA AGGATCTGCA TTTGGGACAT GTTAAGTTTG AGATTCCAGT CAGGCTTCCA   3036
```

```
AGTGGTGAGG CCACATAGGC AGTTCAGTGT AAGAATTCAG GACCAAGGCT GGGCACGGTG    3096

GCTCACTTCT GTAATCCCAG CACTTTGGTG GCTGAGGCAG GTAGATCATT TGAGGTCAGG    3156

AGTTTGAGAC AAGCTTGGCC AACATGGTGA AACCCCATGT CTACTAAAAA TACAAAAATT    3216

AGCCTGGTGT GGTGGCGCAC GCCTATAGTC CCAGGTTTTC AGGAGGCTTA GGTAGGAGAA    3276

TCCCTTGAAC CCAGGAGGTG CAGGTTGCAG TGAGCTGAGA TTGTGCCACT GCACTCCAGC    3336

CTGGGTGATA GAGTGAGACT CTGTCTCAAA AAAAAAAAA AAAAAAAAA AAAAACTGA     3396

AGGAATTATT CCTCAGGATT TGGGTCTAAT TTGCCCTGAG CACCAACTCC TGAGTTCAAC    3456

TACCATGGCT AGACACACCT AACATTTTC TAGAATCCAC CAGCTTTAGT GGAGTCTGTC    3516

TAATCATGAG TATTGGAATA GGATCTGGGG GCAGTGAGGG GGTGGCAGCC ACGTGTGGCA    3576

GAGAAAAGCA CACAAGGAAA GAGCACCCAG GACTGTCATA TGGAAGAAAG ACAGGACTGC    3636

AACTCACCCT TCACAAAATG AGGACCAGAC ACAGCTGATG GTATGAGTTG ATGCAGGTGT    3696

GTGGAGCCTC AACATCCTGC TCCCCTCCTA CTACACATGG TTAAGGCCTG TTGCTCTGTC    3756

TCCAG  GT TCA CAC TCT CTG CAC TAC CTC TTC ATG GGT GCC TCA GAG        3802
       Arg Ser His Ser Leu His Tyr Leu Phe Met Gly Ala Ser Glu
            30                 35

CAG GAC CTT GGT CTT TCC TTG TTT GAA GCT TTG GGC TAC GTG GAT GAC      3850
Gln Asp Leu Gly Leu Ser Leu Phe Glu Ala Leu Gly Tyr Val Asp Asp
 40                  45                  50                  55

CAG CTG TTC GTG TTC TAT GAT GAT GAG AGT CGC CGT GTG GAG CCC CGA      3898
Gln Leu Phe Val Phe Tyr Asp Asp Glu Ser Arg Arg Val Glu Pro Arg
             60                  65                  70

ACT CCA TGG GTT TCC AGT AGA ATT TCA AGC CAG ATG TGG CTG CAG CTG      3946
Thr Pro Trp Val Ser Ser Arg Ile Ser Ser Gln Met Trp Leu Gln Leu
         75                  80                  85

AGT CAG AGT CTG AAA GGG TGG GAT CAC ATG TTC ACT GTT GAC TTC TGG      3994
Ser Gln Ser Leu Lys Gly Trp Asp His Met Phe Thr Val Asp Phe Trp
     90                  95                 100

ACT ATT ATG GAA AAT CAC AAC CAC AGC AAG G GTATGTGGAG AGGGGGCCTC      4045
Thr Ile Met Glu Asn His Asn His Ser Lys
    105                 110

ACCTTCCTGA GGTTGTCAGA GCTTTTCATC TTTTCATGCA TCTTGAAGGA AACAGCTGGA    4105

AGTCTGAGGT CTTGTGGGAG CAGGGAAGAG GGAAGGAATT TGCTTCCTGA GATCATTTGG    4165

TCCTTGGGGA TGGTGGAAAT AGGGACCTAT TCCTTTGGTT GCAGTTAACA AGGCTGGGGA    4225

TTTTTCCAG  AG TCC CAC ACC CTG CAG GTC ATC CTG GGC TGT GAA ATG       4272
           Glu Ser His Thr Leu Gln Val Ile Leu Gly Cys Glu Met
               115                 120                 125

CAA GAA GAC AAC AGT ACC GAG GGC TAC TGG AAG TAC GGG TAT GAT GGG      4320
Gln Glu Asp Asn Ser Thr Glu Gly Tyr Trp Lys Tyr Gly Tyr Asp Gly
         130                 135                 140

CAG GAC CAC CTT GAA TTC TGC CCT GAC ACA CTG GAT TGG AGA GCA GCA      4368
Gln Asp His Leu Glu Phe Cys Pro Asp Thr Leu Asp Trp Arg Ala Ala
     145                 150                 155

GAA CCC AGG GCC TGG CCC ACC AAG CTG GAG TGG GAA AGG CAC AAG ATT      4416
Glu Pro Arg Ala Trp Pro Thr Lys Leu Glu Trp Glu Arg His Lys Ile
 160                 165                 170

CGG GCC AGG CAG AAC AGG GCC TAC CTG GAG AGG GAC TGC CCT GCA CAG      4464
Arg Ala Arg Gln Asn Arg Ala Tyr Leu Glu Arg Asp Cys Pro Ala Gln
175                 180                 185                 190

CTG CAG CAG TTG CTG GAG CTG GGG AGA GGT GTT TTG GAC CAA CAA G        4510
Leu Gln Gln Leu Leu Glu Leu Gly Arg Gly Val Leu Asp Gln Gln
                195                 200                 205

GTATGGTGGA AACACACTTC TGCCCCTATA CTCTAGTGGC AGAGTGGAGG AGGTTGCAGG    4570
```

```
GCACGGAATC CCTGGTTGGA GTTTCAGAGG TGGCTGAGGC TGTGTGCCTC TCCAAATTCT    4630

GGGAAGGGAC TTTCTCAATC CTAGAGTCTC TACCTTATAA TTGAGATGTA TGAGACAGCC    4690

ACAAGTCATG GGTTTAATTT CTTTTCTCCA TGCATATGGC TCAAAGGGAA GTGTCTATGG    4750

CCCTTGCTTT TTATTTAACC AATAATCTTT TGTATATTTA TACCTGTTAA AAATTCAGAA    4810

ATGTCAAGGC CGGGCACGGT GGCTCACCCC TGTAATCCCA GCACTTTGGG AGGCCGAGGC    4870

GGGTGGTCAC AAGGTCAGGA GTTTGAGACC AGCCTGACCA ACATGGTGAA ACCCGTCTCT    4930

AAAAAAATAC AAAAATTAGC TGGTCACAGT CATGCGCACC TGTAGTCCCA GCTAATTGGA    4990

AGGCTGAGGC AGGAGCATCG CTTGAACCTG GGAAGCGGAA GTTGCACTGA GCCAAGATCG    5050

CGCCACTGCA CTCCAGCCTA GGCAGCGAGT GAGACTCCA TCTTAAAAAA AAAAAAAAAA    5110

AAAAAAAGAG AATTCAGAGA TCTCAGCTAT CATATGAATA CCAGGACAAA ATATCAAGTG    5170

AGGCCACTTA TCAGAGTAGA AGAATCCTTT AGGTTAAAAG TTTCTTTCAT AGAACATAGC    5230

AATAATCACT GAAGCTACCT ATCTTACAAG TCCGCTTCTT ATAACAATGC CTCCTAGGTT    5290

GACCCAGGTG AAACTGACCA TCTGTATTCA ATCATTTTCA ATGCACATAA AGGGCAATTT    5350

TATCTATCAG AACAAAGAAC ATGGGTAACA GATATGTATA TTTACATGTG AGGAGAACAA    5410

GCTGATCTGA CTGCTCTCCA AGTGACACTG TGTTAGAGTC CAATCTTAGG ACACAAAATG    5470

GTGTCTCTCC TGTAGCTTGT TTTTTTCTGA AAAGGGTATT TCCTTCCTCC AACCTATAGA    5530

AGGAAGTGAA AGTTCCAGTC TTCCTGGCAA GGGTAAACAG ATCCCCTCTC CTCATCCTTC    5590

CTCTTTCCTG TCAAG  TG CCT CCT TTG GTG AAG GTG ACA CAT CAT GTG ACC    5640
                  Val Pro Pro Leu Val Lys Val Thr His His Val Thr
                              210                 215

TCT TCA GTG ACC ACT CTA CGG TGT CGG GCC TTG AAC TAC TAC CCC CAG    5688
Ser Ser Val Thr Thr Leu Arg Cys Arg Ala Leu Asn Tyr Tyr Pro Gln
        220                 225                 230

AAC ATC ACC ATG AAG TGG CTG AAG GAT AAG CAG CCA ATG GAT GCC AAG    5736
Asn Ile Thr Met Lys Trp Leu Lys Asp Lys Gln Pro Met Asp Ala Lys
    235                 240                 245

GAG TTC GAA CCT AAA GAC GTA TTG CCC AAT GGG GAT GGG ACC TAC CAG    5784
Glu Phe Glu Pro Lys Asp Val Leu Pro Asn Gly Asp Gly Thr Tyr Gln
250                 255                 260                 265

GGC TGG ATA ACC TTG GCT GTA CCC CCT GGG GAA GAG CAG AGA TAT ACG    5832
Gly Trp Ile Thr Leu Ala Val Pro Pro Gly Glu Glu Gln Arg Tyr Thr
                270                 275                 280

TGC CAG GTG GAG CAC CCA GGC CTG GAT CAG CCC CTC ATT GTG ATC TGG G  5881
Cys Gln Val Glu His Pro Gly Leu Asp Gln Pro Leu Ile Val Ile Trp
            285                 290                 295

GTATGTGACT GATGAGAGCC AGGAGCTGAG AAAATCTATT GGGGGTTGAG AGGAGTGCCT    5941

GAGGAGGTAA TTATGGCAGT GAGATGAGGA TCTGCTCTTT GTTAGGGGGT GGGCTGAGGG    6001

TGGCAATCAA AGGCTTTAAC TTGCTTTTTC TGTTTTAG  AG CCC TCA CCG TCT    6053
                                           Glu Pro Ser Pro Ser
                                                       300

GGC ACC CTA GTC ATT GGA GTC ATC AGT GGA ATT GCT GTT TTT GTC GTC    6101
Gly Thr Leu Val Ile Gly Val Ile Ser Gly Ile Ala Val Phe Val Val
            305                 310                 315

ATC TTG TTC ATT GGA ATT TTG TTC ATA ATA TTA AGG AAG AGG CAG GGT    6149
Ile Leu Phe Ile Gly Ile Leu Phe Ile Ile Leu Arg Lys Arg Gln Gly
        320                 325                 330

TCA A GTGAGTAGGA ACAAGGGGGA AGTCTCTTAG TACCTCTGCC CCAGGGCACA    6203
Ser
335
```

```
GTGGGAAGAG GGGCAGAGGG GATCTGGCAT CCATGGGAAG CATTTTTCTC ATTTATATTC      6263

TTTGGGGACA CCAGCAGCTC CCTGGGAGAC AGAAAATAAT GGTTCTCCCC AGAATGAAAG      6323

TCTCTAATTC AACAAACATC TTCAGAGCAC CTACTATTTT GCAAGAGCTG TTTAAGGTAG      6383

TACAGGGGCT TTGAGGTTGA GAAGTCACTG TGGCTATTCT CAGAACCCAA ATCTGGTAGG      6443

GAATGAAATT GATAGCAAGT AAATGTAGTT AAAGAAGACC CCATGAGGTC CTAAAGCAGG      6503

CAGGAAGCAA ATGCTTAGGG TGTCAAAGGA AAGAATGATC ACATTCAGCT GGGGATCAAG      6563

ATAGCCTTCT GGATCTTGAA GGAGAAGCTG GATTCCATTA GGTGAGGTTG AAGATGATGG      6623

GAGGTCTACA CAGACGGAGC AACCATGCCA AGTAGGAGAG TATAAGGCAT ACTGGGAGAT      6683

TAGAAATAAT TACTGTACCT TAACCCTGAG TTTGCGTAGC TATCACTCAC CAATTATGCA      6743

TTTCTACCCC CTGAACATCT GTGGTGTAGG GAAAAGAGAA TCAGAAAGAA GCCAGCTCAT      6803

ACAGAGTCCA AGGGTCTTTT GGGATATTGG GTTATGATCA CTGGGGTGTC ATTGAAGGAT      6863

CCTAAGAAAG GAGGACCACG ATCTCCCTTA TATGGTGAAT GTGTTGTTAA GAAGTTAGAT      6923

GAGAGGTGAG GAGACCAGTT AGAAAGCCAA TAAGCATTTC CAGATGAGAG ATAATGGTTC      6983

TTGAAATCCA ATAGTGCCCA GGTCTAAATT GAGATGGGTG AATGAGGAAA ATAAGGAAGA      7043

GAGAAGAGGC AAGATGGTGC CTAGGTTTGT GATGCCTCTT TCCTGGGTCT CTTGTCTCCA      7103

CAG  GA GGA GCC ATG GGG CAC TAC GTC TTA GCT GAA CGT GAG                7144
     Arg Gly Ala Met Gly His Tyr Val Leu Ala Glu Arg Glu
                 340                     345

TGACACGCAG CCTGCAGACT CACTGTGGGA AGGAGACAAA ACTAGAGACT CAAAGAGGGA      7204

GTGCATTTAT GAGCTCTTCA TGTTTCAGGA GAGAGTTGAA CCTAAACATA GAAATTGCCT      7264

GACGAACTCC TTGATTTTAG CCTTCTCTGT TCATTTCCTC AAAAAGATTT CCCCATTTAG      7324

GTTTCTGAGT TCCTGCATGC CGGTGATCCC TAGCTGTGAC CTCTCCCCTG GAACTGTCTC      7384

TCATGAACCT CAAGCTGCAT CTAGAGGCTT CCTTCATTTC CTCCGTCACC TCAGAGACAT      7444

ACACCTATGT CATTTCATTT CCTATTTTTG GAAGAGGACT CCTTAAATTT GGGGGACTTA      7504

CATGATTCAT TTTAACATCT GAGAAAAGCT TTGAACCCTG GGACGTGGCT AGTCATAACC      7564

TTACCAGATT TTTACACATG TATCTATGCA TTTTCTGGAC CCGTTCAACT TTTCCTTTGA      7624

ATCCTCTCTC TGTGTTACCC AGTAACTCAT CTGTCACCAA GCCTTGGGGA TTCTTCCATC      7684

TGATTGTGAT GTGAGTTGCA CAGCTATGAA GGCTGTACAC TGCACGAATG AAGAGGCAC       7744

CTGTCCCAGA AAAAGCATCA TGGCTATCTG TGGGTAGTAT GATGGGTGTT TTTAGCAGGT      7804

AGGAGGCAAA TATCTTGAAA GGGGTTGTGA AGAGGTGTTT TTTCTAATTG GCATGAAGGT      7864

GTCATACAGA TTTGCAAAGT TTAATGGTGC CTTCATTTGG GATGCTACTC TAGTATTCCA      7924

GACCTGAAGA ATCACAATAA TTTTCTACCT GGTCTCTCCT TGTTCTGATA ATGAAAATTA      7984

TGATAAGGAT GATAAAAGCA CTTACTTCGT GTCCGACTCT TCTGAGCACC TACTTACATG      8044

CATTACTGCA TGCACTTCTT ACAATAATTC TATGAGATAG GTACTATTAT CCCCATTTCT      8104

TTTTTAAATG AAGAAAGTGA AGTAGGCCGG GCACGGTGGC TCACGCCTGT AATCCCAGCA      8164

CTTTGGGAGG CCAAAGCGGG TGGATCACGA GGTCAGGAGA TCGAGACCAT CCTGGCTAAC      8224

ATGGTGAAAC CCCATCTCTA ATAAAAATAC AAAAAATTAG CTGGGCGTGG TGGCAGACGC      8284

CTGTAGTCCC AGCTACTCGG AAGGCTGAGG CAGGAGAATG GCATGAACCC AGGAGGCAGA      8344

GCTTGCAGTG AGCCGAGTTT GCGCCACTGC ACTCCAGCCT AGGTGACAGA GTGAGACTCC      8404

ATCTCAAAAA AATAAAAATA AAAATAAAAA AATGAAAAAA AAAGAAAGT GAAGTATAGA       8464

GTATCTCATA GTTTGTCAGT GATAGAAACA GGTTTCAAAC TCAGTCAATC TGACCGTTTG      8524
```

```
ATACATCTCA GACACCACTA CATTCAGTAG TTTAGATGCC TAGAATAAAT AGAGAAGGAA     8584
GGAGATGGCT CTTCTCTTGT CTCATTGTGT TTCTTCTGAG TGAGCTTGAA TCACATGAAG     8644
GGGAACAGCA GAAAACAACC AACTGATCCT CAGCTGTCAT GTTTCCTTTA AAAGTCCCTG     8704
AAGGAAGGTC CTGGAATGTG ACTCCCTTGC TCCTCTGTTG CTCTCTTTGG CATTCATTTC     8764
TTTGGACCCT ACGCAAGGAC TGTAATTGGT GGGGACAGCT AGTGGCCCTG CTGGGCTTCA     8824
CACACGGTGT CCTCCCTAGG CCAGTGCCTC TGGAGTCAGA ACTCTGGTGG TATTTCCCTC     8884
AATGAAGTGG AGTAAGCTCT CTCATTTTGA GATGGTATAA TGGAAGCCAC CAAGTGGCTT     8944
AGAGGATGCC CAGGTCCTTC CATGGAGCCA CTGGGGTTCC GGTGCACATT AAAAAAAAAA     9004
TCTAACCAGG ACATTCAGGA ATTGCTAGAT TCTGGGAAAT CAGTTCACCA TGTTCAAAAG     9064
AGTCTTTTTT TTTTTTTTGA GACTCTATTG CCCAGGCTGG AGTGCAATGG CATGATCTCG     9124
GCTCACTGTA ACCTCTGCCT CCCAGGTTCA AGCGATTCTC CTGTCTCAGC CTCCCAAGTA     9184
GCTGGGATTA CAGGCGTGCA CCACCATGCC CGGCTAATTT TTGTATTTTT AGTAGAGACA     9244
GGGTTTCACC ATGTTGGCCA GGCTGGTCTC GAACTCCTT GACCTCGTGA TCCGCCTGCC      9304
TCGGCCTCCC AAAGTGCTGA GATTACAGGT GTGAGCCACC CTGCCCAGCC GTCAAAAGAG     9364
TCTTAATATA TATATCCAGA TGGCATGTGT TTACTTTATG TTACTACATG CACTTGGCTG     9424
CATAAATGTG GTACAAGCAT TCTGTCTTGA AGGGCAGGTG CTTCAGGATA CCATATACAG     9484
CTCAGAAGTT TCTTCTTTAG GCATTAAATT TTAGCAAAGA TATCTCATCT CTTCTTTTAA     9544
ACCATTTTCT TTTTTTGTGG TTAGAAAAGT TATGTAGAAA AAAGTAAATG TGATTTACGC     9604
TCATTGTAGA AAAGCTATAA AATGAATACA ATTAAAGCTG TTATTTAATT AGCCAGTGAA     9664
AAACTATTAA CAACTTGTCT ATTACCTGTT AGTATTATTG TTGCATTAAA AATGCATATA     9724
CTTTAATAAA TGTATATTGT ATTGTATACT GCATGATTTT ATTGAAGTTC TTGTTCATCT     9784
TGTGTATATA CTTAATCGCT TTGTCATTTT GGAGACATTT ATTTTGCTTC TAATTTCTTT     9844
ACATTTGTC TTACGGAATA TTTTCATTCA ACTGTGGTAG CCGAATTAAT CGTGTTTCTT      9904
CACTCTAGGG ACATTGTCGT CTAAGTTGTA AGACATTGGT TATTTTACCA GCAAACCATT     9964
CTGAAAGCAT ATGACAAATT ATTTCTCTCT TAATATCTTA CTATACTGAA AGCAGACTGC     10024
TATAAGGCTT CACTTACTCT TCTACCTCAT AAGGAATATG TTACAATTAA TTTATTAGGT     10084
AAGCATTTGT TTTATATTGG TTTTATTTCA CCTGGGCTGA GATTTCAAGA AACACCCCAG     10144
TCTTCACAGT AACACATTTC ACTAACACAT TTACTAAACA TCAGCAACTG TGGCCTGTTA     10204
ATTTTTTTAA TAGAAATTTT AAGTCCTCAT TTTCTTTCGG TGTTTTTTAA GCTTAATTTT     10264
TCTGGCTTTA TTCATAAATT CTTAAGGTCA ACTACATTTG AAAAATCAAA GACCTGCATT     10324
TTAAATTCTT ATTCACCTCT GGCAAAACCA TTCACAAACC ATGGTAGTAA AGAGAAGGGT     10384
GACACCTGGT GGCCATAGGT AAATGTACCA CGGTGGTCCG GTGACCAGAG ATGCAGCGCT     10444
GAGGGTTTTC CTGAAGGTAA AGGAATAAAG AATGGGTGGA GGGGCGTGCA CTGGAAATCA     10504
CTTGTAGAGA AAAGCCCCTG AAAATTTGAG AAAACAAACA AGAAACTACT TACCAGCTAT     10564
TTGAATTGCT GGAATCACAG GCCATTGCTG AGCTGCCTGA ACTGGGAACA CAACAGAAGG     10624
AAAACAAACC ACTCTGATAA TCATTGAGTC AAGTACAGCA GGTGATTGAG GACTGCTGAG     10684
AGGTACAGGC CAAAATTCTT ATGTTGTATT ATAATAATGT CATCTTATAA TACTGTCAGT     10744
ATTTTATAAA ACATTCTTCA CAAACTCACA CACATTTAAA AACAAAACAC TGTCTCTAAA     10804
ATCCCCAAAT TTTTCATAAA C                                              10825
```

(2) INFORMATION FOR SEQ ID NO:6:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
                20                  25                  30

Leu Phe Met Gly Ala Ser Glu Gln Asp Leu Gly Leu Ser Leu Phe Glu
            35                  40                  45

Ala Leu Gly Tyr Val Asp Asp Gln Leu Phe Val Phe Tyr Asp Asp Glu
        50                  55                  60

Ser Arg Arg Val Glu Pro Arg Thr Pro Trp Val Ser Ser Arg Ile Ser
65                  70                  75                  80

Ser Gln Met Trp Leu Gln Leu Ser Gln Ser Leu Lys Gly Trp Asp His
                85                  90                  95

Met Phe Thr Val Asp Phe Trp Thr Ile Met Glu Asn His Asn His Ser
            100                 105                 110

Lys Glu Ser His Thr Leu Gln Val Ile Leu Gly Cys Glu Met Gln Glu
        115                 120                 125

Asp Asn Ser Thr Glu Gly Tyr Trp Lys Tyr Gly Tyr Asp Gly Gln Asp
    130                 135                 140

His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
                165                 170                 175

Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Cys Gln Val Glu His Pro Gly
        275                 280                 285

Leu Asp Gln Pro Leu Ile Val Ile Trp Glu Pro Ser Pro Ser Gly Thr
    290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335

Gly Ala Met Gly His Tyr Val Leu Ala Glu Arg Glu
            340                 345
```

(2) INFORMATION FOR SEQ ID NO:7:

(i) SEQUENCE CHARACTERISTICS:
        (A) LENGTH: 10825 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(361..436, 3762..4025, 4235..4510, 5606..
            5881, 6040..6153, 7107..7147)
        (D) OTHER INFORMATION: /product= "Hereditary Hemochromatosis
            (HH) protein containing both the 24d1
            and 24d2 mutations"
            /note= "Hereditary Hemochromatosis (HH)
            gene containing a combination of both
            24d1 and 24d2 alleles"

(ix) FEATURE:
        (A) NAME/KEY: -
        (B) LOCATION: 140..7319
        (D) OTHER INFORMATION: /note= "start and stop positions for
            cDNA containing a combination of both
            24d1 and 24d2 alleles (SEQ ID NO:12)"

(ix) FEATURE:
        (A) NAME/KEY: -
        (B) LOCATION: 3852..3891
        (D) OTHER INFORMATION: /note= "start and stop positions for
            genomic sequence surrounding variant
            for 24d2(G) allele (SEQ ID NO:42)"

(ix) FEATURE:
        (A) NAME/KEY: -
        (B) LOCATION: 5507..6023
        (D) OTHER INFORMATION: /note= "start and stop positions for
            genomic sequence surrounding variant
            for 24d1(A) allele (SEQ ID NO:21)"

(ix) FEATURE:
        (A) NAME/KEY: allele
        (B) LOCATION: replace(3872, "g")
        (D) OTHER INFORMATION: /phenotype= "Hereditary Hemochromatosis
        (HH)"/label= 24d2

(ix) FEATURE:
        (A) NAME/KEY: allele
        (B) LOCATION: replace(5834, "a")
        (D) OTHER INFORMATION: /phenotype= "Hereditary Hemochromatosis
        (HH)"/label= 24d1

(xi) SEQUENCE DESCRIPTION: SEQ ID NO:7:

```
TCTAAGGTTG AGATAAAATT TTTAAATGTA TGATTGAATT TTGAAAATCA TAAATATTTA      60

AATATCTAAA GTTCAGATCA GAACATTGCG AAGCTACTTT CCCCAATCAA CAACACCCCT     120

TCAGGATTTA AAACCAAGG  GGGACACTGG ATCACCTAGT GTTTCACAAG CAGGTACCTT     180

CTGCTGTAGG AGAGAGAGAA CTAAAGTTCT GAAAGACCTG TTGCTTTTCA CCAGGAAGTT     240

TTACTGGGCA TCTCCTGAGC CTAGGCAATA GCTGTAGGGT GACTTCTGGA GCCATCCCCG     300

TTTCCCCGCC CCCAAAAGA  AGCGGAGATT TAACGGGGAC GTGCGGCCAG AGCTGGGGAA     360

ATG GGC CCG CGA GCC AGG CCG GCG CTT CTC CTC CTG ATG CTT TTG CAG      408
Met Gly Pro Arg Ala Arg Pro Ala Leu Leu Leu Leu Met Leu Leu Gln
 1               5                  10                  15

ACC GCG GTC CTG CAG GGG CGC TTG CTG C GTGAGTCCGA GGGCTGCGGG           456
Thr Ala Val Leu Gln Gly Arg Leu Leu
                20                  25

CGAACTAGGG GCGCGGCGGG GGTGGAAAAA TCGAAACTAG CTTTTTCTTT GCGCTTGGGA     516

GTTTGCTAAC TTTGGAGGAC CTGCTCAACC CTATCCGCAA GCCCCTCTCC CTACTTTCTG     576
```

```
CGTCCAGACC CCGTGAGGGA GTGCCTACCA CTGAACTGCA GATAGGGGTC CCTCGCCCCA    636

GGACCTGCCC CCTCCCCCGG CTGTCCCGGC TCTGCGGAGT GACTTTTGGA ACCGCCCACT    696

CCCTTCCCCC AACTAGAATG CTTTTAAATA AATCTCGTAG TTCCTCACTT GAGCTGAGCT    756

AAGCCTGGGG CTCCTTGAAC CTGGAACTCG GGTTTATTTC CAATGTCAGC TGTGCAGTTT    816

TTTCCCCAGT CATCTCCAAA CAGGAAGTTC TTCCCTGAGT GCTTGCCGAG AAGGCTGAGC    876

AAACCCACAG CAGGATCCGC ACGGGGTTTC CACCTCAGAA CGAATGCGTT GGGCGGTGGG    936

GGCGCGAAAG AGTGGCGTTG GGGATCTGAA TTCTTCACCA TTCCACCCAC TTTTGGTGAG    996

ACCTGGGGTG GAGGTCTCTA GGGTGGGAGG CTCCTGAGAG AGGCCTACCT CGGGCCTTTC   1056

CCCACTCTTG GCAATTGTTC TTTTGCCTGG AAAATTAAGT ATATGTTAGT TTGAACGTT    1116

TGAACTGAAC AATTCTCTTT TCGGCTAGGC TTTATTGATT TGCAATGTGC TGTGTAATTA   1176

AGAGGCCTCT CTACAAAGTA CTGATAATGA ACATGTAAGC AATGCACTCA CTTCTAAGTT   1236

ACATTCATAT CTGATCTTAT TTGATTTTCA CTAGGCATAG GGAGGTAGGA GCTAATAATA   1296

CGTTTATTTT ACTAGAAGTT AACTGGAATT CAGATTATAT AACTCTTTTC AGGTTACAAA   1356

GAACATAAAT AATCTGGTTT TCTGATGTTA TTTCAAGTAC TACAGCTGCT TCTAATCTTA   1416

GTTGACAGTG ATTTTGCCCT GTAGTGTAGC ACAGTGTTCT GTGGGTCACA CGCCGGCCTC   1476

AGCACAGCAC TTTGAGTTTT GGTACTACGT GTATCCACAT TTTACACATG ACAAGAATGA   1536

GGCATGGCAC GGCCTGCTTC CTGGCAAATT TATTCAATGG TACACTGGGC TTTGGTGGCA   1596

GAGCTCATGT CTCCACTTCA TAGCTATGAT TCTTAAACAT CACACTGCAT TAGAGGTTGA   1656

ATAATAAAAT TCATGTTGA GCAGAAATAT TCATTGTTTA CAAGTGTAAA TGAGTCCCAG    1716

CCATGTGTTG CACTGTTCAA GCCCCAAGGG AGAGAGCAGG GAAACAAGTC TTTACCCTTT   1776

GATATTTTGC ATTCTAGTGG GAGAGATGAC AATAAGCAAA TGAGCAGAAA GATATACAAC   1836

ATCAGGAAAT CATGGGTGTT GTGAGAAGCA GAGAAGTCAG GGCAAGTCAC TCTGGGGCTG   1896

ACACTTGAGC AGAGACATGA AGGAAATAAG AATGATATTG ACTGGGAGCA GTATTTCCCA   1956

GGCAAACTGA GTGGGCCTGG CAAGTTGGAT TAAAAAGCGG GTTTTCTCAG CACTACTCAT   2016

GTGTGTGTGT GTGGGGGGGG GGGCGGCGT GGGGGTGGGA AGGGGACTA CCATCTGCAT    2076

GTAGGATGTC TAGCAGTATC CTGTCCTCCC TACTCACTAG GTGCTAGGAG CACTCCCCCA   2136

GTCTTGACAA CCAAAAATGT CTCTAAACTT TGCCACATGT CACCTAGTAG ACAAACTCCT   2196

GGTTAAGAAG CTCGGGTTGA AAAAAATAAA CAAGTAGTGC TGGGGAGTAG AGGCCAAGAA   2256

GTAGGTAATG GGCTCAGAAG AGGAGCCACA AACAAGGTTG TGCAGGCGCC TGTAGGCTGT   2316

GGTGTGAATT CTAGCCAAGG AGTAACAGTG ATCTGTCACA GGCTTTTAAA AGATTGCTCT   2376

GGCTGCTATG TGGAAAGCAG AATGAAGGGA GCAACAGTAA AAGCAGGGAG CCCAGCCAGG   2436

AAGCTGTTAC ACAGTCCAGG CAAGAGGTAG TGGAGTGGGC TGGGTGGGAA CAGAAAAGGG   2496

AGTGACAAAC CATTGTCTCC TGAATATATT CTGAAGGAAG TTGCTGAAGG ATTCTATGTT   2556

GTGTGAGAGA AAGAGAAGAA TTGGCTGGGT GTAGTAGCTC ATGCCAAGGA GGAGGCCAAG   2616

GAGAGCAGAT TCCTGAGCTC AGGAGTTCAA GACCAGCCTG GGCAACACAG CAAAACCCCT   2676

TCTCTACAAA AAATACAAAA ATTAGCTGGG TGTGGTGGCA TGCACCTGTG ATCCTAGCTA   2736

CTCGGGAGGC TGAGGTGGAG GGTATTGCTT GAGCCCAGGA AGTTGAGGCT GCAGTGAGCC   2796

ATGACTGTGC CACTGTACTT CAGCCTAGGT GACAGAGCAA GACCCTGTCT CCCCTGACCC   2856

CCTGAAAAAG AGAAGAGTTA AAGTTGACTT TGTTCTTTAT TTTAATTTTA TTGGCCTGAG   2916
```

```
CAGTGGGGTA ATTGGCAATG CCATTTCTGA GATGGTGAAG GCAGAGGAAA GAGCAGTTTG      2976

GGGTAAATCA AGGATCTGCA TTTGGGACAT GTTAAGTTTG AGATTCCAGT CAGGCTTCCA      3036

AGTGGTGAGG CCACATAGGC AGTTCAGTGT AAGAATTCAG GACCAAGGCT GGGCACGGTG      3096

GCTCACTTCT GTAATCCCAG CACTTTGGTG GCTGAGGCAG GTAGATCATT TGAGGTCAGG      3156

AGTTTGAGAC AAGCTTGGCC AACATGGTGA AACCCCATGT CTACTAAAAA TACAAAAATT      3216

AGCCTGGTGT GGTGGCGCAC GCCTATAGTC CCAGGTTTTC AGGAGGCTTA GGTAGGAGAA      3276

TCCCTTGAAC CCAGGAGGTG CAGGTTGCAG TGAGCTGAGA TTGTGCCACT GCACTCCAGC      3336

CTGGGTGATA GAGTGAGACT CTGTCTCAAA AAAAAAAAAA AAAAAAAAAA AAAAAACTGA      3396

AGGAATTATT CCTCAGGATT TGGGTCTAAT TTGCCCTGAG CACCAACTCC TGAGTTCAAC      3456

TACCATGGCT AGACACACCT AACATTTTC TAGAATCCAC CAGCTTTAGT GGAGTCTGTC       3516

TAATCATGAG TATTGGAATA GGATCTGGGG GCAGTGAGGG GGTGGCAGCC ACGTGTGGCA      3576

GAGAAAAGCA CACAAGGAAA GAGCACCCAG GACTGTCATA TGGAAGAAAG ACAGGACTGC      3636

AACTCACCCT TCACAAAATG AGGACCAGAC ACAGCTGATG GTATGAGTTG ATGCAGGTGT      3696

GTGGAGCCTC AACATCCTGC TCCCCTCCTA CTACACATGG TTAAGGCCTG TTGCTCTGTC      3756

TCCAG  GT TCA CAC TCT CTG CAC TAC CTC TTC ATG GGT GCC TCA GAG          3802
       Arg Ser His Ser Leu His Tyr Leu Phe Met Gly Ala Ser Glu
                         30                  35

CAG GAC CTT GGT CTT TCC TTG TTT GAA GCT TTG GGC TAC GTG GAT GAC        3850
Gln Asp Leu Gly Leu Ser Leu Phe Glu Ala Leu Gly Tyr Val Asp Asp
 40                  45                  50                  55

CAG CTG TTC GTG TTC TAT GAT GAT GAG AGT CGC CGT GTG GAG CCC CGA        3898
Gln Leu Phe Val Phe Tyr Asp Asp Glu Ser Arg Arg Val Glu Pro Arg
                 60                  65                  70

ACT CCA TGG GTT TCC AGT AGA ATT TCA AGC CAG ATG TGG CTG CAG CTG        3946
Thr Pro Trp Val Ser Ser Arg Ile Ser Ser Gln Met Trp Leu Gln Leu
             75                  80                  85

AGT CAG AGT CTG AAA GGG TGG GAT CAC ATG TTC ACT GTT GAC TTC TGG        3994
Ser Gln Ser Leu Lys Gly Trp Asp His Met Phe Thr Val Asp Phe Trp
         90                  95                 100

ACT ATT ATG GAA AAT CAC AAC CAC AGC AAG G GTATGTGGAG AGGGGGCCTC        4045
Thr Ile Met Glu Asn His Asn His Ser Lys
     105                 110

ACCTTCCTGA GGTTGTCAGA GCTTTTCATC TTTTCATGCA TCTTGAAGGA AACAGCTGGA      4105

AGTCTGAGGT CTTGTGGGAG CAGGGAAGAG GGAAGGAATT TGCTTCCTGA GATCATTTGG      4165

TCCTTGGGGA TGGTGGAAAT AGGGACCTAT TCCTTTGGTT GCAGTTAACA AGGCTGGGA       4225

TTTTTCCAG  AG TCC CAC ACC CTG CAG GTC ATC CTG GGC TGT GAA ATG          4272
           Glu Ser His Thr Leu Gln Val Ile Leu Gly Cys Glu Met
                     115                 120                 125

CAA GAA GAC AAC AGT ACC GAG GGC TAC TGG AAG TAC GGG TAT GAT GGG        4320
Gln Glu Asp Asn Ser Thr Glu Gly Tyr Trp Lys Tyr Gly Tyr Asp Gly
             130                 135                 140

CAG GAC CAC CTT GAA TTC TGC CCT GAC ACA CTG GAT TGG AGA GCA GCA        4368
Gln Asp His Leu Glu Phe Cys Pro Asp Thr Leu Asp Trp Arg Ala Ala
         145                 150                 155

GAA CCC AGG GCC TGG CCC ACC AAG CTG GAG TGG GAA AGG CAC AAG ATT        4416
Glu Pro Arg Ala Trp Pro Thr Lys Leu Glu Trp Glu Arg His Lys Ile
     160                 165                 170

CGG GCC AGG CAG AAC AGG GCC TAC CTG GAG AGG GAC TGC CCT GCA CAG        4464
Arg Ala Arg Gln Asn Arg Ala Tyr Leu Glu Arg Asp Cys Pro Ala Gln
175                 180                 185                 190

CTG CAG CAG TTG CTG GAG CTG GGG AGA GGT GTT TTG GAC CAA CAA G          4510
Leu Gln Gln Leu Leu Glu Leu Gly Arg Gly Val Leu Asp Gln Gln
```

```
Leu Gln Gln Leu Leu Glu Leu Gly Arg Gly Val Leu Asp Gln Gln
        195                 200                 205

GTATGGTGGA AACACACTTC TGCCCCTATA CTCTAGTGGC AGAGTGGAGG AGGTTGCAGG    4570

GCACGGAATC CCTGGTTGGA GTTTCAGAGG TGGCTGAGGC TGTGTGCCTC TCCAAATTCT    4630

GGGAAGGGAC TTTCTCAATC CTAGAGTCTC TACCTTATAA TTGAGATGTA TGAGACAGCC    4690

ACAAGTCATG GGTTTAATTT CTTTTCTCCA TGCATATGGC TCAAAGGGAA GTGTCTATGG    4750

CCCTTGCTTT TTATTTAACC AATAATCTTT TGTATATTTA TACCTGTTAA AAATTCAGAA    4810

ATGTCAAGGC CGGGCACGGT GGCTCACCCC TGTAATCCCA GCACTTTGGG AGGCCGAGGC    4870

GGGTGGTCAC AAGGTCAGGA GTTTGAGACC AGCCTGACCA ACATGGTGAA ACCCGTCTCT    4930

AAAAAAATAC AAAAATTAGC TGGTCACAGT CATGCGCACC TGTAGTCCCA GCTAATTGGA    4990

AGGCTGAGGC AGGAGCATCG CTTGAACCTG GGAAGCGGAA GTTGCACTGA GCCAAGATCG    5050

CGCCACTGCA CTCCAGCCTA GGCAGCAGAG TGAGACTCCA TCTTAAAAAA AAAAAAAAAA    5110

AAAAAAGAG AATTCAGAGA TCTCAGCTAT CATATGAATA CCAGGACAAA ATATCAAGTG     5170

AGGCCACTTA TCAGAGTAGA AGAATCCTTT AGGTTAAAAG TTTCTTTCAT AGAACATAGC    5230

AATAATCACT GAAGCTACCT ATCTTACAAG TCCGCTTCTT ATAACAATGC CTCCTAGGTT    5290

GACCCAGGTG AAACTGACCA TCTGTATTCA ATCATTTTCA ATGCACATAA AGGGCAATTT    5350

TATCTATCAG AACAAAGAAC ATGGGTAACA GATATGTATA TTTACATGTG AGGAGAACAA    5410

GCTGATCTGA CTGCTCTCCA AGTGACACTG TGTTAGAGTC CAATCTTAGG ACACAAAATG    5470

GTGTCTCTCC TGTAGCTTGT TTTTTTCTGA AAAGGGTATT TCCTTCCTCC AACCTATAGA    5530

AGGAAGTGAA AGTTCCAGTC TTCCTGGCAA GGGTAAACAG ATCCCCTCTC CTCATCCTTC    5590

CTCTTTCCTG TCAAG  TG CCT CCT TTG GTG AAG GTG ACA CAT CAT GTG ACC    5640
                    Val Pro Pro Leu Val Lys Val Thr His His Val Thr
                                    210                 215

TCT TCA GTG ACC ACT CTA CGG TGT CGG GCC TTG AAC TAC TAC CCC CAG     5688
Ser Ser Val Thr Thr Leu Arg Cys Arg Ala Leu Asn Tyr Tyr Pro Gln
        220                 225                 230

AAC ATC ACC ATG AAG TGG CTG AAG GAT AAG CAG CCA ATG GAT GCC AAG     5736
Asn Ile Thr Met Lys Trp Leu Lys Asp Lys Gln Pro Met Asp Ala Lys
        235                 240                 245

GAG TTC GAA CCT AAA GAC GTA TTG CCC AAT GGG GAT GGG ACC TAC CAG     5784
Glu Phe Glu Pro Lys Asp Val Leu Pro Asn Gly Asp Gly Thr Tyr Gln
250                 255                 260                 265

GGC TGG ATA ACC TTG GCT GTA CCC CCT GGG GAA GAG CAG AGA TAT ACG     5832
Gly Trp Ile Thr Leu Ala Val Pro Pro Gly Glu Glu Gln Arg Tyr Thr
            270                 275                 280

TAC CAG GTG GAG CAC CCA GGC CTG GAT CAG CCC CTC ATT GTG ATC TGG G   5881
Tyr Gln Val Glu His Pro Gly Leu Asp Gln Pro Leu Ile Val Ile Trp
            285                 290                 295

GTATGTGACT GATGAGAGCC AGGAGCTGAG AAAATCTATT GGGGGTTGAG AGGAGTGCCT    5941

GAGGAGGTAA TTATGGCAGT GAGATGAGGA TCTGCTCTTT GTTAGGGGGT GGGCTGAGGG    6001

TGGCAATCAA AGGCTTTAAC TTGCTTTTTC TGTTTTAG AG CCC TCA CCG TCT         6053
                                            Glu Pro Ser Pro Ser
                                                        300

GGC ACC CTA GTC ATT GGA GTC ATC AGT GGA ATT GCT GTT TTT GTC GTC     6101
Gly Thr Leu Val Ile Gly Val Ile Ser Gly Ile Ala Val Phe Val Val
            305                 310                 315

ATC TTG TTC ATT GGA ATT TTG TTC ATA ATA TTA AGG AAG AGG CAG GGT     6149
Ile Leu Phe Ile Gly Ile Leu Phe Ile Ile Leu Arg Lys Arg Gln Gly
        320                 325                 330
```

-continued

```
TCA A GTGAGTAGGA CAAGGGGGA AGTCTCTTAG TACCTCTGCC CCAGGGCACA        6203
Ser
335

GTGGGAAGAG GGGCAGAGGG GATCTGGCAT CCATGGGAAG CATTTTTCTC ATTTATATTC  6263

TTTGGGGACA CCAGCAGCTC CCTGGGAGAC AGAAAATAAT GGTTCTCCCC AGAATGAAAG  6323

TCTCTAATTC AACAAACATC TTCAGAGCAC CTACTATTTT GCAAGAGCTG TTTAAGGTAG  6383

TACAGGGGCT TTGAGGTTGA GAAGTCACTG TGGCTATTCT CAGAACCCAA ATCTGGTAGG  6443

GAATGAAATT GATAGCAAGT AAATGTAGTT AAAGAAGACC CCATGAGGTC CTAAAGCAGG  6503

CAGGAAGCAA ATGCTTAGGG TGTCAAAGGA AAGAATGATC ACATTCAGCT GGGGATCAAG  6563

ATAGCCTTCT GGATCTTGAA GGAGAAGCTG GATTCCATTA GGTGAGGTTG AAGATGATGG  6623

GAGGTCTACA CAGACGGAGC AACCATGCCA AGTAGGAGAG TATAAGGCAT ACTGGGAGAT  6683

TAGAAATAAT TACTGTACCT TAACCCTGAG TTTGCGTAGC TATCACTCAC CAATTATGCA  6743

TTTCTACCCC CTGAACATCT GTGGTGTAGG GAAAAGAGAA TCAGAAAGAA GCCAGCTCAT  6803

ACAGAGTCCA AGGGTCTTTT GGGATATTGG GTTATGATCA CTGGGGTGTC ATTGAAGGAT  6863

CCTAAGAAAG GAGGACCACG ATCTCCCTTA TATGGTGAAT GTGTTGTTAA GAAGTTAGAT  6923

GAGAGGTGAG GAGACCAGTT AGAAAGCCAA TAAGCATTTC CAGATGAGAG ATAATGGTTC  6983

TTGAAATCCA ATAGTGCCCA GGTCTAAATT GAGATGGGTG AATGAGGAAA ATAAGGAAGA  7043

GAGAAGAGGC AAGATGGTGC CTAGGTTTGT GATGCCTCTT TCCTGGGTCT CTTGTCTCCA  7103

CAG  GA GGA GCC ATG GGG CAC TAC GTC TTA GCT GAA CGT GAG            7144
     Arg Gly Ala Met Gly His Tyr Val Leu Ala Glu Arg Glu
                340                 345

TGACACGCAG CCTGCAGACT CACTGTGGGA AGGAGACAAA ACTAGAGACT CAAAGAGGGA  7204

GTGCATTTAT GAGCTCTTCA TGTTTCAGGA GAGAGTTGAA CCTAAACATA GAAATTGCCT  7264

GACGAACTCC TTGATTTTAG CCTTCTCTGT TCATTTCCTC AAAAAGATTT CCCCATTTAG  7324

GTTTCTGAGT TCCTGCATGC CGGTGATCCC TAGCTGTGAC CTCTCCCCTG GAACTGTCTC  7384

TCATGAACCT CAAGCTGCAT CTAGAGGCTT CCTTCATTTC CTCCGTCACC TCAGAGACAT  7444

ACACCTATGT CATTTCATTT CCTATTTTTG GAAGAGGACT CCTTAAATTT GGGGGACTTA  7504

CATGATTCAT TTTAACATCT GAGAAAAGCT TTGAACCCTG GGACGTGGCT AGTCATAACC  7564

TTACCAGATT TTTACACATG TATCTATGCA TTTTCTGGAC CCGTTCAACT TTTCCTTTGA  7624

ATCCTCTCTC TGTGTTACCC AGTAACTCAT CTGTCACCAA GCCTTGGGGA TTCTTCCATC  7684

TGATTGTGAT GTGAGTTGCA CAGCTATGAA GGCTGTACAC TGCACGAATG AAGAGGCAC   7744

CTGTCCCAGA AAAAGCATCA TGGCTATCTG TGGGTAGTAT GATGGGTGTT TTTAGCAGGT  7804

AGGAGGCAAA TATCTTGAAA GGGGTTGTGA AGAGGTGTTT TTTCTAATTG GCATGAAGGT  7864

GTCATACAGA TTTGCAAAGT TTAATGGTGC CTTCATTTGG GATGCTACTC TAGTATTCCA  7924

GACCTGAAGA ATCACAATAA TTTTCTACCT GGTCTCTCCT TGTTCTGATA ATGAAAATTA  7984

TGATAAGGAT GATAAAAGCA CTTACTTCGT GTCCGACTCT TCTGAGCACC TACTTACATG  8044

CATTACTGCA TGCACTTCTT ACAATAATTC TATGAGATAG GTACTATTAT CCCCATTTCT  8104

TTTTTAAATG AAGAAAGTGA AGTAGGCCGG GCACGGTGGC TCACGCCTGT AATCCCAGCA  8164

CTTTGGGAGG CCAAAGCGGG TGGATCACGA GGTCAGGAGA TCGAGACCAT CCTGGCTAAC  8224

ATGGTGAAAC CCCATCTCTA ATAAAAATAC AAAAAATTAG CTGGGCGTGG TGGCAGACGC  8284

CTGTAGTCCC AGCTACTCGG AAGGCTGAGG CAGGAGAATG GCATGAACCC AGGAGGCAGA  8344

GCTTGCAGTG AGCCGAGTTT GCGCCACTGC ACTCCAGCCT AGGTGACAGA GTGAGACTCC  8404
```

```
ATCTCAAAAA AATAAAAATA AAAATAAAAA AATGAAAAAA AAAGAAAGT GAAGTATAGA    8464

GTATCTCATA GTTTGTCAGT GATAGAAACA GGTTTCAAAC TCAGTCAATC TGACCGTTTG    8524

ATACATCTCA GACACCACTA CATTCAGTAG TTTAGATGCC TAGAATAAAT AGAGAAGGAA    8584

GGAGATGGCT CTTCTCTTGT CTCATTGTGT TTCTTCTGAG TGAGCTTGAA TCACATGAAG    8644

GGGAACAGCA GAAAACAACC AACTGATCCT CAGCTGTCAT GTTTCCTTTA AAAGTCCCTG    8704

AAGGAAGGTC CTGGAATGTG ACTCCCTTGC TCCTCTGTTG CTCTCTTTGG CATTCATTTC    8764

TTTGGACCCT ACGCAAGGAC TGTAATTGGT GGGGACAGCA GTGGCCCTG CTGGGCTTCA    8824

CACACGGTGT CCTCCCTAGG CCAGTGCCTC TGGAGTCAGA ACTCTGGTGG TATTTCCCTC    8884

AATGAAGTGG AGTAAGCTCT CTCATTTTGA GATGGTATAA TGGAAGCCAC CAAGTGGCTT    8944

AGAGGATGCC CAGGTCCTTC CATGGAGCCA CTGGGGTTCC GGTGCACATT AAAAAAAAAA    9004

TCTAACCAGG ACATTCAGGA ATTGCTAGAT TCTGGGAAAT CAGTTCACCA TGTTCAAAAG    9064

AGTCTTTTTT TTTTTTTTGA GACTCTATTG CCCAGGCTGG AGTGCAATGG CATGATCTCG    9124

GCTCACTGTA ACCTCTGCCT CCCAGGTTCA AGCGATTCTC CTGTCTCAGC CTCCCAAGTA    9184

GCTGGGATTA CAGGCGTGCA CCACCATGCC CGGCTAATTT TTGTATTTTT AGTAGAGACA    9244

GGGTTTCACC ATGTTGGCCA GGCTGGTCTC GAACTCTCCT GACCTCGTGA TCCGCCTGCC    9304

TCGGCCTCCC AAAGTGCTGA GATTACAGGT GTGAGCCACC CTGCCCAGCC GTCAAAAGAG    9364

TCTTAATATA TATATCCAGA TGGCATGTGT TTACTTTATG TTACTACATG CACTTGGCTG    9424

CATAAATGTG GTACAAGCAT TCTGTCTTGA AGGGCAGGTG CTTCAGGATA CCATATACAG    9484

CTCAGAAGTT TCTTCTTTAG GCATTAAATT TTAGCAAAGA TATCTCATCT CTTCTTTTAA    9544

ACCATTTTCT TTTTTTGTGG TTAGAAAAGT TATGTAGAAA AAAGTAAATG TGATTTACGC    9604

TCATTGTAGA AAAGCTATAA AATGAATACA ATTAAAGCTG TTATTTAATT AGCCAGTGAA    9664

AAACTATTAA CAACTTGTCT ATTACCTGTT AGTATTATTG TTGCATTAAA AATGCATATA    9724

CTTTAATAAA TGTATATTGT ATTGTATACT GCATGATTTT ATTGAAGTTC TTGTTCATCT    9784

TGTGTATATA CTTAATCGCT TTGTCATTTT GGAGACATTT ATTTTGCTTC TAATTTCTTT    9844

ACATTTGTC TTACGGAATA TTTTCATTCA ACTGTGGTAG CCGAATTAAT CGTGTTTCTT    9904

CACTCTAGGG ACATTGTCGT CTAAGTTGTA AGACATTGGT TATTTTACCA GCAAACCATT    9964

CTGAAAGCAT ATGACAAATT ATTTCTCTCT TAATATCTTA CTATACTGAA AGCAGACTGC   10024

TATAAGGCTT CACTTACTCT TCTACCTCAT AAGGAATATG TTACAATTAA TTTATTAGGT   10084

AAGCATTGT TTTATATTGG TTTTATTTCA CCTGGGCTGA GATTTCAAGA AACACCCCAG   10144

TCTTCACAGT AACACATTTC ACTAACACAT TTACTAAACA TCAGCAACTG TGGCCTGTTA   10204

ATTTTTTTAA TAGAAATTTT AAGTCCTCAT TTTCTTTCGG TGTTTTTTAA GCTTAATTTT   10264

TCTGGCTTTA TTCATAAATT CTTAAGGTCA ACTACATTTG AAAAATCAAA GACCTGCATT   10324

TTAAATTCTT ATTCACCTCT GGCAAAACCA TTCACAAACC ATGGTAGTAA AGAGAAGGGT   10384

GACACCTGGT GGCCATAGGT AAATGTACCA CGGTGGTCCG GTGACCAGAG ATGCAGCGCT   10444

GAGGGTTTTC CTGAAGGTAA AGGAATAAAG AATGGGTGGA GGGGCGTGCA CTGGAAATCA   10504

CTTGTAGAGA AAAGCCCCTG AAAATTTGAG AAAACAAACA AGAAACTACT TACCAGCTAT   10564

TTGAATTGCT GGAATCACAG GCCATTGCTG AGCTGCCTGA ACTGGGAACA CAACAGAAGG   10624

AAAACAAACC ACTCTGATAA TCATTGAGTC AAGTACAGCA GGTGATTGAG GACTGCTGAG   10684

AGGTACAGGC CAAAATTCTT ATGTTGTATT ATAATAATGT CATCTTATAA TACTGTCAGT   10744
```

```
ATTTTATAAA ACATTCTTCA CAAACTCACA CACATTTAAA AACAAAACAC TGTCTCTAAA    10804

ATCCCCAAAT TTTTCATAAA C                                              10825
```

(2) INFORMATION FOR SEQ ID NO:8:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
                20                  25                  30

Leu Phe Met Gly Ala Ser Glu Gln Asp Leu Gly Leu Ser Leu Phe Glu
         35                  40                  45

Ala Leu Gly Tyr Val Asp Asp Gln Leu Phe Val Phe Tyr Asp Asp Glu
     50                  55                  60

Ser Arg Arg Val Glu Pro Arg Thr Pro Trp Val Ser Ser Arg Ile Ser
 65                  70                  75                  80

Ser Gln Met Trp Leu Gln Leu Ser Gln Ser Leu Lys Gly Trp Asp His
                 85                  90                  95

Met Phe Thr Val Asp Phe Trp Thr Ile Met Glu Asn His Asn His Ser
             100                 105                 110

Lys Glu Ser His Thr Leu Gln Val Ile Leu Gly Cys Glu Met Gln Glu
         115                 120                 125

Asp Asn Ser Thr Glu Gly Tyr Trp Lys Tyr Gly Tyr Asp Gly Gln Asp
     130                 135                 140

His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
                165                 170                 175

Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Tyr Gln Val Glu His Pro Gly
        275                 280                 285

Leu Asp Gln Pro Leu Ile Val Ile Trp Glu Pro Ser Pro Ser Gly Thr
    290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335
```

```
Gly Ala Met Gly His Tyr Val Leu Ala Glu Arg Glu
            340                 345

(2) INFORMATION FOR SEQ ID NO:9:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 222..1268

(ix) FEATURE:
        (A) NAME/KEY: allele
        (B) LOCATION: replace(408, "c")
        (D) OTHER INFORMATION: /phenotype= "normal or wild-type
            (unaffected)"/label= 24d2

(ix) FEATURE:
        (A) NAME/KEY: allele
        (B) LOCATION: replace(414, "a")
        (D) OTHER INFORMATION: /phenotype= "normal or wild-type
            (unaffected)"/label= 24d7

(ix) FEATURE:
        (A) NAME/KEY: allele
        (B) LOCATION: replace(1066, "g")
        (D) OTHER INFORMATION: /phenotype= "normal or wild-type
            (unaffected)"/label= 24d1

(xi) SEQUENCE DESCRIPTION: SEQ ID NO:9:

GGGGACACTG GATCACCTAG TGTTTCACAA GCAGGTACCT TCTGCTGTAG GAGAGAGAGA      60

ACTAAAGTTC TGAAAGACCT GTTGCTTTTC ACCAGGAAGT TTTACTGGGC ATCTCCTGAG     120

CCTAGGCAAT AGCTGTAGGG TGACTTCTGG AGCCATCCCC GTTTCCCCGC CCCCCAAAAG     180

AAGCGGAGAT TTAACGGGGA CGTGCGGCCA GAGCTGGGGA A ATG GGC CCG CGA         233
                                             Met Gly Pro Arg
                                               1

GCC AGG CCG GCG CTT CTC CTC CTG ATG CTT TTG CAG ACC GCG GTC CTG       281
Ala Arg Pro Ala Leu Leu Leu Leu Met Leu Leu Gln Thr Ala Val Leu
  5              10                  15                  20

CAG GGG CGC TTG CTG CGT TCA CAC TCT CTG CAC TAC CTC TTC ATG GGT       329
Gln Gly Arg Leu Leu Arg Ser His Ser Leu His Tyr Leu Phe Met Gly
             25                  30                  35

GCC TCA GAG CAG GAC CTT GGT CTT TCC TTG TTT GAA GCT TTG GGC TAC       377
Ala Ser Glu Gln Asp Leu Gly Leu Ser Leu Phe Glu Ala Leu Gly Tyr
         40                  45                  50

GTG GAT GAC CAG CTG TTC GTG TTC TAT GAT CAT GAG AGT CGC CGT GTG       425
Val Asp Asp Gln Leu Phe Val Phe Tyr Asp His Glu Ser Arg Arg Val
     55                  60                  65

GAG CCC CGA ACT CCA TGG GTT TCC AGT AGA ATT TCA AGC CAG ATG TGG       473
Glu Pro Arg Thr Pro Trp Val Ser Ser Arg Ile Ser Ser Gln Met Trp
 70                  75                  80

CTG CAG CTG AGT CAG AGT CTG AAA GGG TGG GAT CAC ATG TTC ACT GTT       521
Leu Gln Leu Ser Gln Ser Leu Lys Gly Trp Asp His Met Phe Thr Val
 85                  90                  95                 100

GAC TTC TGG ACT ATT ATG GAA AAT CAC AAC CAC AGC AAG GAG TCC CAC       569
Asp Phe Trp Thr Ile Met Glu Asn His Asn His Ser Lys Glu Ser His
                105                 110                 115

ACC CTG CAG GTC ATC CTG GGC TGT GAA ATG CAA GAA GAC AAC AGT ACC       617
Thr Leu Gln Val Ile Leu Gly Cys Glu Met Gln Glu Asp Asn Ser Thr
            120                 125                 130
```

```
GAG GGC TAC TGG AAG TAC GGG TAT GAT GGG CAG GAC CAC CTT GAA TTC         665
Glu Gly Tyr Trp Lys Tyr Gly Tyr Asp Gly Gln Asp His Leu Glu Phe
            135                 140                 145

TGC CCT GAC ACA CTG GAT TGG AGA GCA GCA GAA CCC AGG GCC TGG CCC         713
Cys Pro Asp Thr Leu Asp Trp Arg Ala Ala Glu Pro Arg Ala Trp Pro
        150                 155                 160

ACC AAG CTG GAG TGG GAA AGG CAC AAG ATT CGG GCC AGG CAG AAC AGG         761
Thr Lys Leu Glu Trp Glu Arg His Lys Ile Arg Ala Arg Gln Asn Arg
165                 170                 175                 180

GCC TAC CTG GAG AGG GAC TGC CCT GCA CAG CTG CAG CAG TTG CTG GAG         809
Ala Tyr Leu Glu Arg Asp Cys Pro Ala Gln Leu Gln Gln Leu Leu Glu
                185                 190                 195

CTG GGG AGA GGT GTT TTG GAC CAA CAA GTG CCT CCT TTG GTG AAG GTG         857
Leu Gly Arg Gly Val Leu Asp Gln Gln Val Pro Pro Leu Val Lys Val
            200                 205                 210

ACA CAT CAT GTG ACC TCT TCA GTG ACC ACT CTA CGG TGT CGG GCC TTG         905
Thr His His Val Thr Ser Ser Val Thr Thr Leu Arg Cys Arg Ala Leu
        215                 220                 225

AAC TAC TAC CCC CAG AAC ATC ACC ATG AAG TGG CTG AAG GAT AAG CAG         953
Asn Tyr Tyr Pro Gln Asn Ile Thr Met Lys Trp Leu Lys Asp Lys Gln
230                 235                 240

CCA ATG GAT GCC AAG GAG TTC GAA CCT AAA GAC GTA TTG CCC AAT GGG        1001
Pro Met Asp Ala Lys Glu Phe Glu Pro Lys Asp Val Leu Pro Asn Gly
245                 250                 255                 260

GAT GGG ACC TAC CAG GGC TGG ATA ACC TTG GCT GTA CCC CCT GGG GAA        1049
Asp Gly Thr Tyr Gln Gly Trp Ile Thr Leu Ala Val Pro Pro Gly Glu
                265                 270                 275

GAG CAG AGA TAT ACG TGC CAG GTG GAG CAC CCA GGC CTG GAT CAG CCC        1097
Glu Gln Arg Tyr Thr Cys Gln Val Glu His Pro Gly Leu Asp Gln Pro
            280                 285                 290

CTC ATT GTG ATC TGG GAG CCC TCA CCG TCT GGC ACC CTA GTC ATT GGA        1145
Leu Ile Val Ile Trp Glu Pro Ser Pro Ser Gly Thr Leu Val Ile Gly
        295                 300                 305

GTC ATC AGT GGA ATT GCT GTT TTT GTC GTC ATC TTG TTC ATT GGA ATT        1193
Val Ile Ser Gly Ile Ala Val Phe Val Val Ile Leu Phe Ile Gly Ile
310                 315                 320

TTG TTC ATA ATA TTA AGG AAG AGG CAG GGT TCA AGA GGA GCC ATG GGG        1241
Leu Phe Ile Ile Leu Arg Lys Arg Gln Gly Ser Arg Gly Ala Met Gly
325                 330                 335                 340

CAC TAC GTC TTA GCT GAA CGT GAG TGACACGCAG CCTGCAGACT CACTGTGGGA       1295
His Tyr Val Leu Ala Glu Arg Glu
                345

AGGAGACAAA ACTAGAGACT CAAAGAGGGA GTGCATTTAT GAGCTCTTCA TGTTTCAGGA      1355

GAGAGTTGAA CCTAAACATA GAAATTGCCT GACGAACTCC TTGATTTTAG CCTTCTCTGT      1415

TCATTTCCTC AAAAAGATTT CCCCA                                           1440

(2) INFORMATION FOR SEQ ID NO:10:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 222..1268

(ix) FEATURE:
```

(A) NAME/KEY: allele
        (B) LOCATION: replace(1066, "a")
        (D) OTHER INFORMATION: /phenotype= "Hereditary Hemochromatosis
            (HH)"/label= 24d1

(xi) SEQUENCE DESCRIPTION: SEQ ID NO:10:

```
GGGGACACTG GATCACCTAG TGTTTCACAA GCAGGTACCT TCTGCTGTAG GAGAGAGAGA          60

ACTAAAGTTC TGAAAGACCT GTTGCTTTTC ACCAGGAAGT TTTACTGGGC ATCTCCTGAG         120

CCTAGGCAAT AGCTGTAGGG TGACTTCTGG AGCCATCCCC GTTTCCCCGC CCCCCAAAAG         180

AAGCGGAGAT TTAACGGGGA CGTGCGGCCA GAGCTGGGGA A ATG GGC CCG CGA             233
                                             Met Gly Pro Arg
                                              1

GCC AGG CCG GCG CTT CTC CTC CTG ATG CTT TTG CAG ACC GCG GTC CTG          281
Ala Arg Pro Ala Leu Leu Leu Leu Met Leu Leu Gln Thr Ala Val Leu
 5              10                  15                  20

CAG GGG CGC TTG CTG CGT TCA CAC TCT CTG CAC TAC CTC TTC ATG GGT          329
Gln Gly Arg Leu Leu Arg Ser His Ser Leu His Tyr Leu Phe Met Gly
            25                  30                  35

GCC TCA GAG CAG GAC CTT GGT CTT TCC TTG TTT GAA GCT TTG GGC TAC          377
Ala Ser Glu Gln Asp Leu Gly Leu Ser Leu Phe Glu Ala Leu Gly Tyr
         40                  45                  50

GTG GAT GAC CAG CTG TTC GTG TTC TAT GAT CAT GAG AGT CGC CGT GTG          425
Val Asp Asp Gln Leu Phe Val Phe Tyr Asp His Glu Ser Arg Arg Val
     55                  60                  65

GAG CCC CGA ACT CCA TGG GTT TCC AGT AGA ATT TCA AGC CAG ATG TGG          473
Glu Pro Arg Thr Pro Trp Val Ser Ser Arg Ile Ser Ser Gln Met Trp
 70                  75                  80

CTG CAG CTG AGT CAG AGT CTG AAA GGG TGG GAT CAC ATG TTC ACT GTT          521
Leu Gln Leu Ser Gln Ser Leu Lys Gly Trp Asp His Met Phe Thr Val
 85                  90                  95                 100

GAC TTC TGG ACT ATT ATG GAA AAT CAC AAC CAC AGC AAG GAG TCC CAC          569
Asp Phe Trp Thr Ile Met Glu Asn His Asn His Ser Lys Glu Ser His
                105                 110                 115

ACC CTG CAG GTC ATC CTG GGC TGT GAA ATG CAA GAA GAC AAC AGT ACC          617
Thr Leu Gln Val Ile Leu Gly Cys Glu Met Gln Glu Asp Asn Ser Thr
            120                 125                 130

GAG GGC TAC TGG AAG TAC GGG TAT GAT GGG CAG GAC CAC CTT GAA TTC          665
Glu Gly Tyr Trp Lys Tyr Gly Tyr Asp Gly Gln Asp His Leu Glu Phe
        135                 140                 145

TGC CCT GAC ACA CTG GAT TGG AGA GCA GCA GAA CCC AGG GCC TGG CCC          713
Cys Pro Asp Thr Leu Asp Trp Arg Ala Ala Glu Pro Arg Ala Trp Pro
150                 155                 160

ACC AAG CTG GAG TGG GAA AGG CAC AAG ATT CGG GCC AGG CAG AAC AGG          761
Thr Lys Leu Glu Trp Glu Arg His Lys Ile Arg Ala Arg Gln Asn Arg
165                 170                 175                 180

GCC TAC CTG GAG AGG GAC TGC CCT GCA CAG CTG CAG CAG TTG CTG GAG          809
Ala Tyr Leu Glu Arg Asp Cys Pro Ala Gln Leu Gln Gln Leu Leu Glu
                185                 190                 195

CTG GGG AGA GGT GTT TTG GAC CAA CAA GTG CCT CCT TTG GTG AAG GTG          857
Leu Gly Arg Gly Val Leu Asp Gln Gln Val Pro Pro Leu Val Lys Val
            200                 205                 210

ACA CAT CAT GTG ACC TCT TCA GTG ACC ACT CTA CGG TGT CGG GCC TTG          905
Thr His His Val Thr Ser Ser Val Thr Thr Leu Arg Cys Arg Ala Leu
        215                 220                 225

AAC TAC TAC CCC CAG AAC ATC ACC ATG AAG TGG CTG AAG GAT AAG CAG          953
Asn Tyr Tyr Pro Gln Asn Ile Thr Met Lys Trp Leu Lys Asp Lys Gln
    230                 235                 240

CCA ATG GAT GCC AAG GAG TTC GAA CCT AAA GAC GTA TTG CCC AAT GGG         1001
Pro Met Asp Ala Lys Glu Phe Glu Pro Lys Asp Val Leu Pro Asn Gly
```

```
245                 250                 255                 260
GAT GGG ACC TAC CAG GGC TGG ATA ACC TTG GCT GTA CCC CCT GGG GAA    1049
Asp Gly Thr Tyr Gln Gly Trp Ile Thr Leu Ala Val Pro Pro Gly Glu
                265                 270                 275

GAG CAG AGA TAT ACG TAC CAG GTG GAG CAC CCA GGC CTG GAT CAG CCC    1097
Glu Gln Arg Tyr Thr Tyr Gln Val Glu His Pro Gly Leu Asp Gln Pro
            280                 285                 290

CTC ATT GTG ATC TGG GAG CCC TCA CCG TCT GGC ACC CTA GTC ATT GGA    1145
Leu Ile Val Ile Trp Glu Pro Ser Pro Ser Gly Thr Leu Val Ile Gly
        295                 300                 305

GTC ATC AGT GGA ATT GCT GTT TTT GTC GTC ATC TTG TTC ATT GGA ATT    1193
Val Ile Ser Gly Ile Ala Val Phe Val Val Ile Leu Phe Ile Gly Ile
    310                 315                 320

TTG TTC ATA ATA TTA AGG AAG AGG CAG GGT TCA AGA GGA GCC ATG GGG    1241
Leu Phe Ile Ile Leu Arg Lys Arg Gln Gly Ser Arg Gly Ala Met Gly
325                 330                 335                 340

CAC TAC GTC TTA GCT GAA CGT GAG TGACACGCAG CCTGCAGACT CACTGTGGGA   1295
His Tyr Val Leu Ala Glu Arg Glu
                345

AGGAGACAAA ACTAGAGACT CAAAGAGGGA GTGCATTTAT GAGCTCTTCA TGTTTCAGGA  1355

GAGAGTTGAA CCTAAACATA GAAATTGCCT GACGAACTCC TTGATTTTAG CCTTCTCTGT  1415

TCATTTCCTC AAAAAGATTT CCCCA                                       1440

(2) INFORMATION FOR SEQ ID NO:11:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 222..1268

(ix) FEATURE:
        (A) NAME/KEY: allele
        (B) LOCATION: replace(408, "g")
        (D) OTHER INFORMATION: /phenotype= "Hereditary Hemochromatosis
            (HH)"/label= 24d2

(xi) SEQUENCE DESCRIPTION: SEQ ID NO:11:

GGGGACACTG GATCACCTAG TGTTTCACAA GCAGGTACCT TCTGCTGTAG GAGAGAGAGA    60

ACTAAAGTTC TGAAAGACCT GTTGCTTTTC ACCAGGAAGT TTTACTGGGC ATCTCCTGAG   120

CCTAGGCAAT AGCTGTAGGG TGACTTCTGG AGCCATCCCC GTTTCCCCGC CCCCCAAAAG   180

AAGCGGAGAT TTAACGGGGA CGTGCGGCCA GAGCTGGGGA A ATG GGC CCG CGA       233
                                             Met Gly Pro Arg
                                               1

GCC AGG CCG GCG CTT CTC CTC CTG ATG CTT TTG CAG ACC GCG GTC CTG    281
Ala Arg Pro Ala Leu Leu Leu Leu Met Leu Leu Gln Thr Ala Val Leu
    5                   10                  15                  20

CAG GGG CGC TTG CTG CGT TCA CAC TCT CTG CAC TAC CTC TTC ATG GGT    329
Gln Gly Arg Leu Leu Arg Ser His Ser Leu His Tyr Leu Phe Met Gly
                25                  30                  35

GCC TCA GAG CAG GAC CTT GGT CTT TCC TTG TTT GAA GCT TTG GGC TAC    377
Ala Ser Glu Gln Asp Leu Gly Leu Ser Leu Phe Glu Ala Leu Gly Tyr
            40                  45                  50

GTG GAT GAC CAG CTG TTC GTG TTC TAT GAT GAT GAG AGT CGC CGT GTG    425
Val Asp Asp Gln Leu Phe Val Phe Tyr Asp Asp Glu Ser Arg Arg Val
```

```
              55                  60                  65
GAG CCC CGA ACT CCA TGG GTT TCC AGT AGA ATT TCA AGC CAG ATG TGG              473
Glu Pro Arg Thr Pro Trp Val Ser Ser Arg Ile Ser Ser Gln Met Trp
         70                  75                  80

CTG CAG CTG AGT CAG AGT CTG AAA GGG TGG GAT CAC ATG TTC ACT GTT              521
Leu Gln Leu Ser Gln Ser Leu Lys Gly Trp Asp His Met Phe Thr Val
85                  90                  95                  100

GAC TTC TGG ACT ATT ATG GAA AAT CAC AAC CAC AGC AAG GAG TCC CAC              569
Asp Phe Trp Thr Ile Met Glu Asn His Asn His Ser Lys Glu Ser His
                 105                 110                 115

ACC CTG CAG GTC ATC CTG GGC TGT GAA ATG CAA GAA GAC AAC AGT ACC              617
Thr Leu Gln Val Ile Leu Gly Cys Glu Met Gln Glu Asp Asn Ser Thr
             120                 125                 130

GAG GGC TAC TGG AAG TAC GGG TAT GAT GGG CAG GAC CAC CTT GAA TTC              665
Glu Gly Tyr Trp Lys Tyr Gly Tyr Asp Gly Gln Asp His Leu Glu Phe
             135                 140                 145

TGC CCT GAC ACA CTG GAT TGG AGA GCA GCA GAA CCC AGG GCC TGG CCC              713
Cys Pro Asp Thr Leu Asp Trp Arg Ala Ala Glu Pro Arg Ala Trp Pro
         150                 155                 160

ACC AAG CTG GAG TGG GAA AGG CAC AAG ATT CGG GCC AGG CAG AAC AGG              761
Thr Lys Leu Glu Trp Glu Arg His Lys Ile Arg Ala Arg Gln Asn Arg
165                 170                 175                 180

GCC TAC CTG GAG AGG GAC TGC CCT GCA CAG CTG CAG CAG TTG CTG GAG              809
Ala Tyr Leu Glu Arg Asp Cys Pro Ala Gln Leu Gln Gln Leu Leu Glu
                 185                 190                 195

CTG GGG AGA GGT GTT TTG GAC CAA CAA GTG CCT CCT TTG GTG AAG GTG              857
Leu Gly Arg Gly Val Leu Asp Gln Gln Val Pro Pro Leu Val Lys Val
             200                 205                 210

ACA CAT CAT GTG ACC TCT TCA GTG ACC ACT CTA CGG TGT CGG GCC TTG              905
Thr His His Val Thr Ser Ser Val Thr Thr Leu Arg Cys Arg Ala Leu
             215                 220                 225

AAC TAC TAC CCC CAG AAC ATC ACC ATG AAG TGG CTG AAG GAT AAG CAG              953
Asn Tyr Tyr Pro Gln Asn Ile Thr Met Lys Trp Leu Lys Asp Lys Gln
         230                 235                 240

CCA ATG GAT GCC AAG GAG TTC GAA CCT AAA GAC GTA TTG CCC AAT GGG             1001
Pro Met Asp Ala Lys Glu Phe Glu Pro Lys Asp Val Leu Pro Asn Gly
245                 250                 255                 260

GAT GGG ACC TAC CAG GGC TGG ATA ACC TTG GCT GTA CCC CCT GGG GAA             1049
Asp Gly Thr Tyr Gln Gly Trp Ile Thr Leu Ala Val Pro Pro Gly Glu
                 265                 270                 275

GAG CAG AGA TAT ACG TGC CAG GTG GAG CAC CCA GGC CTG GAT CAG CCC             1097
Glu Gln Arg Tyr Thr Cys Gln Val Glu His Pro Gly Leu Asp Gln Pro
             280                 285                 290

CTC ATT GTG ATC TGG GAG CCC TCA CCG TCT GGC ACC CTA GTC ATT GGA             1145
Leu Ile Val Ile Trp Glu Pro Ser Pro Ser Gly Thr Leu Val Ile Gly
             295                 300                 305

GTC ATC AGT GGA ATT GCT GTT TTT GTC GTC ATC TTG TTC ATT GGA ATT             1193
Val Ile Ser Gly Ile Ala Val Phe Val Val Ile Leu Phe Ile Gly Ile
             310                 315                 320

TTG TTC ATA ATA TTA AGG AAG AGG CAG GGT TCA AGA GGA GCC ATG GGG             1241
Leu Phe Ile Ile Leu Arg Lys Arg Gln Gly Ser Arg Gly Ala Met Gly
325                 330                 335                 340

CAC TAC GTC TTA GCT GAA CGT GAG TGACACGCAG CCTGCAGACT CACTGTGGGA             1295
His Tyr Val Leu Ala Glu Arg Glu
                 345

AGGAGACAAA ACTAGAGACT CAAAGAGGGA GTGCATTTAT GAGCTCTTCA TGTTTCAGGA            1355

GAGAGTTGAA CCTAAACATA GAAATTGCCT GACGAACTCC TTGATTTTAG CCTTCTCTGT            1415

TCATTTCCTC AAAAAGATTT CCCCA                                                   1440
```

(2) INFORMATION FOR SEQ ID NO:12:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 222..1268

(ix) FEATURE:
        (A) NAME/KEY: allele
        (B) LOCATION: replace(408, "g")
        (D) OTHER INFORMATION: /phenotype= "Hereditary Hemochromatosis
        (HH)"/label= 24d2

(ix) FEATURE:
        (A) NAME/KEY: allele
        (B) LOCATION: replace(1066, "a")
        (D) OTHER INFORMATION: /phenotype= "Hereditary Hemochromatosis
        (HH)"/label= 24d1

(xi) SEQUENCE DESCRIPTION: SEQ ID NO:12:

```
GGGGACACTG GATCACCTAG TGTTTCACAA GCAGGTACCT TCTGCTGTAG GAGAGAGAGA      60

ACTAAAGTTC TGAAAGACCT GTTGCTTTTC ACCAGGAAGT TTTACTGGGC ATCTCCTGAG     120

CCTAGGCAAT AGCTGTAGGG TGACTTCTGG AGCCATCCCC GTTTCCCCGC CCCCCAAAAG     180

AAGCGGAGAT TTAACGGGGA CGTGCGGCCA GAGCTGGGGA A ATG GGC CCG CGA         233
                                             Met Gly Pro Arg
                                              1

GCC AGG CCG GCG CTT CTC CTC CTG ATG CTT TTG CAG ACC GCG GTC CTG       281
Ala Arg Pro Ala Leu Leu Leu Leu Met Leu Leu Gln Thr Ala Val Leu
 5              10                  15                  20

CAG GGG CGC TTG CTG CGT TCA CAC TCT CTG CAC TAC CTC TTC ATG GGT       329
Gln Gly Arg Leu Leu Arg Ser His Ser Leu His Tyr Leu Phe Met Gly
             25                  30                  35

GCC TCA GAG CAG GAC CTT GGT CTT TCC TTG TTT GAA GCT TTG GGC TAC       377
Ala Ser Glu Gln Asp Leu Gly Leu Ser Leu Phe Glu Ala Leu Gly Tyr
         40                  45                  50

GTG GAT GAC CAG CTG TTC GTG TTC TAT GAT GAT GAG AGT CGC CGT GTG       425
Val Asp Asp Gln Leu Phe Val Phe Tyr Asp Asp Glu Ser Arg Arg Val
     55                  60                  65

GAG CCC CGA ACT CCA TGG GTT TCC AGT AGA ATT TCA AGC CAG ATG TGG       473
Glu Pro Arg Thr Pro Trp Val Ser Ser Arg Ile Ser Ser Gln Met Trp
 70                  75                  80

CTG CAG CTG AGT CAG AGT CTG AAA GGG TGG GAT CAC ATG TTC ACT GTT       521
Leu Gln Leu Ser Gln Ser Leu Lys Gly Trp Asp His Met Phe Thr Val
 85              90                  95                  100

GAC TTC TGG ACT ATT ATG GAA AAT CAC AAC CAC AGC AAG GAG TCC CAC       569
Asp Phe Trp Thr Ile Met Glu Asn His Asn His Ser Lys Glu Ser His
                 105                 110                 115

ACC CTG CAG GTC ATC CTG GGC TGT GAA ATG CAA GAA GAC AAC AGT ACC       617
Thr Leu Gln Val Ile Leu Gly Cys Glu Met Gln Glu Asp Asn Ser Thr
             120                 125                 130

GAG GGC TAC TGG AAG TAC GGG TAT GAT GGG CAG GAC CAC CTT GAA TTC       665
Glu Gly Tyr Trp Lys Tyr Gly Tyr Asp Gly Gln Asp His Leu Glu Phe
         135                 140                 145

TGC CCT GAC ACA CTG GAT TGG AGA GCA GCA GAA CCC AGG GCC TGG CCC       713
Cys Pro Asp Thr Leu Asp Trp Arg Ala Ala Glu Pro Arg Ala Trp Pro
    150                  155                 160
```

```
ACC AAG CTG GAG TGG GAA AGG CAC AAG ATT CGG GCC AGG CAG AAC AGG      761
Thr Lys Leu Glu Trp Glu Arg His Lys Ile Arg Ala Arg Gln Asn Arg
165                 170                 175                 180

GCC TAC CTG GAG AGG GAC TGC CCT GCA CAG CTG CAG CAG TTG CTG GAG      809
Ala Tyr Leu Glu Arg Asp Cys Pro Ala Gln Leu Gln Gln Leu Leu Glu
                185                 190                 195

CTG GGG AGA GGT GTT TTG GAC CAA CAA GTG CCT CCT TTG GTG AAG GTG      857
Leu Gly Arg Gly Val Leu Asp Gln Gln Val Pro Pro Leu Val Lys Val
            200                 205                 210

ACA CAT CAT GTG ACC TCT TCA GTG ACC ACT CTA CGG TGT CGG GCC TTG      905
Thr His His Val Thr Ser Ser Val Thr Thr Leu Arg Cys Arg Ala Leu
            215                 220                 225

AAC TAC TAC CCC CAG AAC ATC ACC ATG AAG TGG CTG AAG GAT AAG CAG      953
Asn Tyr Tyr Pro Gln Asn Ile Thr Met Lys Trp Leu Lys Asp Lys Gln
230                 235                 240

CCA ATG GAT GCC AAG GAG TTC GAA CCT AAA GAC GTA TTG CCC AAT GGG     1001
Pro Met Asp Ala Lys Glu Phe Glu Pro Lys Asp Val Leu Pro Asn Gly
245                 250                 255                 260

GAT GGG ACC TAC CAG GGC TGG ATA ACC TTG GCT GTA CCC CCT GGG GAA     1049
Asp Gly Thr Tyr Gln Gly Trp Ile Thr Leu Ala Val Pro Pro Gly Glu
                265                 270                 275

GAG CAG AGA TAT ACG TAC CAG GTG GAG CAC CCA GGC CTG GAT CAG CCC     1097
Glu Gln Arg Tyr Thr Tyr Gln Val Glu His Pro Gly Leu Asp Gln Pro
            280                 285                 290

CTC ATT GTG ATC TGG GAG CCC TCA CCG TCT GGC ACC CTA GTC ATT GGA     1145
Leu Ile Val Ile Trp Glu Pro Ser Pro Ser Gly Thr Leu Val Ile Gly
            295                 300                 305

GTC ATC AGT GGA ATT GCT GTT TTT GTC GTC ATC TTG TTC ATT GGA ATT     1193
Val Ile Ser Gly Ile Ala Val Phe Val Val Ile Leu Phe Ile Gly Ile
310                 315                 320

TTG TTC ATA ATA TTA AGG AAG AGG CAG GGT TCA AGA GGA GCC ATG GGG     1241
Leu Phe Ile Ile Leu Arg Lys Arg Gln Gly Ser Arg Gly Ala Met Gly
325                 330                 335                 340

CAC TAC GTC TTA GCT GAA CGT GAG TGACACGCAG CCTGCAGACT CACTGTGGGA    1295
His Tyr Val Leu Ala Glu Arg Glu
                345

AGGAGACAAA ACTAGAGACT CAAAGAGGGA GTGCATTTAT GAGCTCTTCA TGTTTCAGGA   1355

GAGAGTTGAA CCTAAACATA GAAATTGCCT GACGAACTCC TTGATTTTAG CCTTCTCTGT   1415

TCATTTCCTC AAAAAGATTT CCCCA                                        1440

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

TGGCAAGGGT AAACAGATCC                                                20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:14:

CTCAGGCACT CCTCTCAACC                                                        20

(2) INFORMATION FOR SEQ ID NO:15:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = 5'-biotinylated guanine (bio-G)"

(xi) SEQUENCE DESCRIPTION: SEQ ID NO:15:

NGAAGAGCAG AGATATACGT G                                                      21

(2) INFORMATION FOR SEQ ID NO:16:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = 5'-biotinylated guanine (bio-G)"

(xi) SEQUENCE DESCRIPTION: SEQ ID NO:16:

NGAAGAGCAG AGATATACGT A                                                      21

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = 5'-phosphorylated cytosine (p-C)"

(ix) FEATURE:
            (A) NAME/KEY: modified_base
            (B) LOCATION: 18
            (D) OTHER INFORMATION: /mod_base= OTHER
                /note= "N = 3'-digoxigenin-conjugated guanine (G-dig)"

(xi) SEQUENCE DESCRIPTION: SEQ ID NO:17:

NCAGGTGGAG CACCCAGN                                                          18

(2) INFORMATION FOR SEQ ID NO:18:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

CTGAAAGGGT GGGATCACAT                                                20

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

CAAGGAGTTC GTCAGGCAAT                                                20

(2) INFORMATION FOR SEQ ID NO:20:

(i) SEQUENCE CHARACTERISTICS:
            (A) LENGTH: 517 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..517
            (D) OTHER INFORMATION: /note= "normal or wild-type (unaffected)
                genomic sequence surrounding variant for
                24d1(G) allele corresponding to positions
                5507-6023 of genomic sequence containing
                the HH gene (SEQ ID NO:1)"

(ix) FEATURE:
            (A) NAME/KEY: allele
            (B) LOCATION: replace(328, "g")
            (D) OTHER INFORMATION: /phenotype= "normal or wild-type
                (unaffected)"/label= 24d1

(xi) SEQUENCE DESCRIPTION: SEQ ID NO:20:

TATTTCCTTC CTCCAACCTA TAGAAGGAAG TGAAAGTTCC AGTCTTCCTG GCAAGGGTAA      60

ACAGATCCCC TCTCCTCATC CTTCCTCTTT CCTGTCAAGT GCCTCCTTTG GTGAAGGTGA     120

CACATCATGT GACCTCTTCA GTGACCACTC TACGGTGTCG GGCCTTGAAC TACTACCCCC     180

AGAACATCAC CATGAAGTGG CTGAAGGATA AGCAGCCAAT GGATGCCAAG GAGTTCGAAC     240

CTAAAGACGT ATTGCCCAAT GGGGATGGGA CCTACCAGGG CTGGATAACC TTGGCTGTAC     300

CCCCTGGGGA AGAGCAGAGA TATACGTGCC AGGTGGAGCA CCCAGGCCTG GATCAGCCCC     360

TCATTGTGAT CTGGGGTATG TGACTGATGA GAGCCAGGAG CTGAGAAAAT CTATTGGGGG     420

TTGAGAGGAG TGCCTGAGGA GGTAATTATG GCAGTGAGAT GAGGATCTGC TCTTTGTTAG     480

GGGGTGGGCT GAGGGTGGCA ATCAAAGGCT TTAACTT                              517

(2) INFORMATION FOR SEQ ID NO:21:

(i) SEQUENCE CHARACTERISTICS:
            (A) LENGTH: 517 base pairs
            (B) TYPE: nucleic acid
            (C) STRANDEDNESS: single -continued

```
        (D) TOPOLOGY: linear (ii) MOLECULE TYPE: DNA (genomic)

(ix) FEATURE:
        (A) NAME/KEY: -
        (B) LOCATION: 1..517
        (D) OTHER INFORMATION: /note= "genomic sequence surrounding
            variant for 24d1(A) allele corresponding
            to positions 5507-6023 of genomic
            sequence containing the HH gene (SEQ ID NO:3)"

(ix) FEATURE:
        (A) NAME/KEY: allele
        (B) LOCATION: replace(328, "a")
        (D) OTHER INFORMATION: /phenotype= "Hereditary Hemochromatosis
        (HH)"/label= 24d1

(xi) SEQUENCE DESCRIPTION: SEQ ID NO:21:

TATTTCCTTC CTCCAACCTA TAGAAGGAAG TGAAAGTTCC AGTCTTCCTG GCAAGGGTAA      60

ACAGATCCCC TCTCCTCATC CTTCCTCTTT CCTGTCAAGT GCCTCCTTTG GTGAAGGTGA    120

CACATCATGT GACCTCTTCA GTGACCACTC TACGGTGTCG GGCCTTGAAC TACTACCCCC    180

AGAACATCAC CATGAAGTGG CTGAAGGATA AGCAGCCAAT GGATGCCAAG GAGTTCGAAC    240

CTAAAGACGT ATTGCCCAAT GGGGATGGGA CCTACCAGGG CTGGATAACC TTGGCTGTAC    300

CCCCTGGGGA AGAGCAGAGA TATACGTACC AGGTGGAGCA CCCAGGCCTG GATCAGCCCC    360

TCATTGTGAT CTGGGGTATG TGACTGATGA GAGCCAGGAG CTGAGAAAAT CTATTGGGGG    420

TTGAGAGGAG TGCCTGAGGA GGTAATTATG GCAGTGAGAT GAGGATCTGC TCTTTGTTAG    480

GGGGTGGGCT GAGGGTGGCA ATCAAAGGCT TTAACTT                             517

(2) INFORMATION FOR SEQ ID NO:22:

(i) SEQUENCE CHARACTERISTICS:
        (A) LENGTH: 361 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..361
        (D) OTHER INFORMATION: /note= "Rabbit leukocyte antigen (RLA)"

(xi) SEQUENCE DESCRIPTION: SEQ ID NO:22:

Met Gly Ser Ile Pro Pro Arg Thr Leu Leu Leu Leu Ala Gly Ala
1               5                  10                  15

Leu Thr Leu Lys Asp Thr Gln Ala Gly Ser His Ser Met Arg Tyr Phe
            20                  25                  30

Tyr Thr Ser Val Ser Arg Pro Gly Leu Gly Glu Pro Arg Phe Ile Ile
        35                  40                  45

Val Gly Tyr Val Asp Asp Thr Gln Phe Val Arg Phe Asp Ser Asp Ala
    50                  55                  60

Ala Ser Pro Arg Met Glu Gln Arg Ala Pro Trp Met Gly Gln Val Glu
65                  70                  75                  80

Pro Glu Tyr Trp Asp Gln Gln Thr Gln Ile Ala Lys Asp Thr Ala Gln
                85                  90                  95

Thr Phe Arg Val Asn Leu Asn Thr Ala Leu Arg Tyr Tyr Asn Gln Ser
            100                 105                 110

Ala Ala Gly Ser His Thr Phe Gln Thr Met Phe Gly Cys Glu Val Trp
        115                 120                 125
```

```
Ala Asp Gly Arg Phe Phe His Gly Tyr Arg Gln Tyr Ala Tyr Asp Gly
        130                 135                 140

Ala Asp Tyr Ile Ala Leu Asn Glu Asp Leu Arg Ser Trp Thr Ala Ala
145                 150                 155                 160

Asp Thr Ala Ala Gln Asn Thr Gln Arg Lys Trp Glu Ala Ala Gly Glu
                165                 170                 175

Ala Glu Arg His Arg Ala Tyr Leu Glu Arg Glu Cys Val Glu Trp Leu
            180                 185                 190

Arg Arg Tyr Leu Glu Met Gly Lys Glu Thr Leu Gln Arg Ala Asp Pro
        195                 200                 205

Pro Lys Ala His Val Thr His His Pro Ala Ser Asp Arg Glu Ala Thr
    210                 215                 220

Leu Arg Cys Trp Ala Leu Gly Phe Tyr Pro Ala Glu Ile Ser Leu Thr
225                 230                 235                 240

Trp Gln Arg Asp Gly Glu Asp Gln Thr Gln Asp Thr Glu Leu Val Glu
                245                 250                 255

Thr Arg Pro Gly Gly Asp Gly Thr Phe Gln Lys Trp Ala Ala Val Val
            260                 265                 270

Val Pro Ser Gly Glu Glu Gln Arg Tyr Thr Cys Arg Val Gln His Glu
        275                 280                 285

Gly Leu Pro Glu Pro Leu Thr Leu Thr Trp Glu Pro Pro Ala Gln Pro
    290                 295                 300

Thr Ala Leu Ile Val Gly Ile Val Ala Gly Val Leu Gly Val Leu Leu
305                 310                 315                 320

Ile Leu Gly Ala Val Val Ala Val Val Arg Arg Lys Lys His Ser Ser
                325                 330                 335

Asp Gly Lys Gly Gly Arg Tyr Thr Pro Ala Ala Gly Gly His Arg Asp
            340                 345                 350

Gln Gly Ser Asp Asp Ser Leu Met Pro
        355                 360

(2) INFORMATION FOR SEQ ID NO:23:

(i) SEQUENCE CHARACTERISTICS:
        (A) LENGTH: 365 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..365
        (D) OTHER INFORMATION: /note= "Human Major Histocompatability
            Class I (MHC) protein"

(xi) SEQUENCE DESCRIPTION: SEQ ID NO:23:

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80
```

```
Pro Glu Tyr Trp Asp Gly Glu Thr Arg Lys Val Lys Ala His Ser Gln
                85                  90                  95
Thr His Arg Val Asp Leu Gly Thr Leu Arg Gly Tyr Tyr Asn Gln Ser
            100                 105                 110
Glu Ala Gly Ser His Thr Leu Gln Met Met Phe Gly Cys Asp Val Gly
        115                 120                 125
Ser Asp Trp Arg Phe Leu Arg Gly Tyr His Gln Tyr Ala Tyr Asp Gly
    130                 135                 140
Lys Asp Tyr Ile Ala Leu Lys Glu Asp Leu Arg Ser Trp Thr Ala Ala
145                 150                 155                 160
Asp Met Ala Ala Gln Thr Thr Lys His Lys Trp Glu Ala Ala His Val
                165                 170                 175
Ala Glu Gln Leu Arg Ala Tyr Leu Glu Gly Thr Cys Val Glu Trp Leu
            180                 185                 190
Arg Arg Tyr Leu Glu Asn Gly Lys Glu Thr Leu Gln Arg Thr Asp Ala
        195                 200                 205
Pro Lys Thr His Met Thr His His Ala Val Ser Asp His Glu Ala Thr
    210                 215                 220
Leu Arg Cys Trp Ala Leu Ser Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Gly Thr Phe Gln Lys Trp Ala Ala Val Val
            260                 265                 270
Val Pro Ser Gly Gln Glu Gln Arg Tyr Thr Cys His Val Gln His Glu
        275                 280                 285
Gly Leu Pro Lys Pro Leu Thr Leu Arg Trp Glu Pro Ser Ser Gln Pro
    290                 295                 300
Thr Ile Pro Ile Val Gly Ile Ile Ala Gly Leu Val Leu Phe Gly Ala
305                 310                 315                 320
Val Ile Thr Gly Ala Val Val Ala Ala Val Met Trp Arg Arg Lys Ser
                325                 330                 335
Ser Asp Arg Lys Gly Gly Ser Tyr Ser Gln Ala Ala Ser Ser Asp Ser
            340                 345                 350
Ala Gln Gly Ser Asp Val Ser Leu Thr Ala Cys Lys Val
        355                 360                 365

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

ACATGGTTAA GGCCTGTTGC                                           20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:25:

GCCACATCTG GCTTGAAATT                                                       20

(2) INFORMATION FOR SEQ ID NO:26:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (ix) FEATURE:
                (A) NAME/KEY: modified_base
                (B) LOCATION: 1
                (D) OTHER INFORMATION: /mod_base= OTHER
                    /note= "N = 5'-biotinylated adenine (bio-A)"

(xi) SEQUENCE DESCRIPTION: SEQ ID NO:26:

NGCTGTTCGT GTTCTATGAT C                                                     21

(2) INFORMATION FOR SEQ ID NO:27:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (ix) FEATURE:
                (A) NAME/KEY: modified_base
                (B) LOCATION: 1
                (D) OTHER INFORMATION: /mod_base= OTHER
                    /note= "N = 5'-biotinylated adenine (bio-A)"

(xi) SEQUENCE DESCRIPTION: SEQ ID NO:27:

NGCTGTTCGT GTTCTATGAT G                                                     21

(2) INFORMATION FOR SEQ ID NO:28:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: DNA (ix) FEATURE:
                (A) NAME/KEY: modified_base
                (B) LOCATION: 1
                (D) OTHER INFORMATION: /mod_base= OTHER
                    /note= "N = 5'-phosphorylated adenine (p-A)"

(ix) FEATURE:
                (A) NAME/KEY: modified_base
                (B) LOCATION: 19
                (D) OTHER INFORMATION: /mod_base= OTHER
                    /note= "N = 3'-digoxigenin-conjugated adenine (A-dig)"

(xi) SEQUENCE DESCRIPTION: SEQ ID NO:28:

NTGAGAGTCG CCGTGTGGN                                                        19

(2) INFORMATION FOR SEQ ID NO:29:

(i) SEQUENCE CHARACTERISTICS:

```
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GGAAGAGCAG AGATATACGT GCCAGGTGGA GCACCCAGG                           39

(2) INFORMATION FOR SEQ ID NO:30:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GGAAGAGCAG AGATATACGT ACCAGGTGGA GCACCCAGG                           39

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CAAAAGAAGC GGAGATTTAA CG                                             22

(2) INFORMATION FOR SEQ ID NO:32:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

AGATTTAACG GGGACGTGC                                                 19

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

AGAGGTCACA TGATGTGTCA CC                                             22

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:34:

AGGAGGCACT TGTTGGTCC                                                            19

(2) INFORMATION FOR SEQ ID NO:35:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:35:

AAAATCACAA CCACAGCAAA G                                                         21

(2) INFORMATION FOR SEQ ID NO:36:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:36:

TTCCCACAGT GAGTCTGCAG                                                           20

(2) INFORMATION FOR SEQ ID NO:37:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:37:

CAATGGGGAT GGGACCTAC                                                            19

(2) INFORMATION FOR SEQ ID NO:38:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:38:

ATATACGTGC CAGGTGGAGC                                                           20

(2) INFORMATION FOR SEQ ID NO:39:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:39:

```
CCTCTTCACA ACCCCTTTCA                                             20

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

CATAGCTGTG CAACTCACAT CA                                          22

(2) INFORMATION FOR SEQ ID NO:41:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

AGCTGTTCGT GTTCTATGAT CATGAGAGTC GCCGTGTGGA                        40

(2) INFORMATION FOR SEQ ID NO:42:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

AGCTGTTCGT GTTCTATGAT GATGAGAGTC GCCGTGTGGA                        40

(2) INFORMATION FOR SEQ ID NO:43:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

TGTTCTATGA TCATGAGAGT CGCCGTGTGG AG                                32

(2) INFORMATION FOR SEQ ID NO:44:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

TGTTCTATGA TCATGAGTGT CGCCGTGTGG AG                                32
```

HEREDITARY HEMOCHROMATOSIS GENE

This is a continuation-in-part of U.S. Ser. No. 08/632,673, filed Apr. 16, 1996, which is a continuation-in-part of U.S. Ser. No. 08/630,912, filed Apr. 4, 1996, now abandoned.

BACKGROUND OF THE INVENTION

1. Field of the Invention

The invention relates generally to the gene, and mutations thereto, that are responsible for the disease hereditary hemochromatosis (HH). More particularly, the invention relates to the identification, isolation, and cloning of the DNA sequence corresponding to the normal and mutant HH genes, as well as the characterization of their transcripts and predicted gene products. The invention also relates to methods and the like for screening for HH homozygotes and further relates to HH diagnosis, prenatal screening and diagnosis, and therapies of HH disease, including gene therapeutics, protein and antibody based therapeutics, and small molecule therapeutics.

2. Background of the Technology

Hereditary hemochromatosis (HH) is an inherited disorder of iron metabolism wherein the body accumulates excess iron. In symptomatic individuals, this excess iron leads to deleterious effects by being deposited in a variety of organs leading to their failure, and resulting in cirrhosis, diabetes, sterility, and other serious illnesses. Neither the precise physiological mechanism of iron overaccumulation nor the gene which is defective in this disease has been described.

HH is inherited as a recessive trait; in the current state of knowledge, homozygotes carrying two defective copies of the gene are affected by the disease. It is estimated that approximately 10% of individuals of Western European descent carry one copy of the HH gene mutation and that there are about one million homozygotes in the United States. HH, thus, represents one of the most common genetic disease mutations in individuals of Western European descent. Although ultimately HH produces debilitating symptoms, the majority of homozygotes have not been diagnosed. Indeed, it has been estimated that no more than a small fraction of affected individuals in the United States have been diagnosed with this condition.

The symptoms of HH are often similar to those of other conditions, and the severe effects of the disease often do not appear immediately. Accordingly, it would be desirable to provide a method to identify persons who may be destined to become symptomatic in order to intervene in time to prevent excessive tissue damage associated with iron overload. One reason for the lack of early diagnosis is the inadequacy of presently available diagnostic methods to ascertain which individuals are at risk, especially while such individuals are presymptomatic.

Although blood iron parameters can be used as a screening tool, a confirmed diagnosis often employs liver biopsy which is undesirably invasive, costly, and carries a risk of mortality. Thus, there is a clear need for the development of an inexpensive and noninvasive diagnostic test for detection of homozygotes in order to facilitate diagnosis in symptomatic individuals, provide presymptomatic detection to guide intervention in order to prevent organ damage, and for identification of heterozygote carriers.

The need for such diagnostics is documented, for example, in Barton, J. C. et al. *Nature Medicine* 2:394–395 (1996); Finch, C. A. *West J Med* 153:323–325 (1990); McCusick, V. *Mendelian Inheritance in Man* pp. 1882–1887, 11th ed., (Johns Hopkins University Press, Baltimore (1994)); *Report of a Joint World Health Organization/Hemochromatosis Foundation/French Hemochromatosis Association Meeting on the Prevention and Control of Hemochromatosis* (1993); Edwards, C. Q. et al. *New Engl J Med* 328:1616–1620 (1993); Bacon, B. R. *New Engl J Med* 326:126–127 (1992); Balan, V. et al. *Gastroenterology* 107:453–459 (1994); Phatak, P. D. et al. *Arch Int Med* 154:769–776 (1994).

Although the gene carrying the mutation or mutations that cause HH has previously been unknown, genetic linkage studies in HH families have shown that the gene that causes the disease in Caucasians appears to reside on chromosome 6 near the HLA region at 6p21.3 (Cartwright, *Trans Assoc Am Phys* 91:273–281 (1978); Lipinski, M. et al. *Tissue Antigens* 11:471–474 (1978)). It is believed that within this locus, a single mutation gave rise to the majority of disease-causing chromosomes present in the population today. See Simon, M. et al. *Gut* 17:332–334 (1976); McCusick, V. supra. This is referred to herein as the "common" or "ancestral" or "common ancestral" mutation. These terms are used interchangeably. It appears that about 80% to 90% of all HH patients carry at least one copy of the common ancestral mutation which is closely linked to specific alleles of certain genetic markers close to this ancestral HH gene defect. These markers are, as a first approximation, in the allelic form in which they were present at the time the ancestral HH mutation occurred. See, for example, Simon, M. et al. *Am J Hum Genet* 41:89–105 (1987); Jazwinska, E. C. et al. *Am J Hum Genet* 53:242–257 (1993); Jazwinska, E. C. et al. *Am J Hum Genet* 56:428–433 (1995); Worwood, M. et al. *Brit J Hematol* 86:863–866 (1994); Summers, K. M. et al. *Am J Hum Genet* 45:41–48 (1989).

Several polymorphic markers in the putative HH region have been described and shown to have alleles that are associated with HH disease. These markers include the published microsatellite markers D6S258, D6S306 (Gyapay, G. et al. *Nature Genetics* 7:246–339 (1994)), D6S265 (Worwood, M. et al. *Brit J Hematol* 86:833–846 (1994)), D6S105 (Jazwinska, E. C. et al. *Am J Hum Genet* 53:242–257 (1993); Jazwinska, E. C. et al. *Am J Hum Genet* 56:428–433 (1995)), D6S1001 (Stone, C. et al. *Hum Molec Genet* 3:2043–2046 (1994)), D6S1260 (Raha-Chowdhury, R. et al. *Hum Molec Genet* 4:1869–1874 (1995)) as well as additional microsatellite and single-nucleotide-polymorphism markers disclosed in co-pending U.S. patent application Ser. No. 08/599,252, filed Feb. 9, 1996, which is a continuation-in-part of U.S. patent application Ser. No. 08/559,302, filed Nov. 15, 1995, now abandoned, which is a continuation-in-part of U.S. patent application Ser. No. 08/436,074, filed May 8, 1995, the disclosures of which are hereby incorporated by reference in their entirety.

Although each of such markers may be of use in identifying individuals carrying the defective HH gene, crossing-over events have, over time, separated some of the ancestral alleles from the mutation that is responsible for HH, thereby limiting the utility of such surrogate markers. The limited diagnostic power of surrogate markers is obvious considering the fact that the frequency of the ancestral allele in the population is generally higher than the estimated frequency of the disease-causing mutation. The only exception is a marker designated 24d1, which has been disclosed in U.S. patent application Ser. No. 08/599,252, filed on Apr. 16, 1996. The ancestral allele of 24d1 has a population frequency that is consistent with the estimated frequency of the ancestral HH mutation. The desirability of identifying the gene responsible for HH has long been recognized due to the health benefits that would be available via gene-based diagnostics, which has an intrinsically higher predictive power than surrogate markers and may eventually lead to the identification and diagnosis of disease-causing mutations other than the ancestral mutation. In addition, identification of the HH gene would further our understanding of the molecular mechanisms involved in HH disease thereby opening new approaches for therapy. This goal has motivated numerous, but previously unsuccessful attempts to identify the HH gene.

These attempts have been made by a variety of methods. For example, genes known to be involved in iron transport or metabolism have been examined as candidates. An example of one unsuccessful attempt is the assignment of the ferritin heavy chain gene to Chromosome 6p, and subsequent exclusion of this gene on the basis of its precise localization outside of the HH region, and failure to find mutations in HH patients. See Dugast I. J. et al. *Genomics* 6:204–211 (1990); Summers et al. *Hum Genet* 88:175–178 (1991).

Another strategy has been to employ the genomic DNA surrounding the postulated HH locus to select expressed genes from this region. These genes have been evaluated in HH patients for mutations in an attempt to identify them as the causative gene. Examples of searches, that have not resulted in the identification of the HH gene are illustrated in El Kahloun et al. *Hum Molec Genet* 2:55–60 (1992), Goei et al. *Am J Hum Genet* 54:244–251 (1994), and Beutler et al. *Blood Cells, Molecules, and Diseases* 21:206–216 (1995).

Finally, although the strategy of using positional information obtained from genetic studies has long been a widely used approach, estimates of the position of the HH gene remained imprecise. Examples of this uncertainty are demonstrated in Gruen et al. *Genomics* 14:232–240 (1992) and in Gasparini et al. *Hematology* 19:1050–1056 (1994). Indeed, a number of contradictory conclusions have been reported, some placing the HH gene proximal of HLA-A (Edwards et al. *Cytogenet Cell Genet* 40:620 (1985); Gasparini, P. et al. *Hum Molec Genet* 2:571–576 (1993)) while others placed the gene distal of HLA-A (Calandro et al. *Hum Genet* 96:339–342 (1995)).

Until very recently, in spite of the linkage studies placing the HH disease gene in the HLA region of Chromosome 6, the biological relevance of alterations in HLA Class I components has not been particularly well explored. Work by de Sousa et al. *Immun Lett* 39:105–111 (1994), and more recent work by Rothenberg, B. E. and Voland, J. R. *Proc Natl Acad Sci USA* 93:1529–1534 (1996) indicated that β-2-microglobulin knock-out mice develop symptoms of iron overload. β2-microglobulin is presented on cell surfaces as a complex with HLA Class I MHC's. de Sousa et al. supra. (1994) and Barton, J. C. and Bertoli, L. F. *Nature Medicine* 2:394–395 (1996) speculated that β-2-microglobulin associated proteins or a unique Class I gene could be involved in the control of intestinal iron absorption and possibly HH disease.

In spite of the extensive efforts in the art to find the gene responsible for HH, the gene has remained elusive. Nevertheless, as will be appreciated it would be highly desirable to identify, isolate, clone, and sequence the gene responsible for HH. Such identification, isolation, cloning, and sequencing of the gene would enable the design and manufacture of products useful for the diagnosis and screening for HH. This is useful because a safe and effective therapy is available in the form of phlebotomy. Identification of individuals affected with HH will allow initiation of this therapy, which can prevent symptoms, arrest progression of organ damage, and in some cases reverse pathology due to iron overload. In addition, such identification, isolation, and cloning of the gene would enable the study of the operation of the gene in the development of iron overload diseases, in general, and HH in particular. Further, it would be highly desirable to provide therapeutics for iron overload diseases, and HH disease in particular, as well as oxidative free radical diseases, reactions, and processes in general. The identification, isolation, sequencing, and cloning of the gene and identification of its protein products would also facilitate improved therapeutic development.

SUMMARY OF THE INVENTION

In accordance with the present invention, we have identified, isolated, cloned and sequenced the gene, which in mutated form, is responsible for HH. The gene is a previously unknown gene, located on Chromosome 6 telomeric of the HLA locus. The gene possesses substantial sequence similarity to HLA Class I genes. Thus, the gene and its protein products are expected to be similar in structural and in certain functional respects to other HLA genes and proteins. Yet, the gene is unique in its involvement in, and/or influence over, iron absorption.

The principal mutation found in the gene comprises a single nucleotide substitution which causes a significant amino acid change in the protein product expressed by the gene. Such amino acid change would appear to render the protein incapable of its normal function including presentation on the cell surface.

The present invention, therefore, represents the first opportunity to accurately and noninvasively screen and diagnose HH in a substantial portion of the population. In addition, the present invention enables the study of the HH gene. Through such study, the development of therapeutics (gene, protein replacement, antibodies, small molecules, and the like) for HH disease will be enabled.

In accordance with a first aspect of the present invention, there is provided an isolated nucleic acid comprising a nucleic acid sequence selected from the group consisting of:

nucleic acid sequences corresponding to the nucleic acid sequence of SEQ ID NO:1 (which corresponds to the genomic sequence of the HH gene including introns and exons as shown in FIGS. 3A–3K);

nucleic acid sequences corresponding to the nucleic acid sequences selected from the group consisting of SEQ ID NO:3 (which corresponds to the genomic sequence of the HH gene containing the 24d1 mutation as shown in FIGS. 3A–3K), SEQ ID NO:5 (which corresponds to the genomic sequence of the HH gene containing the 24d2 mutation as shown in FIGS. 3A–3K), SEQ ID NO:7 (which corresponds to the genomic sequence of the HH gene containing the 24d1 and the 24d2 mutations as shown in FIGS. 3A–3K); nucleic acid sequences corresponding to the nucleic acid sequence of SEQ ID NO:9 (which corresponds to the cDNA sequence including the coding sequence of the HH gene as shown in FIGS. 4A–4C);

nucleic acid sequences corresponding to the nucleic acid sequences selected from the group consisting of SEQ ID NO:10 (which corresponds to the cDNA sequence including the coding sequence of the HH gene containing the 24d1 mutation as shown in FIGS. 4A–4C), SEQ ID NO:11 (which corresponds to the cDNA sequence including the coding sequence of the HH gene containing the 24d2 mutation as shown in FIGS. 4A–4C), and SEQ ID NO:12 (which corresponds to the cDNA sequence including the coding sequence of the HH gene containing the 24d1 and the 24d2 mutations as shown in FIGS. 4A–4C);

nucleic acid sequences which correspond to a fragment of the sequence of SEQ ID NO:9 (which corresponds to the cDNA sequence including the coding sequence of the HH gene as shown in FIGS. 4A–4C) which include at least 18 sequential nucleotides;

nucleic acid sequences which correspond to a fragment of a sequence selected from the group consisting of SEQ ID NO:10 (which corresponds to the cDNA sequence including the coding sequence of the HH gene containing the 24d1 mutation as shown in FIGS. 4A–4C), SEQ ID NO:11 (which corresponds to the cDNA sequence including the coding sequence of the HH gene containing the 24d2 mutation as shown in FIGS. 4A–4C), and SEQ ID NO:12 (which corresponds to the cDNA sequence including the coding sequence of the HH gene containing the 24d1 and 24d2 mutations as shown in FIGS. 4A–4C) which include at least 18 sequential nucleotides;

nucleic acid sequences which correspond to a fragment of the sequence of SEQ ID NO:9 (which corresponds to the cDNA sequence including the coding sequence of the HH gene as shown in FIGS. 4A–4C) which include at least 18 sequential nucleotides and encode a fragment of an amino acid sequence corresponding to SEQ ID NO:2 (which corresponds to the sequence of the HH protein without mutations as shown in FIG. 4A–4C); and nucleic acid sequences which correspond to a fragment of a sequence selected from the group consisting of SEQ ID NO:10 (which corresponds to the cDNA sequence including the coding sequence of the HH gene containing the 24d1 mutation as shown in FIGS. 4A–4C), SEQ ID NO:11 (which corresponds to the cDNA sequence including the coding sequence of the HH gene containing the 24d2 mutation as shown in FIGS. 4A–4C), and SEQ ID NO:12 (which corresponds to the cDNA sequence including the coding sequence of the HH gene containing the 24d1 and 24d2 mutations as shown in FIGS. 4A–4C) which include at least 18 sequential nucleotides and encode a fragment of an amino acid sequence corresponding to SEQ ID NO:4 (which corresponds to the sequence of the HH protein containing the amino acid change caused by the 24d1 mutation as shown in FIG. 4), SEQ ID NO:6 (which corresponds to the sequence of the HH protein containing the amino acid change caused by the 24d2 mutation as shown in FIGS. 4A–4C), and SEQ ID NO:8 (which corresponds to the sequence of the HH protein containing the amino acid changes caused by the 24d1 and 24d2 mutations as shown in FIGS. 4A–4C).

In one embodiment, the nucleic acid is DNA. In another embodiment, the DNA is cDNA. In another embodiment, the nucleic acid is a nucleic acid sequence corresponding to the nucleic acid sequence of SEQ ID NO:1, In another embodiment, the nucleic acid is a nucleic acid sequence corresponding to the nucleic acid sequence of SEQ ID NO:9, In another embodiment, the nucleic acid is a nucleic acid sequence corresponding to a nucleic acid sequence selected from the group consisting of SEQ ID NO:3, SEQ ID NO:5 and SEQ ID NO:7. In another embodiment, the nucleic acid is a nucleic acid sequence corresponding to a nucleic acid sequence selected from the group consisting of SEQ ID NO:10, SEQ ID NO:11, and SEQ ID NO:12.

In accordance with a second aspect of the present invention, there is provided a nucleic acid probe, comprising a nucleotide sequence corresponding to a portion of a nucleic acid as set forth in any one of the foregoing nucleic acid sequences.

In accordance with a third aspect of the present invention, there is provided a cloning vector comprising a coding sequence of a nucleic acid as set forth above and a replicon operative in a host cell for the vector.

In accordance with a fourth aspect of the present invention, there is provided an expression vector comprising a coding sequence of a nucleic acid set forth above operably linked with a promoter sequence capable of directing expression of the coding sequence in host cells for the vector.

In accordance with a fifth aspect of the present invention, there is provided host cells transformed with a vector as set forth above.

In accordance with a sixth aspect of the present invention, there is provided a method of producing a mutant HH polypeptide comprising: transforming host cells with a vector capable of expressing a polypeptide from a nucleic acid sequence as set forth above; culturing the cells under conditions suitable for production of the polypeptide; and recovering the polypeptide.

In accordance with a seventh aspect of the present invention, there is provided a peptide product selected from the group consisting of: a polypeptide having the amino acid sequence corresponding to the sequence of SEQ ID NO:2; a polypeptide having the amino acid sequence corresponding to the sequence of SEQ ID NO:4, SEQ ID NO:6, and SEQ ID NO:8; a peptide comprising at least 6 amino acid residues corresponding to the sequence of SEQ ID NO:2; a peptide comprising at least 6 amino acid residues corresponding to the sequence of SEQ ID NO:4, SEQ ID NO:6, and SEQ ID NO:8. In one embodiment, the peptide is labelled. In another embodiment, the peptide is a fusion protein.

In accordance with an eighth aspect of the present invention, there is provided a use of a peptide as set forth above as an immunogen for the production of antibodies. In one embodiment, there is provided an antibody produced in such application. In one embodiment, the antibody is labelled. In another embodiment, the antibody is bound to a solid support. In another embodiment, the antibody is bound to a solid support.

In accordance with a ninth aspect of the present invention, there is provided a method to determine the presence or absence of the common hereditary hemochromatosis (HH) gene mutation in an individual, comprising: providing DNA or RNA from the individual; and assessing the DNA or RNA for the presence or absence of the HH-associated allele A of a base-pair mutation designated herein 24d1, wherein, as a result, the absence of the allele indicates the absence of the HH gene mutation in the genome of the individual and the presence of the allele the presence of the HH gene mutation in the genome of the individual.

In one embodiment, the assessing step is performed by a process which comprises subjecting the DNA or RNA to amplification using oligonucleotide primers flanking the base-pair mutation 24d1. In another embodiment, the assessing step further comprises an oligonucleotide ligation assay. In another embodiment, the assessing step further comprises providing a housing having a first well that is adapted for conducting an oligonucleotide ligation assay and providing a signal when the A allele of the 24d1 mutation is present in the DNA or RNA and a second well that is adapted for conducting an oligonucleotide ligation assay and providing a signal when the G allele of the 24d1 mutation is present in the DNA or RNA. In another embodiment, the assessing step further comprises detecting whether the DNA or RNA is homozygous or heterozygous for the 24d1 mutation, wherein when the DNA or RNA is heterozygous for the 24d1 mutation a signal will be observed in both wells upon conducting the oligonucleotide ligation assay and when the DNA or RNA is homozygous for the 24d1 mutation only a signal in the first well will be observed in both wells upon conducting the oligonucleotide ligation assay. In another embodiment, DNA is amplified with oligonucleotide primers of SEQ ID NO:13 and SEQ ID NO:14. In another embodiment, the assessing step further comprises an oligonucleotide ligation assay. In another embodiment, the oligonucleotide ligation assay is accomplished using oligonucleotides of SEQ ID NO:15, SEQ ID NO:16, and SEQ ID NO:17. In another embodiment, RNA is amplified with oligonucleotide primers of SEQ ID NO:18 and SEQ ID NO:19. In another embodiment, the assessing step further comprises an oligonucleotide ligation assay. In another embodiment, the oligonucleotide ligation assay is accomplished using oligonucleotides of SEQ ID NO:15, SEQ ID NO:16, and SEQ ID NO:17.

In accordance with a tenth aspect of the present invention, there is provided a method for diagnosing whether a patient is afflicted with hereditary hemochromatosis (HH) disease, comprising: contacting cells of the patient with antibodies directed against an epitope on an HH protein product corresponding substantially to SEQ ID NO:2; and observing whether the antibodies localize on the cells, wherein, in the observing step, if antibodies do not localize to the cell there is a probability that the patient is afflicted with HH. In one embodiment, the method is conducted in vitro. In another embodiment, the method is conducted in vivo.

In accordance with an eleventh aspect of the present invention, there is provided a method for treating a patient diagnosed as having hereditary hemochromatosis (HH) disease and homozygous for a 24d1(A) mutation, comprising delivering a polypeptide corresponding to the amino acid sequence of SEQ ID NO:2 to tissues of the patient. In one embodiment, the polypeptide is delivered directly to the tissues. In another embodiment, the polypeptide is delivered intravenously. In another embodiment, the polypeptide is delivered to the tissues through gene therapy.

In accordance with a twelfth aspect of the present invention, there is provided an animal model for hereditary hemochromatosis (HH) disease, comprising a mammal possessing a mutant or knocked-out HH gene.

In accordance with a thirteenth aspect of the present invention, there are provided metal chelation agents derived from nucleic acid sequences described above or from a peptide product as described above in a physiologically acceptable carrier. In one embodiment, the metal is selected from the group consisting of iron, mercury, cadmium, lead, and zinc.

In accordance with a fourteenth aspect of the present invention, there is provided a method to screen mammals for susceptibility to metal toxicities, comprising, screening such mammals for a mutation in the HH gene and wherein those mammals identified as having a mutation are more susceptible to metal toxicities than mammals not identified as having a mutation. In one embodiment, the metal is selected from the group consisting of iron, mercury, cadmium, lead, and zinc.

In accordance with a fifteenth aspect of the present invention, there is provided a method for selecting patients infected with hepatitis virus for α-interferon treatment, comprising screening such patients for a mutation in the HH gene and wherein those patients not identified as having a mutation are selected to proceed with α-interferon treatment and those identified as having a mutation are selected to undergo phlebotomy prior to α-interferon treatment.

In accordance with a sixteenth aspect of the present invention, there is provided a T-cell differentiation factor comprising a moiety selected from the group consisting of molecules derived from nucleic acid sequences described above and from peptide products described above.

In accordance with a seventeenth aspect of the present invention, there is provided a method for screening potential therapeutic agents for activity in connection with HH disease, comprising: providing a screening tool selected from the group consisting of a cell line, a cell free, and a mammal containing or expressing a defective HH gene or gene product; contacting the screening tool with the potential therapeutic agent; and assaying the screening tool for an activity selected from the group consisting of HH protein folding, iron uptake, iron transport, iron metabolism, receptor-like activities, upstream processes, downstream processes, gene transcription, and signaling events.

In accordance with an eighteenth aspect of the present invention, there is provided a therapeutic agent for the mitigation of injury due to oxidative processes in vivo, comprising a moiety selected from the group consisting of molecules derived from nucleic acid sequences described above and from peptide products described above.

In accordance with a nineteenth aspect of the present invention, there is provided a method for diagnosing a patient as having an increased risk of developing HH disease, comprising: providing DNA or RNA from the individual; and assessing the DNA or RNA for the presence or absence of the HH-associated allele A of a base mutation designated herein 24d1 in combination with assessing the DNA or RNA for the HH-associated allele G of a base mutation designated herein 24d2, wherein, as a result, the absence of the alleles indicates the absence of the HH gene mutation in the genome of the individual and the presence of the alleles indicates the presence of the HH gene mutation in the genome of the individual and an increased risk of developing HH disease.

In accordance with a twentieth aspect of the present invention, there is provided a therapeutic agent for the mitigation of iron overload, comprising a moiety selected from the group consisting of molecules derived from nucleic acid sequences described above and from peptide products described above.

In accordance with a twenty-first aspect of the present invention, there is provided a method for treating hereditary hemochromatosis (HH) disease, comprising: providing an antibody directed against an HH protein sequence or peptide product; and delivering the antibody to affected tissues or cells in a patient having HH.

In accordance with a twenty-second aspect of the present invention, there is provided an antisense oligonucleotide directed against a transcriptional product of a nucleic acid sequence selected from the group consisting of therapeutic agent for the mitigation of iron overload, comprising a moiety selected from the group consisting of SEQ ID NO:1, SEQ ID NO:3, SEQ ID NO:5, SEQ ID NO:7, SEQ ID NO:9, SEQ ID NO:10, SEQ ID NO:11, and SEQ ID NO:12.

BRIEF DESCRIPTION OF THE DRAWING FIGURES

FIG. 1. is a physical map showing the positions of markers on Chromosome 6 telomeric of the HLA region and the set of genomic clones used in our gene discovery efforts. In the Figure, "y" designates a YAC (yeast artificial chromosome) clone, "p" designates a p1 clone, "b" designates a BAC (bacterial artificial chromosome) clone, and "pc" designates a PAC (p1 artificial chromosome).

FIG. 2. is a subset of chromosomes showing the overlap of ancestral DNA between HH affected chromosomes from patients at markers in a narrow region of Chromosome 6, approximately 4.8 Mbp telomeric of the HLA region. These overlapping regions were used to define the minimal HH region. Shaded regions are "ancestral regions" maintained "identical by descent." The region that is ancestral and in common between all of these chromosomes is between markers 241-29 and 63-3. This is where the HH gene should reside.

FIGS. 3A–3K. is a nucleotide sequence of the genomic DNA containing the HH gene (SEQ ID NO:1). The sequence comprises approximately 11,000 nucleotides. The sequence corresponding to the HH gene coding regions have been capitalized and underlined. The positions of the 24d1 and the 24d2 mutations and the 24d7 sequence variants are shown where base 5474 corresponds to the position of the 24d1 mutation, base 3512 corresponds to the position of the 24d2 mutation, and base 3518 corresponds to the position of the 24d7 sequence variation. Sequences corresponding to the genomic DNA including the 24d1 mutation are referred to herein as SEQ ID NO:3, sequences corresponding to the genomic DNA including the 24d2 mutation are referred to herein as SEQ ID NO:5, and sequences corresponding to the genomic DNA including the 24d1 and the 24d2 mutations are referred to herein as SEQ ID NO:7.

FIGS. 4A–4C. is the nucleotide sequence of the translated portion of the cDNA (SEQ ID NO:9) corresponding to coding regions in the HH gene. The nucleotide sequence of the cDNA is arbitrarily numbered beginning at 1 with the A in the start codon (ATG). The predicted amino acid sequence of the protein product is provided (SEQ ID NO:4); and sequence variants in the gene, as well as the associated changes in the amino acid sequence caused by such variants are indicated on the Figure at base 187 (residue 63), base 193 (residue 65), and base 845 (residue 282). Sequences corresponding to cDNA including the 24d1 mutation are referred to herein as SEQ ID NO:10, sequences corresponding to the cDNA including the 24d2 mutation are referred to herein as SEQ ID NO:11, and sequences corresponding to the cDNA including the 24d1 and the 24d2 mutations are referred to herein as SEQ ID NO:12. Sequences of the predicted protein product including the amino acid change caused by the 24d1 mutation is referred to herein as SEQ ID NO:4, sequences of the predicted protein product including the amino acid change caused by the 24d2 mutation is referred to herein as SEQ ID NO:6, and sequences of the predicted HH protein product including the amino acid change caused by the 24d1 and 24d2 mutations is referred to herein as SEQ ID NO:8.

FIG. 5. shows the oligonucleotide sequences used for amplification (SEQ ID NO:13 and SEQ ID NO:14) and OLA determination (SEQ ID NO:15, SEQ ID NO:16, and SEQ ID NO:17) of the 24d1 gene mutation of the present invention.

FIG. 6. shows a 517 base sequence representing the genomic DNA surrounding the 24d1 gene mutation of the present invention.

FIG. 6a shows the position of 24d1 in the normal G allele and the portions of the sequence used for the design of the primers illustrated in FIG. 5 (SEQ ID NO:20), and FIG. 6b shows the position of 24d1 in the mutated A allele and the portions of the sequence used for the design of the primers illustrated in FIG. 5 (SEQ ID NO:21).

FIG. 7. shows the sequence alignment between the predicted amino acid sequence of the HH gene protein product (SEQ ID NO:2) in comparison to RLA (rabbit leukocyte antigen) (SEQ ID NO:22) and an MHC Class I protein (SEQ ID NO:23). The dots above certain amino acids correspond to conservative amino acid residue differences, i.e., glycine for alanine, valine for isoleucine for leucine, aspartic acid for glutamic acid, asparagine for glutamine, serine for threonine, lysine for arginine, and phenylalanine for tyrosine, or the reverse.

FIG. 8. is a schematic diagram showing the association between an HLA molecule and β-2-microglobulin highlighting the homologous positions of the three base-pair changes that have been found in the predicted HH gene protein product.

FIG. 9. shows the oligonucleotide sequences used for amplification (SEQ ID NO:24 and SEQ ID NO:25) and OLA determination (SEQ ID NO:26, SEQ ID NO:27, and SEQ ID NO:28) of the 24d1 gene mutation of the present invention.

DETAILED DESCRIPTION OF THE INVENTION

I. Definitions

Figure 1:
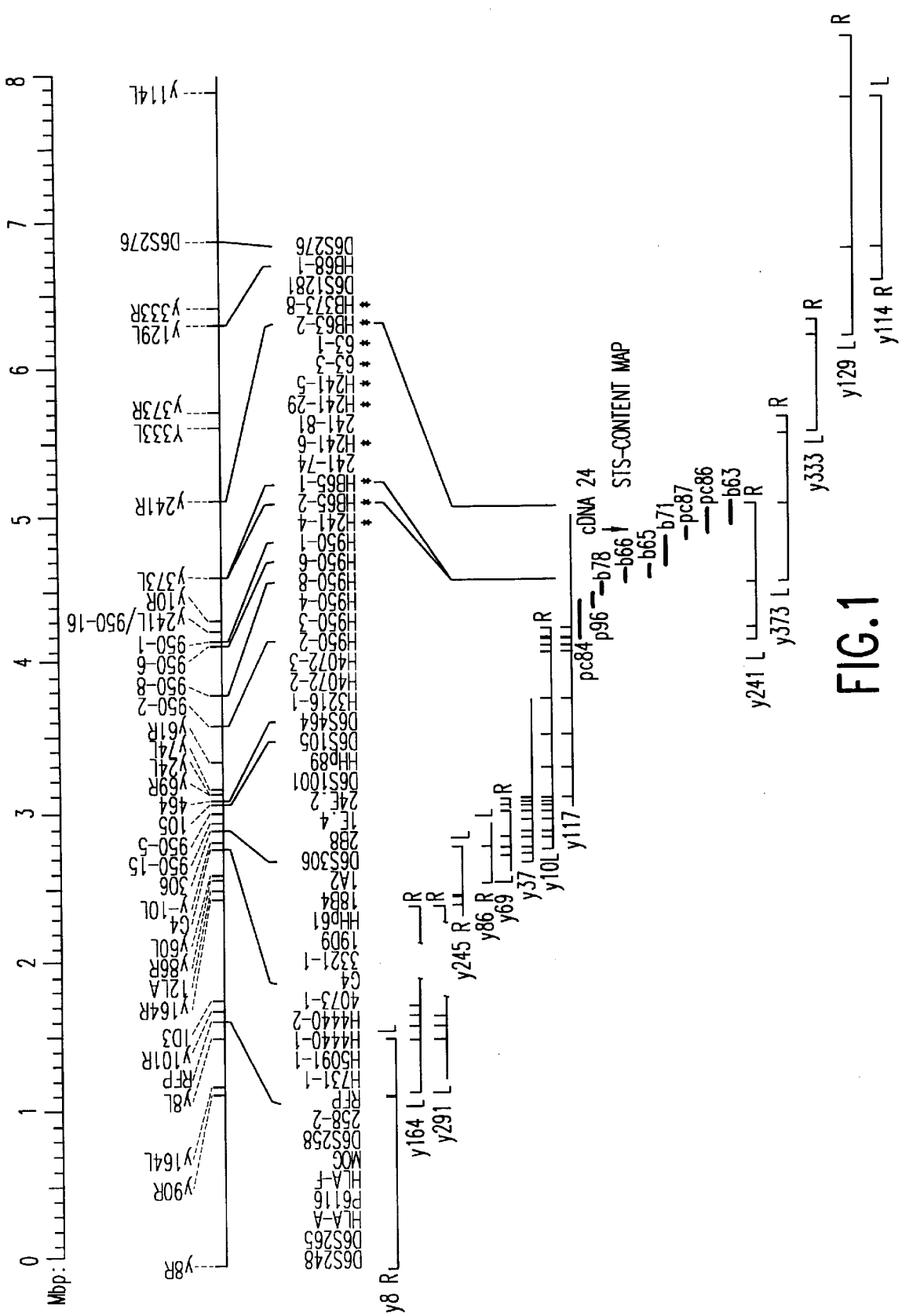
Figure 8:
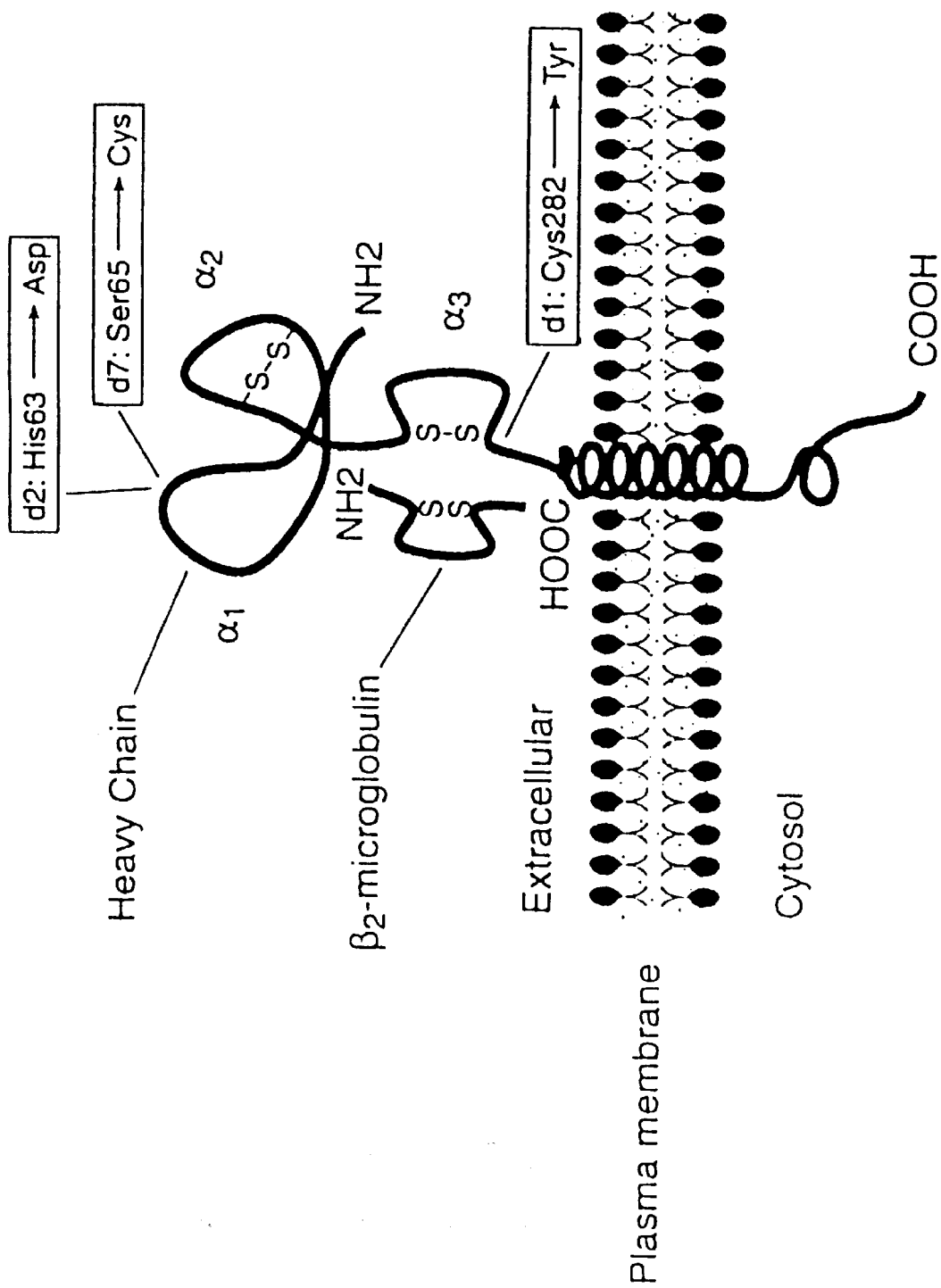

As used herein, the term "random chromosomes" refers to chromosomes from randomly chosen individuals who are not known to be affected with HH. Similarly, the term "unaffected individuals" refers to individuals who are not known to be affected with HH. The term "affected chromosomes" as used herein refers to chromosomes from individuals who have been diagnosed as having HH as determined by hepatic iron index and liver biopsy. Similarly, the term "affected individuals" refers to individuals who have been diagnosed as having HH.

As used herein, "marker" refers to a DNA sequence polymorphism flanked by unique regions. These regions flanking the "marker" can be utilized for the design and construction of oligonucleotides for amplifying the relevant DNA portions and detecting the polymorphisms therein.

The term "HH disease" refers to hereditary hemochromatosis disease. The criteria utilized herein to assess whether a patient is affected with the HH disease (i.e., whether the patient is an "affected individual" having "affected chromosomes") has been established by the diagnostic criteria set out in Crawford et al. *Am J Hum Genet* 57:362–367 (1995) where at least two of the following four criteria were met: (i) liver biopsy showing HIC greater than 4660 micrograms/gram of liver, (ii) HII greater than or equal to 2.0, (iii) Perl stain of 3 or greater, or (iv) greater than 4 grams of iron removed by phlebotomy (greater than 16 therapeutic phlebotomies).

"HH gene" as used herein refers to a gene whose mutated forms are associated with HH disease. This definition includes various sequence polymorphisms, mutations, and/or sequence variants wherein nucleotide substitutions in the gene sequence do not affect the function of the gene product. Generally, the HH gene is found on Chromosome 6 and includes the DNA sequences shown in FIGS. 3 and 4 and all functional equivalents. The term "HH gene" includes not only coding sequences but also regulatory regions such as promoter, enhancer, and terminator regions. The term further includes all introns and other DNA sequences spliced from the final HH gene RNA transcript. Further, the term includes the coding sequences as well as the non-functional sequences found in non-human species.

The terms "HH protein" and "HH gene product" refer to MHC Class I-like molecules encoded by the HH gene. The term includes protein as isolated from human and animal sources, produced by enzymatic or chemical means, or through recombinant expression in an organism. The term further includes "normal" and "wild-type" forms of the protein and mutant forms of the protein that are responsible or involved in HH disease. Encompassed within this definition are forms of the protein including polymorphic forms of the protein in which the amino acid changes do not affect the essential functioning of the protein in its role as either "normal" or "wild-type" or mutant forms of the protein.

"Ancestral DNA" as used herein refers to DNA that is inherited in unchanged form through multiple generations. Such DNA is sometimes referred to herein as DNA that is "identical by descent."

The term "ancestral mutation" as used herein refers to the disease causing mutation inherited through multiple generations.

Additional definitions that may be of assistance in understanding the present invention are provided in World Patent Application No. WO 96/05306, the disclosure of which is hereby incorporated by reference in its entirety.

II. Introduction to HH Gene Discovery

Through the analysis of affected chromosomes as compared to random chromosomes, in accordance with the present invention, we have identified, isolated, and sequenced the cDNA corresponding to the normal and mutant HH gene. In addition, we have sequenced the cDNA correspondence to the gene's mRNA and have predicted the gene's protein product.

The HH disease gene is a novel gene on Chromosome 6 having significant sequence homology with HLA Class I genes. Interestingly, however, the gene is located at significant distance telomeric (approximately 4 Mbp) from the HLA Class I gene cluster on Chromosome 6. A single mutation in the gene appears responsible for the majority of HH disease. The mutation comprises a single nucleotide substitution of Guanine (G) to Adenine (A), where Guanine (G) is present in the unaffected DNA sequence and Adenine (A) is present in the affected DNA sequence. The mutation of the present invention, referred to herein as 24d1, is illustrated in two partial sequences from the genomic DNA of the HH gene below and represented by SEQ ID NO:29 (unaffected) and SEQ ID NO:30 (affected):

recent evidence demonstrated that β-2-microglobulin knock-out mice developed symptoms of iron overload disease. The predicted amino acid sequence of the gene product of the present invention possesses significant homology to HLA Class I molecules which are known to interact with β-2-microglobulin. Third, the principal mutation (24d1) causes a marked amino acid change (Cys→Tyr) at a critical disulfide bridge held in common with HLA Class I proteins that is important to the secondary structure of such protein products. Changes affecting the disulfide bridge in HLA Class I molecules have been shown to prevent or minimize presentation of the protein on cell surfaces. Further, such amino acid change would appear to substantially modify the manner in which the protein could associate or interact with β-2-microglobulin. Fourth, the 24d1 mutation is present in over 87% of HH patients while only present in 4% of random individuals, consistent with estimates of the frequency of the ancestral HH mutation in patients and the carrier frequency in random individuals.

A. Discovery of the HH Gene

1. Strategy

In order to identify the HH gene, we set out to determine allelic association patterns between known markers and the HH locus in the HLA region of Chromosome 6. Based upon this data, we generated physical clone coverage extending from D6S265, which is a marker that is centromeric of HLA-A, in a telomeric direction through D6S276, a marker at which the allelic association was no longer observed.

2. Allelic Association

As mentioned above, it is believed that there was a common ancestor who possessed a distinct DNA sequence within whose genome the common or ancestral HH mutation occurred. It appears that approximately 87% of the patients today are descendants of this disease founding individual and thus share the common mutation. As will be appreciated, through the generations, chromosomes undergo genetic recombination during meiosis. Both genetic linkage mapping and disequilibrium mapping take advantage of this natural process to narrow and define the location of the disease causing gene. The smaller the distance between a disease locus and a genetic marker, the less likely that a recombination event will occur between them. Thus, as genetic markers are tested in a population of HH patients the markers closest to the disease locus will tend more often to have the allele that was present on the ancestral

```
24d1UnaffectedSequence:                                     (SEQ ID NO:29)
       5'-GGAAGAGCAGAGATATACGT G CCAGGTGGACACCCAGG-
3'

24d1AffectedSequence:                                       (SEQ ID NO:30)
       5'-GGAAGAGCAGAGATATACGT A CCAGGTGGACACCCAGG-
3'
```

The G to A mutation at 24d1 is present in approximately 86% of all affected chromosomes and in only 4% of unaffected chromosomes, exemplifying its enrichment in the affected chromosomes.

As will be discussed in greater detail below, several factors provide a compelling conclusion that the above-mentioned gene of the present invention is in fact the HH gene, and that the 24d1 mutation is responsible for the majority of cases of HH disease. First, the location of the gene on Chromosome 6, in relative proximity to the HLA region, is the predicted location based on linkage disequilibrium mapping studies and haplotype analysis. Second, chromosome, while others, farther away, will tend to have different alleles brought in by genetic recombination. Our strategy for identifying the HH gene, and the mutation(s) responsible for the HH disease, exploited this phenomenon by first reconstructing the haplotype of the founding or ancestral chromosome spanning an 8 Mb region. Secondly, we determined the minimal HH region that is "identical by descent" or shared in the chromosomes in our sample of HH patients.

The approach is shown in FIG. 2 where areas of ancestral sequence that is "identical by descent" are indicated in shade and areas of non-identity are unmarked. Particular markers are shown at the top of the Figure.

Towards the goal of identifying the HH gene, we undertook this type of strategy. Owing to the published allelic association of the HH gene with the HLA region, we directed our initial efforts to this region of Chromosome 6. Existing genetic markers were tested for association with the HH gene. Because of the founder or ancestral effect, described above, we expected that markers closer to the HH gene would display a greater degree of allelic association. Based upon this initial data we designed a strategy to develop markers over a 8 Mb region extending telomeric from HLA-A.

The markers were generally developed by cloning random pieces of genomic DNA, known to represent this region of the chromosome as described in the next section and as shown in FIG. 1. The clones containing CA repeat elements were identified by hybridization and their sequences determined. The sequence information was used to design primers within the unique DNA flanking the CA repeat, for use in PCR. If the CA repeat proved to be polymorphic in a random sample of chromosomes, then the markers were assayed in HH patients. In this effort 46 CA microsatellite markers covering approximately 8 Mb, were identified and scored in our patients. We detected the pattern of overlapping ancestral DNA present on patient chromosomes as depicted in FIG. 2. As will be appreciated, the minimal area of DNA that is "identical by descent" on all the ancestral HH chromosomes is between, but not including, markers 241-29 and 63-3, surrounding marker 241-5. This is the region within which the HH gene must lie and where we conducted our search for the gene as describe below.

3. Physical Mapping

Primary clone coverage of the genomic region telomeric of the MHC locus on Chromosome 6p was obtained by assembling an overlapping set of YAC clones that span the region between HLA-F and D6S276. Initial YAC contigs were seeded by screening the CEPH MegaYAC library for the sequence tag sites (STSs) D6S258, D6S306, D6S105, D6S464 and D6S276. Additional YACs containing these STSs were identified in the CEPH and the MIT/Whitehead databases. The three initial YAC contigs were expanded and eventually merged into a single contig by bidirectional walking using STSs developed from the ends of YAC inserts. An STS-content map comprising 64 STSs and 44 YACs across the HH region was constructed. In order to determine precise physical distances, a set of 14 YACs were selected for RARE-cleavage mapping (Gnirke et al. *Genomics* 24:199–210 (1994)) and the construction of the distance-calibrated YAC-contig and STS content maps which are shown in FIG. 1.

Bacterial clones were identified by PCR-based and hybridization-based screening of comprehensive human cosmid, p1, BAC, and PAC libraries. FIG. 1 also shows the bacterial clone contig across approximately 1 Mbp of genomic DNA that includes the region represented by YAC 241. The STS-content map indicating the STS and clone order is depicted in FIG. 1. YACs, BACs, PACs and P1 clones are denoted by the suffices y, b, pc and p, respectively.

In FIG. 1, the markers are characterized as follows: D6S248 (1); D6S265 (2); HLA-A (3); P6116 (4); HLA-F (5); MOG (6); D6S258 (2); 258-2 (3); RFP (3); H731-1 (7); H5091-1 (7); H4440-1 (7); H4440-2 (7); 4073-1 (7); G4 (3); 3321-1 (7); 19D9 (7); HHp61 (3); 18B4 (7); 1A2 (7); D6S306 (2); 2B8 (7) 1E.4 (7); 24E.2 (7); D6S1001 (8); HHp89 (3); D6S105 (9); D6S464 (2); H3216-1 (7); H4072-2 (7); H4073-3 (3); H950-2 (7); H950-3 (7); H950-4 (7); H950-8 (7); H950-6 (7); H950-1 (7); H241-4 (3); HB65-2 (7); H65-1 (7); H241-6 (3); H241-29 (7); H241-5 (7); 63-3 (7); 63-1 (7); HB63-2 (7); HB373-8 (7); D6S1281 (4); HB68-1 (7); and D6S276 (2).

1 Orphanos, V. et al. *Hum Mol Genet* 2:2196 (1993)
2 Gyapay, G. et al. *Nature Genetics* 7:246–339 (1994)
3 Unpublished STS's to genomic DNA developed by the Assignee of the present application.
4 Murray, J. C. et al. *Science* 265:2049–2054 (1994)
5 Fullan, A. and Thomas, W. *Hum Molec Genet.* 3:2266 (1994)
6 Roth, M-P. et al. *Genomics* 28:241–250 (1995)
7 CA repeats described in co-pending U.S. patent application Ser. No. 08/599,252, filed Feb. 9, 1996, which is a continuation-in-part of U.S. patent application Ser. No. 08/559,302, filed Nov. 15, 1995, which is a continuation-in-part of U.S. patent application Ser. No. 08/436,074, filed May 8, 1995, the disclosures of which are hereby incorporated by reference in their entirety.
8 Stone, C. et al. *Hum Molec Genet* 3:2043–2046 (1994)
9 Weber, J. L. et al. *Nucl. Acids Res.* 19:968 (1991).

The markers indicated at the top of FIG. 2 are those that are labeled with stars in FIG. 1. Other than marker 24d1, all of the markers indicated (i.e., 241-4, 96-1, 65-2, 65-1, 241-6, 241-29, 241-5, 63-3, 63-1, 63-2, 373-373-8, and 373-29) are CA repeat markers. The numbers indicated in the chart with respect to the CA repeat markers refers to the size of the allele upon PCR amplification and sizing of the resulting product on acrylamide gels. The 24d1 marker, as discussed above, is a single base-pair mutation as represented by the G to A base substitution that is present in affected chromosomes as illustrated in SEQ ID NO:29 and SEQ ID NO:30. The results of genotyping for each of the two chromosomes from the patients are indicated. DNA that is identical by descent is indicated by shading.

As will be appreciated, eight patient haplotypes displayed evidence of recombination events delineating the minimal HH region. The tract of DNA that is "identical by descent" on all of the ancestral HH chromosomes is between, but not including, markers 241-29 and 63-3. Genomic sequencing has determined this region to be 250 kb in size. This region includes markers 241-5 and 24d1. See FIG. 2, Patient HC75 and Patients HC2, HC22, HC50, HC87, HC91, HC125, and HC143.

4. Identification of cDNA 24

Based upon allelic association data, we delineated a region encompassed by YAC 241 as the region most likely to contain the HH gene. As one of our approaches to identify genes within the HH region, direct selection experiments were performed on YAC 241. Morgan, J. G. et al. *Nucl Acids Res* 20:5173–5179 (1992).

Briefly, YAC DNA was isolated by pulse-field gel electrophoresis, digested with Mbo I and linkers ligated to the resulting fragments. The DNA was then amplified by PCR using primers containing biotin on their 5' end. Similarly, cDNA was prepared from poly A+ RNA from fetal brain, small intestine and liver, digested with Mbo I, linkers ligated and amplified by PCR. The cDNA was 'blocked' with DNA clones representing human ribosomal RNA, histone genes as well as with repetitive DNA (Cot-1, Gibco).

Two rounds of solution hybridization were carried out to the prescribed value of Cot 100. The DNA fragments were cloned into pSP72 and sequenced. Four hundred and sixty-five clones were sequenced and arranged into 162 overlapping contigs, referred to herein as DS clones.

Representative sequences from each contig were searched against the public databases (NCBI) and interesting homologies were noted. One in particular, known as DS34 showed convincing homology to MHC Class I protein encoding genes. Small STSs were designed from each of the 162 nested set of primers were used to increase specificity in generating the three products. The primers utilized are shown in Table 1:

TABLE 1

| PCR Product | Name | Primer Set for 1st Nested PCR | Name | Primer Set for 2nd Nested PCR |
|---|---|---|---|---|
| "A" | P17 | 5'-CAA AAG AAG CGG AGA TTT AAC G-3' | P19 | 5'-AGA TTT AAC GGG GAC GTG C-3' |
|  | P18 | 5'-AGA GGT CAC ATG ATG TGT CAC C-3' | P20 | 5'-AGG AGG CAC TTG TTG GTC C-3' |
| "B" | P5 | 5'-CTG AAA GGG TGG GAT CAC AT-3' | P7 | 5'-AAA ATC ACA ACC ACA GCA AAG-3' |
|  | P6 | 5'-CAA GGA GTT CGT CAG GCA AT-3' | P8 | 5'-TTC CCA CAG TGA GTC TGC AG-3' |
| "C" | P9 | 5'-CAA TGG GGA TGG GAC CTA C-3' | P11 | 5'-ATA TAC GTG CCA GGT GGA GC-3' |
|  | P10 | 5'-CCT CTT CAC AAC CCC TTT CA-3' | P12 | 5'-CAT AGC TGT GCA ACT CAC ATC A-3' |

P17 (SEQ ID NO:31); P19 (SEQ ID NO:32); P18 (SEQ ID NO:33); P20 (SEQ ID NO:34); P5 (SEQ ID NO:18); P7 (SEQ ID NO:35); P6 (SEQ ID NO:19); P8 (SEQ ID NO:36); P9 (SEQ ID NO:37); P11 (SEQ ID NO:38); P10 (SEQ ID NO:39); and P12 (SEQ ID NO:40)

contigs and the contigs were mapped in relation to the existing STS content map of the region.

Clones that mapped to the delineated minimal HH region of YAC 241 were given priority for further analysis. In conjunction with its homology to MHC Class I genes, DS34 mapped within our minimal region, and thus was considered a candidate for the HH gene. The STSs were subsequently used to determine which cDNA library was appropriate for obtaining full length cDNA clones.

Three directionally cloned plasmid based cDNA libraries were employed (Gibco); brain, liver and testis. It was discovered that DS34 was present in all three libraries. Subsequently, DS34 was random prime labeled and used to screen colony lifts of cDNA libraries using standard procedures. Three clones were obtained from the testis library. The largest of these, 2.7 kb, was designated cDNA24 and was sequenced completely on both strands.

5. Mutation Analysis of cDNA24

The candidate gene encompassed in cDNA24 was analyzed to detect mutations in the HH affected chromosomes as compared to unaffected chromosomes.

In connection with this work, patient DNA and RNA was obtained as follows. Lymphoblastoid cell lines from random and HH affected individuals were established by transformation of peripheral blood mononuclear cells with Epstein-Barr Virus. Chromosomal DNA was purified from these cells by standard methods (Maniatis et al. *Molecular Cloning—A Laboratory Manual* (2nd Ed. pp. 9.14–9.22, Cold Spring Harbor Laboratory Press, New York (1989))). PolyA+ RNA was purified using Fast Track (Invitrogen).

Mutation analysis was accomplished as follows. Initial searching for the HH mutation in cDNA24 was accomplished through RT-PCR (reverse transcription-polymerase chain reaction, Dracopoli, N. et al. eds. *Current Protocols in Human Genetics* pp. 7.1–7.1.7 (J. Wiley & Sons, New York (1994)) method. First, from the genotype analysis, homozygous HH patients with the ancestral haplotype were identified (see previous sections). First strand cDNAs were synthesized through use of Superscript reverse transcriptase (Life Technologies) using polyA+ RNA from transformed lymphoblastoid cell lines from two homozygous ancestral patients (HC9 and HC14) and those from two unaffected individuals (NY8 and CEPH 11840) as templates.

From these first strand cDNAs, coding regions corresponding to the cDNA24 sequence were amplified into three overlapping PCR products (designated herein as A, B, and C) to facilitate efficient amplification and sequencing. A Amplified DNA products (PCR-products) were purified using gelase (Epicentre), and DNA sequences of these PCR-fragments were determined by the dideoxy chain termination method using fluorescently labeled dideoxy nucleotides on an ABI 377 DNA sequencer.

Comparison of DNA sequences derived from these PCR-fragments identified a single nucleotide change in the cDNA24 coding region as represented by SEQ ID NO:29 and SEQ ID NO:30 at nucleotide 845. (Note, the first nucleotide of the open reading frame was counted as nucleotide 1. See FIGS. 4A–4C). The nucleotide at this position in two unaffected individuals was a G, while two HH affected individuals had an A at this position.

This mutation was designated as 24d1. The allele containing a G at this position was named as 24d1(G) and the allele containing an A in this position was named 24d1(A). The mutation causes an amino acid change from a cysteine (Cys282) to a tyrosine. This cysteine residue is conserved in all the known Class I MHC molecules and contributes a sulfur to the formation of a disulfide bridge that is present in the immunoglobulin constant region like domain (Ig domain, Gussow et al. *Immunogenetics* 25:313–322 (1987); Bjorkman and Parham *Ann Rev Biochem* 59:253 (1990)). In the case of Class I MHC molecules, it has been shown that a similar change in the reciprocal cysteine involved in the disulfide bridge abolishes the function of the protein by causing a defect in cell surface expression (Miyazaki et al. *PNAS USA* 83:757–761 (1986)). Thus, due to the high degree of conservation seen in the structure, it is likely that the 24d1 mutation would interfere with the function of cDNA 24 protein products.

The genomic sequence surrounding the 24d1 mutation is provided in SEQ ID NO:29 (unaffected 24d1(G) allele) and SEQ ID NO:30 (affected 24d1(A) allele).

The frequency of the mutant 24d1(A) allele and the normal 24d1(G) allele was determined in random chromosomes and affected chromosomes through use of an oligonucleotide ligation assay (OLA assay). See Nickerson et al. *PNAS USA* 87:8923–8927 (1990). Chromosomal DNA from these individuals was prepared from either a lymphoblastoid cell line or peripheral blood cells. First, DNA corresponding to exon 4 was amplified by PCR using primers designed against intron DNA sequences flanking exon 4. See FIG. 6 which provides the precise location of the sequences used for primer design. The presence of the 24d1(A) allele or the 24d1(G) allele was determined by OLA using the oligonucleotides outlined in FIG. 5. FIG. 5 shows the sequences of preferred primers used for amplification and analysis of the above base mutation. The amplification primers for 24d1 are labeled 24d1.P1 (SEQ ID NO:13) and 24d1.P2 (SEQ ID NO:14). The oligonucleotides used in the sequence determination by OLA for 24d1 are designated 24d1.A (SEQ ID NO:15), 24d1.B (SEQ ID NO:16), and 24d1.X (SEQ ID NO:17). As indicated in the sequences shown, "bio" indicates biotin coupling, "p" indicates 5'-phosphate, and "dig" indicates coupled digoxigenin.

The result from this OLA assay with 164 HH affected individuals and 134 unaffected random individuals is shown in Table 2.

this variant are 24d2(C) (C at this position) and 24d2(G) (G at this position). CDNA24 as well as NY8 and CEPH 11840 were homozygous for the 24d2(C) allele, while DNAs from some patients (HC74, HC82 and others) were 24d2(C)/24d2 (G) heterozygous. The 24d2(C) allele encodes a histidine (His63) while 24d2(G) encodes an aspartic acid, thus creating an amino acid change in the presumed peptide binding domain of the protein product. As with 24d1, changes to certain amino acids in the peptide binding domains of MHC Class I proteins can also disrupt intracellular transport and assembly (Salter *Immunogenetics* 39:266–271 (1994)).

The genomic sequence surrounding the variant for 24d2 (C) and 24d2(G) is provided below:

24d2(C):

AGCTGTTCGTGTTCTATGAT C ATGAGAGTCGCCGT-GTGGA   (SEQ ID NO:41)

24d2(G):

AGCTGTTCGTGTTCTATGAT G ATGAGAGTCGCCGT-GTGGA   (SEQ ID NO:42)

TABLE 2

Frequencies of Alleles as % of Chromosomes Tested

|  | Affected Chromosomes (N = 328) | Random Chromosomes (N = 268) |
|---|---|---|
| 24d1 "A" | 86% | 4% |
| 24d1 "G" | 14% | 96% |

The 24d1(A) mutation occurs in 86% of the chromosomes from HH affected individuals (affected chromosomes) as compared to 4% in the chromosomes from random individuals (random chromosomes). This approximates the estimated frequency of the ancestral HH mutation in the general population. Among these 164 affected individuals, 137 were homozygous for the 24d1(A) allele and 8 were heterozygous for the 24d1(A) and the 24d1(G) alleles, while the remaining 19 were homozygous for the 24d1(G) allele. The distribution of homozygotes and heterozygotes for the 24d1 alleles significantly deviates from that expected by Hardy-Weinberg equilibrium, suggesting the possibility of either mutant alleles that complement one another or genetic heterogeneity. Regardless, of this fact, 24d1 homozygosity provides identification of 84% of HH patients in our sample.

In addition to the 24d1 mutation, other sequence variants were also detected within certain subpopulations of patients. In this regard, sequence analysis of the cDNA24 gene was extended to the remaining individuals who are either 24d1 (G) homozygotes or 24d1(A)/24d1(G) heterozygotes. Nineteen 24d1(G) homozygous HH patient and eight 24d1 heterozygotes patients were analyzed. All the exons that contain the cDNA24 open reading frame were amplified from these individuals through the use of PCR primers directed against introns and exons. DNA sequences of these PCR products were determined by dideoxy chain termination methods. This analysis identified two additional sequence variants (24d2 and 24d7) in the coding region of cDNA24, The first additional variant, 24d2, occurs at nucleotide 187. (Note, the first nucleotide of the open reading frame was counted as nucleotide 1. See FIG. 4). The two alleles of The frequency of the 24d2 mutant allele versus the normal allele was determined through OLA as described above. The results from the OLA assays are shown in Table 3.

TABLE 3

Frequencies of Alleles as % of Chromosomes Tested

|  | Affected Chromosomes (N = 328) | Random Chromosomes (N = 158) |
|---|---|---|
| 24d2 "C" | 95% | 18% |
| 24d2 "G" | 5% | 82% |

As shown in Table 3, the 24d2(G) allele occurs in 5% of the chromosomes from HH affected individuals (affected chromosomes) and in 18% of the chromosomes from random individuals (random chromosomes). The frequency of the 24d2(G) allele in the patients was lower than that of random chromosomes because this allele was associated with some of the nonancestral chromosomes and the majority of the HH patient chromosomes were ancestral. The remainder of the chromosomes had the 24d2(C) allele. When one looks at the distribution of the 24d2(G) allele containing chromosomes within the patient population, one notices an enrichment of the 24d2(G) allele in 24d1 heterozygotes. Seventy five percent or 6 out of 8 heterozygotes for 24d1 have the 24d2(G) allele as compared to the expected 18%. Thus, the 24d2(G) allele is enriched in 24d1 heterozygous patients indicating that the 24d2 mutation has a role in HH disease.

A third nucleotide change was identified at nucleotide 193 in one patient (HC43) and was named 24d7, (Note, the first nucleotide of the open reading frame was counted as nucleotide 1. See FIG. 4). All other patients analyzed, as well as random controls, including NY8 and CEPH 11840 had an allele 24d7(A) (A at this position), while HC43 was a 24d7(A)/24d7(T) heterozygote. The 24d7(A) allele encodes a serine (Ser65) while the 24d7(T) allele changes this to a cysteine codon, also within the presumed peptide binding domain of the cDNA 24 protein product.

The genomic sequence surrounding the polymorphism for 24d7(A) and 24d7(T) is provided below:

24d7(A):
            TGTTCTATGATCATGAG A GTCGCCGTGTG- (SEQ ID NO:43)
GAG
(SEQ ID NO:43)
24d7(T):
            TGTTCTATGATCATGAG TGTCGCCGTGTGGAG (SEQ ID NO:44)

The frequency of the 24d7 mutant allele versus normal allele was determined through OLA as described above. The results from the OLA assays are shown in Table 4.

TABLE 4

Frequencies of Alleles as % of Chromosomes Tested

|  | Affected Chromosomes (N = 266) | Random Chromosomes (N = 156) |
| --- | --- | --- |
| 24d7 "A" | 99.6% | 97% |
| 24d7 "T" | 0.4% | 3% |

In Table 4, the 24d7(T) allele was observed in only one chromosome present in the patient sample (HC43) (0.4%) and present in four chromosomes from the unaffected individuals (3%). The presence of the 24d7(T) allele shows no increase in risk of acquiring HH and thus may only be a polymorphic variant within the population.

B. Characteriztion of the HH Gene
1. Sequence

The complete sequence of cDNA24 (of which the coding region is shown in FIGS. 4A–4C) was used to search public databases (NCBI) for homology to known gene sequences using the BlastX search algorithm. Substantial homology to MHC Class I molecules from a variety of species was obtained.

Next, the sequence was analyzed for the existence of open-reading frames (ORF's). The largest ORF, as shown in FIGS. 4A–4C, encodes a polypeptide of 348 amino acids with a predicted molecular mass of approximately 38 KD. As will be appreciated, the molecular weight/mass can vary due to possible substitutions or deletions of certain amino acid residues. In addition, the molecular weight/mass of the polypeptide can vary due to the addition of carbohydrate moieties and in connection with certain phosphorylation events and other post-translational modifications. The remainder of the cDNA, 1.4 kb appears to be non-coding; one poly A addition site (AATAAA) is present 20 bp upstream of the poly A tail (not shown in FIGS. 4A–4C).

A search of translated public database (NCBI) using a six way translation of cDNA24 showed significant homology between cDNA 24 and previously cloned MHC proteins. The search revealed 39% identity and 58% similarity of the amino acid residues. Besides MHC Class I proteins, the HH gene product shows similarity to other proteins known to contain motifs related to the immunoglobulin constant region, such as β-2-microglobulin and zinc-α-2-glycoprotein. See Bjorkman, P. and Parham, P. *Ann Rev Biochem* 59:253 (1990). A multiple sequence alignment was carried out between several MHC Class I proteins (FIG. 7). The results indicate that the homology between cDNA 24 and MHC extends throughout the cDNA 24 protein, including the peptide-binding region, immunologbulin-like region, transmembrane region and cytoplasmic region. Of particular interest is the conservation of the position of several cysteine residues which function in protein folding via disulfide bonds.

cDNA 24 tissue expression was determined by probing polyA+ RNA Northern blots (Clontech). One major transcript of approximately 4.4 kb was observed in all of the 16 tissues tested including small intestine and liver.

The genomic region corresponding to cDNA 24 was cloned and sequenced. CDNA 24 is comprised of seven exons, covering approximately 12 kb of sequence. The seventh exon is completely non-coding and contains one poly (A)+ addition signal. In the region of the predicted start site of transcription, there are no consensus CAAT or TATA boxes, nor are there any start like βGAP-like sequences recently suggested by Rothenberg and Voland, supra (1996). One CpG island was found to overlap the first exon and extend into the first intron. Within this island are the consensus cis-acting binding sites for the transcription factors Sp1 (2 sites) and AP1 (1 site) (Mac Vector software, Oxford Molecular). The lack of any recognizable TATA boxes and the presence of Sp1 and AP2 binding sites is consistent with the low level of transcription associated with the gene.

2. Structure/Function of the HH Gene Product

The predicted translation product of cDNA 24, herein referred to as the HH gene and HH gene product or HH protein, was aligned to other MHC proteins for which there was a high degree of homology at the amino acid level (FIG. 7). MHC Class I proteins are comprised of several distinct domains: peptide binding domains (α1 and α2), immunoglobulin like domain (α3), a transmembrane region, and a small cytoplasmic portion. The HH gene product shows homology throughout all four of these domains. Further confirmation of the structural relationship between the HH gene product and MHC Class I molecules was obtained through analysis of the primary sequence using Mac Vector software (Oxford Molecular).

The HH gene product is similar to MHC Class 1 molecules when comparing hydrophilicity, surface probability, and secondary structure. A conserved structural feature of Class 1 molecules is the presence of several intradomain disulfide bonds between positions Cys-101 and Cys-164 in the α2 helix and between Cys-203 and Cys-259 in the α3 helix. This domain structure is conserved between all Class 1 molecules. The disulfide bond in the α3 helix forms the interface through which the molecule interacts with the β-2-microglobulin protein, a protein which associates with MHC Class 1 molecules in the endoplasmic reticulum and functions as a molecular chaperone.

The HH protein possesses all four cysteine residues in conserved positions common to MHC Class I molecules. This data indicates a structural relationship with MHC Class I Molecules and a potential interaction with β-2-microglobulin (or a related protein) as well.

It has been demonstrated that when the cysteine at position 203 is mutated, thus disrupting the disulfide bridge that is formed between Cys-203 and Cys-259, intracellular transport of the mutated protein is blocked. See Miyazaki et al. supra (1986). As will be appreciated, the mutation (24d1) of the present invention corresponds to the reciprocal Cysteine (Cys-259; Cys-282 in the HH protein) in the disulfide bridge that was demonstrated by Miyazaki et al. to abolish intracellular transport. Thus, it is predicted that the 24d1 mutation ablates expression of the HH protein on cell surfaces.

Sequence studies of MHC Class I molecules have shown that these molecules are among of the most polymorphic proteins known to date. The majority of this variation is located in the α1 and α2 domains of the molecule. In contrast, the HH gene product displays little polymorphism in this region. In this respect, the HH protein is more similar to the non-classical MHC class of proteins which show little or no allelic variation. The functions of the non-classical MHC Class I proteins, such as HLA-E, F, and G proteins, are unknown, although HLA-G may play a role in maternal/fetal immune interactions. Campbell, R. D. and Trousdale, *J. Immunology Today* 14:349 (1993).

Therefore, the HH protein differs from MHC Class I molecules in one very important respect. Although it has maintained all of the structural hallmarks of MHC Class I molecules, it does not appear to be polymorphic and has presumably evolved a different function. This function appears to be participation in the control of body iron levels, for example, through the direct binding of free iron, binding of other iron-bound proteins, or signaling involved in regulation of iron levels. Iron-bound proteins or other proteins involved in signaling could associate with the HH protein in a manner similar to β-2-microglobulin or could be bound in the peptide-binding region of the protein.

In addition, the protein could exert it's effects by indirectly regulating iron adsorption through intercellular signaling, i.e., T-cell activation and subsequent specific cell proliferation via cytokine release. Directly related to our discovery of the gene responsible for HH is the data of de Sousa et al. (*Immun Lett* 39:105–111 (1994)). Analysis of previously constructed, β-2-microglobulin knockout mice indicated that mice homozygous for the defect progressively accumulated iron in a manner indistinguishable from human hemochromatosis. These mice also mimic an additional phenotype observed in HH patients, an abnormally low number of CD8+ T cells. Therefore, β-2-microglobulin knock-out mice possess two characteristics of human HH, iron loading of the internal organs and a defective T cell repertoire. Clearly, β-2-microglobulin which maps to Chromosome 15 is not responsible for HH. However, β-2-microglobulin knock-out mice could phenocopy HH by preventing the associated murine HH homolog of cDNA 24 from assuming it's functional structure and presentation on the surface of cells.

In conclusion, the HH gene encodes a protein with striking similarity to MHC Class I proteins. The gene product has maintained a structural feature essential for proper and functional recognition of a chaperone protein (β-2- microglobulin) whose disruption in mice causes a phenocopy of HH disease. Finally, the mutation identified in the HH gene leads to the ablation of cell surface expression in other model systems.

3. Protein Purification

The HH protein can be purified by one of several methods which have been selected based upon the molecular properties revealed by its sequence and its homology to MHC Class I molecules. Since the molecule possesses properties of an integral membrane protein, i.e. contains a transmembrane domain, the protein must first be isolated from the membrane fraction of cells using detergent solubilization. A variety of detergents useful for this purpose are well known in the art.

Once solubilized, the HH protein can be further purified by conventional affinity chromatography techniques. The conventional approaches of ion exchange, hydrophobic interaction, and/or organomercurial chromatographies can be utilized. These methodologies take advantage of natural features of the primary structure, such as: charged amino acid residues, hydrophobic transmembrane domains, and sulfhydryl-containing cysteine residues, respectively. In the affinity chromatography approach use is made of immunoaffinity ligands or of the proposed interaction of the HH protein with β-2-microglobulin, calnexin or similar molecules. In the former, the affinity matrix consists of antibodies (polyclonal or monoclonal) specific to the HH protein coupled to an inert matrix. The production of antibodies specific to the HH protein are described in Section (III)(A) (3), entitled "Antibodies". In the latter method, various ligands which are proposed to specifically interact with the HH protein based on its homology with MHC Class I molecules could be immobilized on an inert matrix. For example, β-2-microglobulin, β-2-microglobulin-like molecules, or other specific proteins such as calnexin or calnexin-like molecules, and the like, or portions and/or fragments thereof, can be utilized. General methods for preparation and use of affinity matrices are well known in the art.

Criteria for the determination of the purity of the HH protein include those standard to the field of protein chemistry. These include N-terminal amino acid determination, one and two-dimensional polyacrylamide gel electrophoresis, and silver staining. The purified protein is useful for use in studies related to the determination of secondary and tertiary structure, as aid in drug design, and for in vitro study of the biological function of the molecule.

III. Applications

A. HH Screening

With knowledge of the primary mutation of the HH gene as disclosed herein, screening for presymptomatic homozygotes, including prenatal diagnosis, and screening for heterozygous carriers can be readily carried out.

1. General

There are four levels at which the diagnostic information from the HH gene can be used. The first is to assist in the medical diagnosis of a symptomatic patient. In this application, a patient with a high index of suspicion for being affected with HH could be tested with the gene-based diagnostic. A positive result would show that the individual was homozygous for the common HH mutation. This would provide a rapid and non-invasive confirmation that the individual corresponded to the fraction of the population homozygous for this mutation. Such a result would help rule out other causes of iron overload in that individual.

The second level of application would be in first degree relatives of newly diagnosed probands. Current recommended medical practice is to screen all such first degree relatives, as they are at a higher risk for disease and, if identified, could benefit from therapeutic intervention. The present invention together with previously described genetic markers disclosed and claimed in the co-pending patent applications discussed above, allows a gene-based test that would enable screening of individuals substantially non-invasively and accurately.

The third level of screening would be in individuals afflicted with diseases that are known to be sequelae of HH disease. Such diseases include cirrhosis of the liver, diabetes, arthritis, reproductive dysfunction, and heart disease. It has been estimated, for example, that as many as 1% of individuals with diabetes may be so afflicted because of HH disease. When secondary to HH disease, some of the pathology of these diseases can be reversed upon phlebotomy therapy. Therefore, it will be beneficial to perform screening with gene-based diagnostics in these disease populations.

The fourth level of screening is to screen the general population for homozygotes. Several cost-benefit analyses have suggested that there is value in such screenings for the identification of presymptomatic individuals. Once identified, such individuals could be targeted for preventative phlebotomy.

2. Nucleic Acid Based Screening

Individuals carrying mutations in the HH gene may be detected at either the DNA, the RNA, or the protein level using a variety of techniques that are well known in the art. The genomic DNA used for the diagnosis may be obtained from body cells, such as those present in peripheral blood, urine, saliva, bucca, surgical specimen, and autopsy specimens. The DNA may be used directly or may be amplified enzymatically in vitro through use of PCR (Saiki et al. *Science* 239:487–491 (1988)) or other in vitro amplification methods such as the ligase chain reaction (LCR) (Wu and Wallace *Genomics* 4:560–569 (1989)), strand displacement amplification (SDA) (Walker et al. *PNAS USA* 89:392–396 (1992)), self-sustained sequence replication (3SR) (Fahy et al. *PCR Methods Appl.* 1:25–33 (1992)), prior to mutation analysis. The methodology for preparing nucleic acids in a form that is suitable for mutation detection is well known in the art.

The detection of mutations in specific DNA sequences, such as the HH gene, can be accomplished by a variety of methods including, but not limited to, restriction-fragment-length-polymorphism detection based on allele-specific restriction-endonuclease cleavage (Kan and Dozy *Lancet* ii:910–912 (1978)), hybridization with allele-specific oligonucleotide probes (Wallace et al. *Nucl Acids Res* 6:3543–3557 (1978)), including immobilized oligonucleotides (Saiki et al. *PNAS USA* 86:6230–6234 (1989)) or oligonucleotide arrays (Maskos and Southern *Nucl Acids Res* 21:2269–2270 (1993)), allele-specific PCR (Newton et al. *Nucl Acids Res* 17:2503–2516 (1989)), mismatch-repair detection (MRD) (Faham and Cox *Genome Res* 5:474–482 (1995)), binding of MutS protein (Wagner et al. *Nucl Acids Res* 23:3944–3948 (1995), denaturing-gradient gel electrophoresis (DGGE) (Fisher and Lerman et al. *PNAS USA* 80:1579–1583 (1983)), single-strand-conformation-polymorphism detection (Orita et al. *Genomics* 5:874–879 (1983)), RNAase cleavage at mismatched base-pairs (Myers et al. *Science* 230:1242 (1985)), chemical (Cotton et al. *PNAS USA* 85:4397–4401 (1988)) or enzymatic (Youil et al. *PNAS USA* 92:87–91 (1995)) cleavage of heteroduplex DNA, methods based on allele specific primer extension (Syvänen et al. *Genomics* 8:684–692 (1990)), genetic bit analysis (GBA) (Nikiforov et al. *Nucl Acids Res* 22:4167–4175 (1994)), the oligonucleotide-ligation assay (OLA) (Landegren et al. *Science* 241:1077 (1988)), the allele-specific ligation chain reaction (LCR) (Barrany *PNAS USA* 88:189–193 (1991)), gap-LCR (Abravaya et al. *Nucl Acids Res* 23:675–682 (1995)), and radioactive and/or fluorescent DNA sequencing using standard procedures well known in the art.

As will be appreciated, the mutation analysis may also be performed on samples of RNA by reverse transcription into cDNA therefrom. Furthermore, mutations may also be detected at the protein level using antibodies specific for the mutant and normal HH protein, respectively. It may also be possible to base an HH mutation assay on altered cellular or subcellular localization of the mutant form of the HH protein.

3. Antibodies

As mentioned above, antibodies can also be used for the screening of the presence of the HH gene, the mutant HH gene, and the protein products therefrom. In addition, antibodies are useful in a variety of other contexts in accordance with the present invention. As will be appreciated, antibodies can be raised against various epitopes of the HH protein. Such antibodies can be utilized for the diagnosis of HH and, in certain applications, targeting of affected tissues.

Thus, in accordance with another aspect of the present invention a kit is provided that is suitable for use in screening and assaying for the presence of the HH gene by an immunoassay through use of an antibody which specifically binds to a gene product of the HH gene in combination with a reagent for detecting the binding of the antibody to the gene product.

Antibodies raised in accordance with the invention can also be utilized to provide extensive information on the characteristics of the protein and of the disease process and other valuable information which includes but is not limited to:

1. Antibodies can be used for the immunostaining of cells and tissues to determine the precise localization of the protein. Immunofluorescence and immuno-electron microscopy techniques which are well known in the art can be used for this purpose. Defects in the HH gene or in other genes which cause an altered localization of the HH protein are expected to be localizable by this method.

2. Antibodies to distinct isoforms of the HH protein (i.e., wild-type or mutant-specific antibodies) can be raised and used to detect the presence or absence of the wild-type or mutant gene products by immunoblotting (Western blotting) or other immunostaining methods. Such antibodies can also be utilized for therapeutic applications where, for example, binding to a mutant form of the HH protein reduces the consequences of the mutation.

3. Antibodies can also be used as tools for affinity purification of HH protein. Methods such as immunoprecipitation or column chromatography using immobilized antibodies are well known in the art and are further described in Section (II)(B)(3), entitled "Protein Purification" herein.

4. Immunoprecipitation with specific antibodies is useful in characterizing the biochemical properties of the HH protein. Modifications of the HH protein (i.e., phosphorylation, glycosylation, ubiquitization, and the like) can be detected through use of this method. Immunoprecipitation and Western blotting are also useful for the identification of associating molecules that are involved in signal transduction processes which regulate iron transport or other metabolic functions important in the HH disease process.

5. Antibodies can also be utilized in connection with the isolation and characterization of tissues and cells which express HH protein. For example, HH protein expressing cells can be isolated from peripheral blood, bone marrow, liver, and other tissues, or from cultured cells by fluorescence activated cell sorting (FACS) Harlow et al., eds., *Antibodies: A Laboratory Manual*, pp. 394–395, Cold Spring Harbor Press, NY (1988)). Cells can be mixed with antibodies (primary antibodies) with or without conjugated dyes. If non-conjugated antibodies are used, a second dye-conjugated antibody (secondary antibody) which binds to the primary antibody can be added. This process allows the specific staining of cells or tissues which express the HH protein.

Antibodies against the HH protein are prepared by several methods which include, but are not limited to:

1. The potentially immunogenic domains of the protein are predicted from hydropathy and surface probability profiles. Then oligopeptides which span the predicted immunogenic sites are chemically synthesized. These oligopeptides can also be designed to contain the specific mutant amino acids to allow the detection of and discrimination between the mutant versus wild-type gene products. Rabbits or other animals are immunized with the synthesized oligopeptides coupled to a carrier such as KLH to produce anti-HH protein polyclonal antibodies. Alternatively, monoclonal antibodies can be produced against the synthesized oligopeptides using conventional techniques that are well known in the art Harlow et al., eds., *Antibodies: A Laboratory Manual*, pp. 151–154, Cold Spring Harbor Press, NY (1988)). Both in vivo and in vitro immunization techniques can be used. For therapeutic applications, "humanized" monoclonal antibodies having human constant and variable regions are often preferred so as to minimize the immune response of a patient against the antibody. Such antibodies can be generated by immunizing transgenic animals which contain human immunoglobulin genes. See Jakobovits et al. *Ann NY Acad Sci* 764:525–535 (1995).

2. Antibodies can also be raised against expressed HH protein products from cells. Such expression products can include the full length expression product or parts or fragments thereof. Expression can be accomplished using conventional expression systems, such as bacterial, baculovirus, yeast, mammalian, and other overexpression systems using conventional recombinant DNA techniques. The proteins can be expressed as fusion proteins with a histidine tag, glutathione-S-transferase, or other moieties, or as nonfused proteins. Expressed proteins can be purified using conventional protein purification methods or affinity purification methods that are well known in the art. Purified proteins are used as immunogens to generate polyclonal or monoclonal antibodies using methods similar to those described above for the generation of antipeptide antibodies.

In each of the techniques described above, once hybridoma cell lines are prepared, monoclonal antibodies can be made through conventional techniques of priming mice with pristane and interperitoneally injecting such mice with the hybrid cells to enable harvesting of the monoclonal antibodies from ascites fluid.

In connection with synthetic and semi-synthetic antibodies, such terms are intended to cover antibody fragments, isotype switched antibodies, humanized antibodies (mouse-human, human-mouse, and the like), hybrids, antibodies having plural specificities, fully synthetic antibody-like molecules, and the like.

B. Molecular Biology

1. Expression Systems

"Expression systems" refer to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein "cell", "cell line", and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell, are included. Where distinct designations are intended, it will be clear from the context.

In general terms, the production of a recombinant form of HH gene product typically involves the following:

First a DNA encoding the mature (used here to include all normal and mutant forms of the proteins) protein, the preprotein, or a fusion of the HH protein to an additional sequence cleavable under controlled conditions such as treatment with peptidase to give an active protein, is obtained. If the sequence is uninterrupted by introns it is suitable for expression in any host. If there are introns, expression is obtainable in mammalian or other eukaryotic systems capable of processing them. This sequence should be in excisable and recoverable form. The excised or recovered coding sequence is then placed in operable linkage with suitable control sequences in an expression vector. The construct is used to transform a suitable host, and the transformed host is cultured under selective conditions to effect the production of the recombinant HH protein. Optionally the HH protein is isolated from the medium or from the cells and purified as described in Section (II)(B)(3), entitled "Protein Purification".

Each of the foregoing steps can be done in a variety of ways. For example, the desired coding sequences can be obtained by preparing suitable cDNA from cellular mRNA and manipulating the cDNA to obtain the complete sequence. Alternatively, genomic fragments may be obtained and used directly in appropriate hosts. The construction of expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, prokaryotic, yeast, insect, or mammalian cells are presently useful as hosts. Prokaryotic hosts are in general the most efficient and convenient for the production of recombinant proteins. However, eukaryotic cells, and, in particular, mammalian cells, are often preferable because of their processing capacity and post-translational processing of human proteins.

Prokaryotes most frequently are represented by various strains of *E. coli*. However, other microbial strains may also be used, such as *Bacillus subtilis* and various species of Pseudomonas or other bacterial strains. In such prokaryotic systems, plasmid or bacteriophage vectors which contain origins of replication and control sequences compatible with the host are used. A wide variety of vectors for many prokaryotes are known (Maniatis et al. *Molecular Cloning: A Laboratory Manual* pp. 1–54 (Cold Spring Harbor Laboratory, Cold Spring Harbor, N.Y. (1982)); Sambrook et al. *Molecular Cloning: A Laboratory Manual* pp. 1.3–1.11, 2.3–2.125, 3.2–3.48, 4.2–4.64 (Cold Spring Harbor Laboratory, Cold Spring Harbor, N.Y. (1989)); *Meth. Enzymology* 68:357–375 (1979); 101:307–325 (1983); 152:673–864 (1987). (Academic Press, Orlando, Fla.; Pouwells et al. *Cloning Vectors: A Laboratory Manual* (Elsevier, Amsterdam (1987))). Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems, the tryptophan (trp) promoter system and the lambda derived PL promoter and N-gene ribosome binding, site, which has become useful as a portable control cassette (U.S. Pat. No. 4,711,845). However, any available promoter system compatible with prokaryotes can be used (Maniatis et al. supra. (1982); Sambrook et al. supra. (1989); *Meth. Enzymology supra.* (1979, 1983, 1987); John et al. *Gene* 61:207–215 (1987)) supra. (1987)).

In addition to bacteria, eukaryotic microbes, such as yeast, may also be used as hosts. Laboratory strain *Saccharomyces cerevisiae* or Baker's yeast, is most often used although other strains are commonly available.

Vectors employing the 2 micron origin of replication and other plasmid vectors suitable for yeast expression are known (Maniatis et al. supra. (1982); Sambrook et al. supra. (1989); *Meth. Enzymology supra.*; John et al. supra. Control sequences for yeast vectors include promoters for the synthesis of glycolytic enzymes. Additional promoters known in the art include the promoters for 3-phosphoglycerate kinase, and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization. See Maniatis et al. supra. (1982); Sambrook et al. supra. (1989); *Meth. Enzymology supra.*; John et al. supra. It is also believed that terminator sequences at the 3' end of the coding sequences are desirable. Such terminators are found in the 3' untranslated region following the coding sequences in yeast-derived genes. Many of the useful vectors contain control sequences derived from the enolase gene containing plasmid peno46 or the LEU2 gene obtained from Yep13, however, any vector containing a yeast compatible promoter, origin of replication, and other control sequences is suitable (Maniatis et al. supra. (1982); Sambrook et al. supra. (1989); *Meth. Enzymology supra.* (1979, 1983, 1987); John et al. supra.

It is also, of course, possible to express genes encoding polypeptides in eukaryotic host cell cultures derived from multicellular organisms (Kruse and Patterson *Tissue Culture* pp.475–500 (Academic Press, Orlando (1973)); *Meth. Enzymology* 68:357–375 (1979); Freshney *Culture of Animal Cells: A Manual of Basic Techniques* pp.329–334 (2d ed., Alan R. Liss, NY (1987))). Useful host cell lines include murine myelomas N51, VERO and HeT cells, SF9 or other insect cell lines, and Chinese hamster ovary (CHO) cells. Expression vectors for such cells ordinarily include promoters and control sequences compatible with mammalian cells such as, for example, the commonly used early and later promoters from Simian Virus 40 (SV 40), or other viral promoters such as those from polyoma, adenovirus 2, bovine papilloma virus, or avian sarcoma viruses, herpes virus family (such as cytomegalovirus, herpes simplex virus, or Epstein-Barr virus), or immunoglobulin promoters and heat shock promoters (Maniatis et al. supra. pp.405–410 (1982); Sambrook et al. supra. pp.16.3–16.74 (1989); *Meth. Enzymology* 152:684–704 (1987) John et al. supra. In addition, regulated promoters, such as metallothionine (i.e., MT-1 and MT-2), glucocorticoid, or antibiotic gene "switches" can be used.

General aspects of mammalian cell host system transformations have been described by Axel (U.S. Pat. No. 4,399, 216). It now appears also that "enhancer" regions are important in optimizing transformation. Generally, "enhancer" regions are sequences found upstream of the promoter region. Origins of replication may be obtained, if needed, from viral sources. However, integration into the chromosome is a common mechanism for DNA replication in eukaryotes. Plant cells are also now available as hosts, and control sequences compatible with plant cells such as the nopaline synthase promoter and polyadenylation signal sequences are available (Pouwells et al. supra. (1987); *Meth Enzymology* 118:627–639 (Academic Press, Orlando (1986)); Gelvin et al. *J. Bact.* 172:1600–1608 (1990).

Depending on the host cell used, transformation is done using standard techniques appropriate to such cells (Maniatis et al. supra. pp.249–255 (1982); Sambrook et al. supra. pp.16.30–16.5 (1989); *Meth. Enzymology supra.* 68:357–375 (1979); 101:307–325 (1983); 152:673–864 (1987); U.S. Pat. No. 4,399,216; *Meth Enzymology supra* 118:627–639 (1986); Gelvin et al. *J. Bact.* 172:1600–1608 (1990). Such techniques include, without limitation, calcium treatment employing calcium chloride for prokaryotes or other cells which contain substantial cell wall barriers; infection with *Agrobactetium tumefaciens* for certain plant cells; calcium phosphate precipitation, DEAE, lipid transfection systems (such as Lipofectin™ and Lipofectamine™), and electroporation methods for mammalian cells without cell walls, and, microprojectile bombardment for many cells including, plant cells. In addition, DNA may be delivered by viral delivery systems such as retroviruses or the herpes family, adenoviruses, baculoviruses, or semliki forest virus, as appropriate for the species of cell line chosen.

C. Function Experiments

Expression systems for the HH gene product, for example as described in the previous Section, allow for the study of the function of the HH gene product, in either normal or wild-type form and/or mutated form. Such analyses are useful in providing insight into the disease causing process that is derived from mutations in the gene. Judging from the sequence similarity of the HH gene to MHC Class I molecules, the HH gene product is expected to be expressed on cell surfaces.

1. Analysis of Iron Metabolism

The HH gene (mutated, normal, or wild-type) can be utilized in an assay of iron metabolism. The gene is expressed, with or without any accompanying molecules, in cells lines or primary cells derived from HH patients, healthy individuals, or cells from other organisms (such as rodents, insects, bacteria, amphibians, etc.). Uptake of iron by these cells is measured, for example through the use of radioactive isotopes. Further, binding of iron to the HH gene product can also be measured. Such experiments assist in assessing the role of the HH gene and HH gene product in iron uptake, binding, and transport by and in cells.

2. Analysis of Lead and Other Metal Metabolism

Increased accumulation of lead and certain other metals has been reported in HH homozygotes. See Barton et al. *J Lab Clin Med* 124:193–198 (1994). As discussed above in connection with iron, the metabolism of lead and other metals can be assessed.

3. Analysis of MHC Function

As discussed above, the HH gene products share significant structural similarity with Class I MHC molecules. Class I MHC molecules have several well known and measurable activities. Expression of the HH gene products through the use of appropriate expression systems allows for the analysis of whether the HH gene products possess similar activities.

a. Peptide Presentation Assay

Peptide presentation can be measured through use of a number of well known techniques. One method is to express the HH gene product on the surface of mammalian cells. Thereafter, the HH gene product can be purified from the cell surface analyzed for peptide binding, through, for example, high performance liquid chromatography (HPLC) after elution. Amino acid sequences of any bound peptides can be determined through conventional sequencing techniques (i.e., Edman degradation).

Another technique to analyze peptide presentation is to express the HH gene product on a cell that does not conventionally possess peptide presentation activity (i.e., *Drosophila melanogaster* derived Schneider cells. See Rammensee et al. *Ann Rev Immunol* 11:213–244 (1993). In such a system, MHC Class I molecules are expressed on the cell surface "empty" (i.e., without any bound peptide). Thereafter, through the addition of a particular peptide to the system, the binding of the particular peptide to the empty Class I molecule can be measured. See Rammensee et al. supra. (1993). A similar assay can be utilized in connection with the HH gene products.

b. T-cell Activation and Activation of Other Cells

It has been observed that, in at least some HH patients, there is a decrease in the numbers of CD8+ T-cells. (Reimao et al. *C. R. Acad Sci Paris* 313:481 (1991)). This is a striking phenotype as a similar phenotype is associated with the β-2-microglobulin knock-out mice (Koller et al. *Science* 248:1127 (1990); Zijlstra et al. *Nature* 344:742 (1990)). The role of MHC Class I proteins in the development of the T-cell repertoire is well documented. See Doherty *Adv Immun* 27:51 (1979). Animals lacking CD8+ T-cells would be expected to be more susceptible to a variety of infections and cancers. The β-2-microglobulin knock-out mice have been kept under pathogen-free conditions so that the long-term consequences of lacking CD8+ T-cells has not been ascertained. Humans, however, when deficient in CD8+ T-cells, have shown several conditions that are consistent with a compromised immune system, most notably a 200 fold increase in the incidence of hepatocellular carcinomas. See Niederau et al. *N Engl J Med* 313:1256 (1985).

Further, it is known that Class I MHC molecules are involved in the activation and differentiation of T-cells through the interaction between MHC molecules and α/β, or γ/δ T-cell receptors. Methods to measure T-cell activation are well known in the art. See Schild et al. *Cell* 76:29–37 (1994) and others). Signaling events in other cell types can also be measured. See Leibson *Immunity* 3:5–8 (1995). Thus, expression of the HH gene product on cells that are co-cultured with various T-cells can be used as an assay to measure T-cell differentiation and activation induced by the HH gene product. In particular, as mentioned above, differentiation and activation of CD8+ T-cells can be determined and measured and the role of the normal and mutant HH gene and gene products therein assessed.

c. Identification of Downstream Cells

The assays described above can be utilized to monitor and determine other cellular interactions between "downstream cells" and the HH gene protein product. Cells that interact with the HH gene protein product can be analyzed for uptake of iron and iron binding as described above.

d. Determination of Cellular Markers

As discussed above, it is predicted that the HH gene product is expressed and presented on cell surfaces. As such, the HH gene product can be utilized as a cell surface marker and detected through the use of FACS, as discussed in the Section entitled "Antibodies", above.

D. Therapeutics

Identification of the HH gene and its gene product also has therapeutic implications. Indeed, one of the major aims of the present invention is the development of therapies to circumvent or overcome the defect leading to HH disease. Envisioned are pharmacological, protein replacement, antibody therapy, and gene therapy approaches. In addition, the development of animal models useful for developing therapies and for understanding the molecular mechanisms of HH disease are envisioned.

Peptide binding domains of MHC molecules have ligands, or are known to bind ligands, and we expect that the HH protein may directly bind iron or other metals or bind to a ligand (such as a peptide) that binds iron or other metals. Therefore, we expect that the HH protein represents a new approach to iron and other metal chelation, which may be useful, in addition to its role in iron overload in HH disease, in a variety of other diseases and conditions that are secondary to other disease interventions, including, without limitation, transfusions, thalassaemias, and hemolytic anemias. Delivery of the HH protein or its ligand by either gene therapy or through protein replacement represents a new approach to metal chelation.

Further, because molecules that bind to iron or other metals, we envision that the approach can be utilized for chelation or sequestration of metals, such as copper, lead, zinc, cadmium, or other toxic moieties. Further, since iron is a catalyst for oxidative processes that are known to be deleterious in multiple biological systems, including, without limitation, vascular disease, inflammation, atherosclerosis, lung injury, ischemia, and the like, we envision that the HH protein and/or fragments thereof, including ligands and fragments thereof, can be utilized in anti-oxidative therapies.

An additional aspect of HH disease and iron overload disease is that hepatic iron concentration has been shown to correlate with non-response to α-interferon treatment for chronic hepatitis. See Van Tiel et al. *J Hepatology* 20:410–415 (1994) and Olynyk et al. *Gastroenterology* 108:1104–1109 (1995). Thus, the HH protein and/or fragments or ligands thereto can be utilized in the lowering of hepatic iron levels so as to facilitate increased response to α-interferon in the treatment of these diseases.

1. Pharmacological

In the pharmacological approach, drugs which circumvent or overcome the defective HH gene function are sought. In this approach modulation of HH gene function can be accomplished by agents or drugs which are designed to interact with different aspects of the HH protein structure or function. For example, a drug, antibody or other modulating protein (i.e. β-2-microglobulin or calnexin or similarly acting molecules or parts thereof) could be designed to bind to the HH protein and correct a defective structure.

Alternatively, a drug might bind to a specific functional residue(s) thereby, increasing or decreasing the affinity for ligand, substrate or cofactor.

Efficacy of a drug or agent can be identified in a screening program in which modulation is monitored in in vitro cell systems. Indeed, the present invention provides for host cell systems which express various mutant HH proteins (especially the 24d1 and 24d2 mutations noted in this application) and are suited for use as primary screening systems. Candidate drugs can be evaluated by incubation with these cells and measuring cellular functions dependent on the HH gene or by measuring proper HH protein folding or processing. Such assays might also entail measuring receptor-like activity, iron transport and metabolism, gene transcription or other upstream or downstream biological function as dictated by studies of HH gene function.

Alternatively, cell-free systems can also be utilized. Purified HH protein can be reconstituted into artificial membranes or vesicles and drugs screened in a cell-free system. Such systems are often more convenient and are inherently more amenable to high throughput types of screening and automation.

A variety of drugs and other therapeutic agents have been proposed as useful in the treatment of HH disease and other iron or other metal overload type diseases. See, for example, Great Britain Patent Application No. 2,293,269 A, assigned to Merck Sharp & Dohme Ltd., World Patent Application No. WO 95/16663, assigned to Ciba Geigy AG, German Patent Application No. 4,327,226 A1, assigned to Hoechst AG, World Patent Application No. WO 94/21243, assigned to the University of Nebraska, Canadian Patent Application No. 2,115,224 A, assigned to Bayer Corp., Miles Inc., and others, Canadian Patent Application No. 2,115,222 A, assigned to Bayer Corp., Miles Inc., and others, U.S. Pat. No. 5,385,918 and Canadian Patent Application No. 2,115,221 A, assigned to Bayer Corp., Miles Inc., and others, World Patent Application No. WO 94/11367, assigned to Ciba Geigy AG and the University of Florida, World Patent Application No. WO 94/01463, assigned to the University of *British Columbia*, U.S. Pat. No. 5,256,676, assigned to *British Technology Group Ltd.*, U.S. Pat. No. 5,420,008, assigned to Oriental Yeast Co. Ltd., World Patent Application No. WO 94/04186, U.S. Pat. No. 5,075,469, assigned to Yissum Research and Development Co., European Patent Application No. 346,281, assigned to Ciba Geigy AG, European Patent Application No. 315,434, assigned to Yissum Research and Development Co., U.S. Pat. Nos. 5,424,057, 5,328,992, and 5,185,368, assigned to Ciba Geigy AG, U.S. Pat. Nos. 5,104,865, 4,912,118, 4,863,913, and 4,666,927, assigned to National Research and Development Corp., DD Patent Application No. 208,609, assigned to Akad Wissenschaft, and U.S. Pat. No. 4,434,156, assigned to the Salk Institute for Biological Studies. The invention is useful for the screening of such proposed drugs or other therapeutic agents for specific activity in HH disease models, assays, and design of molecules based thereon.

In vivo testing of HH disease-modifying compounds is also required as a confirmation of activity observed in the in vitro assays. Animal models of HH disease are envisioned and discussed in the section entitled "Animal Models", below, in the present application.

Drugs can be designed to modulate HH gene and HH protein activity from knowledge of the structure and function correlations of HH protein and from knowledge of the specific defect in various HH mutant proteins. For this, rational drug design by use of X-ray crystallography, computer-aided molecular modelling (CAMM), quantitative or qualitative structure-activity relationship (QSAR), and similar technologies can further focus drug discovery efforts. Rational design allows prediction of protein or synthetic structures which can interact with and modify the HH protein activity. Such structures may be synthesized chemically or expressed in biological systems. This approach has been reviewed in Capsey et al., Genetically Engineered Human Therapeutic Drugs, Stockton Press, New York (1988). Further, combinatorial libraries can be designed, synthesized and used in screening programs.

The present invention application also envisions that the treatment of HH disease can take the form of modulation of another protein or step in the pathway in which the HH gene or its protein product participates in order to correct the physiological abnormality. For example, as an MHC-like molecule one could envision that the HH protein acts as a receptor or modulator for iron-binding or iron-regulating molecules. As such intracellular signalling or transport functions could be affected by alterations in HH protein function. Such functions and their effector molecules would also be targets for HH disease-modifying therapies.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

2. Protein Replacement Therapy

The present invention also relates to the use of polypeptide or protein replacement therapy for those individuals determined to have a defective HH gene. Treatment of HH disease could be performed by replacing the defective HH protein with normal protein or its functional equivalent in therapeutic amounts.

HH polypeptide can be prepared for therapy by any of several conventional procedures. First, HH protein can be produced by cloning the HH cDNA into an appropriate expression vector, expressing the HH gene product from this vector in an in vitro expression system (cell-free or cell-based) and isolating the HH protein from the medium or cells of the expression system. General expression vectors and systems are well known in the art. In addition, the invention envisions the potential need to express a stable form of the HH protein in order to obtain high yields and obtain a form readily amenable to intravenous administration. Stable high yield expression of proteins have been achieved through systems utilizing lipid-linked forms of proteins as described in Wettstein et al. *J Exp Med* 174:219–228 (1991) and Lin et al. *Science* 249:677–679 (1990).

HH protein can be prepared synthetically. Alternatively, the HH protein can be prepared from total protein samples by affinity chromatography. Sources would include tissues expressing normal HH protein, in vitro systems (outlined above), or synthetic materials. The affinity matrix would consist of antibodies (polyclonal or monoclonal) coupled to an inert matrix. In addition, various ligands which specifically interact with the HH protein could be immobilized on an inert matrix. For example, β-2-microglobulin or portions thereof, β-2-microglobulin-like molecules, or other specific proteins such as calnexin and calnexin-like molecules or portions thereof. General methods for preparation and use of affinity matrices are well known in the art.

Protein replacement therapy requires that HH protein be administered in an appropriate formulation. The HH protein can be formulated in conventional ways standard to the art for the administration of protein substances. Delivery may require packaging in lipid-containing vesicles (such as Lipofectin™ or other cationic or anionic lipid or certain surfactant proteins) that facilitate incorporation into the cell membrane. The HH protein formulations can be delivered to affected tissues by different methods depending on the affected tissue. For example, iron absorption is initiated in the GI tract. Therefore, delivery by catheter or other means to bypass the stomach would be desirable. In other tissues, IV delivery will be the most direct approach.

3. Gene Therapy

Gene therapy utilizing recombinant DNA technology to deliver the normal form of the HH gene into patient cells or vectors which will supply the patient with gene product in vivo is also contemplated within the scope of the present invention. In gene therapy of HH disease, a normal version of the HH gene is delivered to affected tissue(s) in a form and amount such that the correct gene is expressed and will prepare sufficient quantities of HH protein to reverse the effects of the mutated HH gene. Current approaches to gene therapy include viral vectors, cell-based delivery systems and delivery agents. Further, ex vivo gene therapy could also be useful. In ex vivo gene therapy, cells (either autologous or otherwise) are transfected with the normal HH gene or a portion thereof and implanted or otherwise delivered into the patient. Such cells thereafter express the normal HH gene product in vivo and would be expected to assist a patient with HH disease in avoiding iron overload normally associated with HH disease. Ex vivo gene therapy is described in U.S. Pat. No. 5,399,346 to Anderson et al., the disclosure of which is hereby incorporated by reference in its entirety. Approaches to gene therapy are discussed below:

a. Viral Vectors

Retroviruses are often considered the preferred vector for somatic gene therapy. They provide high efficiency infection, stable integration and stable expression (Friedman. T. Progress Toward Human Gene Therapy. Science 244:1275 (1989)). The full length HH gene cDNA can be cloned into a retroviral vector driven by its endogenous promoter or from the retroviral LTR. Delivery of the virus could be accomplished by direct implantation of virus directly into the affected tissue.

Other delivery systems which can be utilized include adenovirus, adeno-associated virus (AAV), vaccinia virus, bovine papilloma virus or members of the herpes virus group such as Epstein-Barr virus. Viruses with tropism to the gut and viruses engineered with tissue specific promoters are also envisioned. Viruses can be, and preferably are, replication deficient.

b. Cell-based Delivery

Much work has been performed in recent years regarding producing transgenic cells possessing therapeutic genes. Such cells could be directly implanted or implanted within a membrane-based matrix. For these purposes, many cells types would suffice but cells particularly derived from the target organs such as gut or liver are particularly useful. Examples include fetal liver or fetal gut epithelial cells.

c. Non-viral Gene Transfer

Other methods of inserting the HH gene into the appropriate tissues may also be productive. Many of these agents, however, are of lower efficiency than viral vectors and would potentially require infection in vitro, selection of transfectants, and reimplantation. This would include calcium phosphate, DEAE dextran, electroporation, and protoplast fusion. A particularly attractive idea is the use of liposomes (i.e., LIPOFECTIN™), which might be possible to carry out in vivo. Synthetic cationic lipids and DNA conjugates also appear to show some promise and may increase the efficiency and ease of carrying out this approach.

4. Animal Models

The generation of a mouse or other animal model of HH disease is important for both an understanding the biology of the disease but also for testing of potential therapies. Currently only a single animal model of HH disease exists. As was demonstrated by de Sousa et al. *Immun Lett* 39:105–111 (1994), and later by Rothenberg and Voland supra (1996), it is possible to develop a model of HH disease by interfering with the normal expression of β-2-microglobulin. β-2-microglobulin is necessary for the proper folding and surface presentation of MHC class I molecules. Mice with a disrupted β-2-microglobulin gene were created that do not express β-2-microglobulin protein on the surface of most cells. Mice with this mutation possess almost no CD8+ cytotoxic T lymphocytes and develop progressive hepatic iron overload similar to HH disease. This model is somewhat limited in its representation of HH disease in humans as β-2-microglobulin serves as a chaperone-like molecule for most, if not all, MHC Class I molecules, thereby affecting more biological systems than just those anticipated to be affected by disruption of the HH gene. Moreover, we have demonstrated that β-2-microglobulin is not mutated in HH affected individuals. Thus, the β-2-microglobulin knock-out mouse is not the best animal model to represent the human disease.

The present invention envisions the creation of a more specific animal model of HH disease by inactivation of the homologous HH gene or by introduction of the HH disease causing mutations in a number of species including mice, rats, pigs, and primates. These models will be novel in that targeting the homologous HH gene alone will more specifically represent the disease as described in humans.

Techniques for specifically inactivating or mutating genes by homologous recombination in embryonic stem cells (ES cells) have been described (Capecci Science 244:1288 (1989)). Animals with the inactivated homologous HH gene can then be used to introduce the mutant or normal human HH gene or for introduction of the homologous gene to that species and containing the 24d1, 24d2, or other HH disease-causing mutations. Methods for these transgenic procedures are well known to those versed in the art and have been described by Murphy and Carter, *Curr. Opin. Cell. Biol.* 4:273–279 (1992).

5. Down Regulation of the HH Gene or HH Gene Product

In certain therapeutic applications, it is desirable to down regulate the expression and/or function of the HH gene, the mutant HH gene, the HH protein, or the mutant HH protein. For example, down regulation of the normal HH gene or the normal HH protein is desirable in situations where iron is underaccumulated in the body, for example in certain anemias (i.e., thalassaemias, hemolytic anemias, transfusions). On the other hand, down regulation of the mutant HH gene or the HH protein is desirable in situations where iron is overaccumulated in the body.

As discussed above in the Section entitled "Antibodies," antibodies specific to the normal or the mutant HH protein can be prepared. Such antibodies can be used therapeutically in HH disease. For example, to block the action of the mutant or normal HH gene if the function associated with the mutant protein is an upregulation of the normal HH protein function and leads to an overaccumulation of iron in the body, as mentioned above. Similarly, antibodies can be used therapeutically to block action of an HH protein that is causing an underaccumulation of iron in the body.

In a similar manner, the HH gene, either in normal or in a mutant form, can be downregulated through the use of antisense oligonucleotides directed against the gene or its transcripts. A similar strategy can be utilized as discussed above in connection with antibodies. For a particularly valuable review of the design considerations and use of antisense oligonucleotides, see Uhlmann et al. *Chemical Reviews* 90:543–584 (1990) the disclosure of which is hereby incorporated by reference. The antisense oligonucleotides of the present invention may be synthesized by any of the known chemical oligonucleotide synthesis methods. Such methods are generally described, for example, in Winnacker *Chirurg* 63:145–149 (1992). Antisense oligonucleotides are most advantageously prepared by utilizing any of the commercially available, automated nucleic acid synthesizers. One such device, the Applied Biosystems 380B DNA Synthesizer, utilizes β-cyanoethyl phosphoramidite chemistry.

Since the complete nucleotide synthesis of DNA complementary to the HH gene and the mutant HH genes' mRNA transcript is known, antisense oligonucleotides hybridizable with any portion of such transcripts may be prepared by oligonucleotide synthesis methods known to those skilled in the art. While any length oligonucleotide may be utilized in the practice of the invention, sequences shorter than 12 bases may be less specific in hybridizing to the target mRNA, may be more easily destroyed by enzymatic digestion, and may be destabilized by enzymatic digestion. Hence, oligonucleotides having 12 or more nucleotides are preferred. Long sequences, particularly sequences longer than about 40 nucleotides, may be somewhat less effective in inhibiting translation because of decreased uptake by the target cell. Thus, oligomers of 12–40 nucleotides are preferred, more preferably 15–30 nucleotides, most preferably 18–26 nucleotides. Sequences of 18–24 nucleotides are most particularly preferred.

ILLUSTRATIVE EXAMPLES

The following examples are provided to illustrate certain aspects of the present invention and not intended as limiting the subject matter thereof:

EXAMPLE 1

HH Diagnostic: OLA Assay

As discussed above, the oligonucleotide ligation assay (OLA) (Nickerson, D. A. et al. *Proc Natl Acad Sci USA* 87:8923–8927 (1990)) is highly effective for detecting single nucleotide changes in DNA and RNA, such as the 24d1, 24d2, and 24d7 mutations or sequence variations. Thus, in accordance with the present invention, there is provided an assay kit to detect mutations in the HH gene through use of an OLA assay.

In the OLA assay, a sample of DNA or cDNA reverse transcribed from RNA is amplified, generally through use of polymerase chain reaction (PCR) amplification, followed by ligation with upstream and downstream oligonucleotides specific to either side of the mutation sought to be assayed. Either the upstream or the downstream oligonucleotide includes a base complementary to the mutated or normal allele and the upstream or downstream oligonucleotide is labeled to enable detection of hybridization to the variant base.

Oligonucleotides complementary to the upstream or downstream sequence of the DNA or RNA in the sample, plus the mutated or normal allele, are ordinarily utilized in parallel so that detection of heterozygosity and homozygosity is possible.

Generally, the kit includes reaction chambers in which to conduct amplification of DNA or reverse transcribed RNA from patient samples, ligation reactions, and detection of ligation products. One exemplary reaction chamber that can be utilized to conduct such steps is a microtiter plate. The kit can be provided with or without reagents and oligonucleotides for use in the assay. In general, however, in a preferred embodiment, the kit is provided with oligonucleotides for amplifying at least a portion of a patient's DNA or RNA across the mutation that is to be detected. As will be appreciated, oligonucleotide primers can be designed to virtually any portion of the DNA or transcription products flanking the nucleotide sought to be assayed, up to and including, and in some cases even exceeding 500 bases away from the mutation to be assayed. Further, ligation oligonucleotides can be designed in a variety of lengths.

Samples (either DNA or reverse transcribed RNA) are placed into the reaction vessel(s) with appropriate primers, nucleotides, buffers, and salts and subjected to PCR amplification. The PCR products are then assayed for single base mutations using OLA.

Suitable genomic DNA-containing samples from patients can be readily obtained and the DNA extracted therefrom using conventional techniques. For example, DNA can be isolated and prepared in accordance with the method described in Dracopoli, N. et al. eds. *Current Protocols in Human Genetics* pp. 7.1.1–7.1.7 (J. Wiley & Sons, New York (1994)), the disclosure of which is hereby incorporated by reference in its entirety. Most typically, a blood sample, a buccal swab, a hair follicle preparation, or a nasal aspirate is used as a source of cells to provide the DNA.

Alternatively, RNA from an individual (i.e., freshly transcribed or messenger RNA) can be easily utilized in accordance with the present invention for the detection of the selected base mutation. Total RNA from an individual can be isolated according to the procedure outlined in Sambrook, J. et al. *Molecular Cloning—A Laboratory Manual* pp. 7.3–7.76 (2nd Ed., Cold Spring Harbor Laboratory Press, New York (1989)) the disclosure of which is hereby incorporated by reference.

When using either DNA or RNA samples for the detection of base mutations in an OLA assay, the patient DNA or reverse transcribed RNA is first amplified, followed by assaying for ligation. In a preferred embodiment, the amplification primers for detecting the 24d1 mutation in DNA are shown in FIG. 5 and labeled 24d1.P1 (SEQ ID NO:13) and 24d1.P2 (SEQ ID NO:14), designed as shown in FIG. 6. Also on FIG. 5, the oligonucleotides used in the sequence determination by OLA for 24d1 are designated 24d1.A (SEQ ID NO:15), 24d1.B (SEQ ID NO:16), and 24d1. X (SEQ ID NO:17). As indicated in the sequences shown, "bio" indicates biotin coupling, "p" indicates 5'-phosphate, and "dig" indicates coupled digoxigenin. It will be appreciated that the binding of biotin and digoxigenin can be reversed. In other words, digoxigenin can be bound to the 5' end of oligonucleotides 24d1.A and 24d1.B and biotin can be bound to the 3' end of the 24d1.X oligonucleotide.

The use of RNA, as opposed to DNA, follows essentially an identical approach: the RNA is isolated and after reverse transcription the characteristic base mutation can be detected as described above. In order to perform PCR amplification of the RNA prior to OLA assay, the following oligonucleotide primers are preferably utilized:

```
Forward Primer
    24d1.P3    CTG AAA GGG TGG GAT CAC AT    (SEQ ID NO:18)

Reverse Primer
    24d1.P4    CAA GGA GTT CGT CAG GCA AT    (SEQ ID NO:19)
```

In amplification, a solution containing the DNA sample (obtained either directly or through reverse transcription of RNA) is mixed with an aliquot of each of dATP, dCTP, dGTP and dTTP (i.e., Pharmacia LKB Biotechnology, NJ), an aliquot of each of the DNA specific PCR primers, an aliquot of Taq polymerase (i.e., Promega, Wis.), and an aliquot of PCR buffer, including $MgCl_2$ (i.e., Promega) to a final volume. Followed by pre-denaturation (i.e., at 95° C. for 7 minutes), PCR is carried out in a DNA thermal cycler (i.e., Perkin-Elmer Cetus, Conn.) with repetitive cycles of annealing, extension, and denaturation. As will be appreciated, such steps can be modified to optimize the PCR amplification for any particular reaction, however, exemplary conditions utilized include denaturation at 95° C. for 1 minute, annealing at 55° C. for 1 minute, and extension at 72° C. for 4 minutes, respectively, for 30 cycles. Further details of the PCR technique can be found in Erlich, "PCR Technology," Stockton Press (1989) and U.S. Pat. No. 4,683,202, the disclosure of which is incorporated herein by reference.

Following PCR amplification, the PCR products are subjected to a ligation assay. Generally, ligation of the oligonucleotides requires a 5'-phosphate and a 3'-OH held in proximity by annealing to a complementary DNA strand (i.e., the PCR product), ligation buffer, and DNA ligase. A phosphodiester bond is formed through the reaction. If, however, there is a sequence dissimilarity at the point of ligation, ligation will not be accomplished and no phosphodiester bond will be formed.

In a preferred assay, two ligation oligonucleotides are utilized (i.e., such as the ligation oligonucleotides mentioned above for the detection of the 24d1 mutation (SEQ ID NO:15 and SEQ ID NO:17 for detection of the G allele or SEQ ID NO:16 and SEQ ID NO:17 for detection of the A allele)). The PCR products and the ligation oligonucleotides are suspended in ligation buffer, including NAD, with a DNA ligase, preferably amp-ligase (Epicentre) which is a thermal ligase. Ten cycles of ligation are performed at 94° C. for 20 seconds and 58° C. for 2 minutes in a thermal cycler. The reaction is stopped with EDTA and the product is transferred to streptavidin coated plates and incubated for 45 minutes. Thereafter the wells are alkaline washed to denature the oligonucleotides from the initial PCR products and then washed with TRIS buffer to remove any unbound materials (i.e., all products other than the biotinylated products which bind to the streptavidin on the plates).

Detection is accomplished, preferably, through use of an anti-digoxigenin antibody conjugated with alkaline phosphatase (Boehringer-Mannheim) which is added and incubated at 37° C. for 30 minutes. The plates are washed with TRIS buffer to remove any unbound antibody. An ELISA detection kit (Life Technologies) is utilized where NADPH is used as a substrate where the alkaline phosphatase conjugated to the antibody cleaves NADPH to NADH. The NADH produced by this reaction is used as a cofactor for diaphorase to turn INF-violet to Formazan which generates a red color. Presence of the red color provides a positive signal that ligation occurred and lack of the red color indicates that ligation did not occur, which indicates the presence or absence of the specific base being assayed.

As will be appreciated, the OLA assay allows the differentiation between individuals who are homozygous versus heterozygous for particular mutations (such as the 24d1 mutation, for which the ligation oligonucleotides mentioned above are designed, or the 24d2 mutation). This feature allows one to rapidly and easily determine whether an individual is at a significant risk of developing HH. Oligonucleotides useful for amplifying and detecting the 24d2 mutant and normal alleles are provided in FIG. 9.

In the OLA assay, when carried out in microtiter plates, for example, one well is used for the determination of the presence of the normal allele (i.e., the 24d1:G allele) and a second well is used for the determination of the presence of the mutated allele (i.e., the 24d1:A allele). Thus, the results for an individual who is heterozygous for the 24d1 mutation will show a signal in each of the A and G wells and an individual who is homozygous for the 24d1:A allele will show a signal in only the A well. Those individuals who are homozygous for the A allele at 24d1 are, as discussed above, homozygous for the common ancestral HH-mutation and are at a significant risk of developing HH disease.

In particular, therefore, a kit for detecting the 24d1 mutation by OLA assay is provided. In the kit, amplification primers for DNA or RNA (or generally primers for amplifying a sequence of genomic DNA, reverse transcription products, complementary products) including the 24d1 mutated and normal alleles are provided. Ligation assay oligonucleotides are also preferably provided. The kit further includes separate reaction wells and reagents for detecting the presence of homozygosity or heterozygosity for the 24d1 mutation.

Within the same kit, or in separate kits, oligonucleotides for amplification and detection of other differences (such as the 24d2 mutation and/or the 24d7 sequence variant) can also be provided. If in the same kit as that used for detection of the 24d1 mutation, separate wells and reagents are provided, and homozygosity and heterozygosity can similarly be determined.

Because of the enrichment of the 24d2 mutation in individuals who are heterozygous for the 24d1 mutation, kits are specifically envisioned in accordance with the invention which screen for the presence of the 24d2 mutation when 24d1 heterozygosity is detected.

EXAMPLE 2

HH Diagnostic: Other Nucleotide Based Assays

As will be appreciated, a variety of other nucleotide based detection techniques are available for the detection of mutations in samples of RNA or DNA from patients. See, for example, Section (III)(A)(2), above, entitled "Nucleic Acid Based Screening." Any one or any combination of such techniques can be used in accordance with the invention for the design of a diagnostic device and method for the screening of samples of DNA or RNA for HH gene mutations in accordance with the invention, such as the mutations and sequence variants identified herein (24d1, 24d2, and 24d7). Further, other techniques, currently available, or developed in the future, which allow for the specific detection of mutations and sequence variants in the HH gene are contemplated in accordance with the invention.

Through use of any such techniques, it will be appreciated that devices and methods can be readily developed by those of ordinary skill in art to rapidly and accurately screen for mutations and sequence variants in the HH gene in accordance with the invention.

Thus, in accordance with the invention, there is provided a nucleic acid based test for HH gene mutations and sequence variants which comprises providing a sample of a patient's DNA or RNA and assessing the DNA or RNA for the presence of one or more HH gene mutations or sequence variants. Samples of patient DNA or RNA (or genomic, transcribed, reverse transcribed, and/or complementary sequences to the HH gene) can be readily obtained as described in Example 1. Through the identification and characterization of the HH gene as taught and disclosed in the present invention, one of ordinary skill in the art can readily identify the genomic, transcribed, reverse transcribed, and/or complementary sequences to the HH gene sequence in a sample and readily detect differences therein. Such differences in accordance with the present invention can be the 24d1, 24d2, and/or 24d7 mutations or sequence variations identified and characterized in accordance herewith. Alternatively, other differences might similarly be detectable.

Kits for conducting and/or substantially automating the process of identification and detection of selected changes, as well as reagents utilized in connection therewith, are therefore envisioned in accordance with the invention of the present invention.

EXAMPLE 3

HH Diagnostic: Antibody Based Assay

As discussed in Section (III)(A)(3), herein, entitled "Antibodies," antibodies specific to both the normal/wild-type or mutated gene products of the HH gene can be readily prepared. Thus, in accordance with the invention a kit for the detection of an HH gene product, and particularly, the mutated HH gene product is provided for use in a diagnostic test for the presence of HH disease.

Antibody based tests are well known in the art. In general, a sample of tissue, cells, or bodily fluid is obtained, or provided, from a patient. If the sample contains cells or tissues, typically the sample is disrupted to free the HH gene product. Alternatively, if surface expression exists, whole cells can be utilized. Thereafter, the sample is contacted with an antibody specific to the selected HH gene product and binding of the antibody, if any, is detected. Typically, the antibody is bound to, either directly, or through another moiety (i.e., biotin), a label to facilitate detection of hybridization. Such label can be radioactive, fluorescent, a dye, a stain, or the like.

Thus, antibodies for diagnostic applications, and diagnostic kits including antibodies (and/or other reagents utilized in connection therewith) are provided in accordance with the invention.

EXAMPLE 4

HH Therapy: In Vivo Gene Therapy

The discovery of the HH gene in accordance with the invention also provides a therapeutic for HH disease in the form of gene therapy. In the present example, gene therapy is accomplished in vivo. In in vivo gene therapy, a patient is treated with a gene product in a form that is designed to cause the patient to express the gene.

The coding region of the HH gene, or parts or portions thereof, can be incorporated into a suitable vector for use in the treatment of HH disease. Indeed, the coding region of the HH gene is of a manageable size for incorporation in a viral vector, such as a retroviral or adenoviral vectors. Generally, the vector will be construct to include suitable promoters, enhancers, and the like. Additional information related to the design of HH gene construct for use in gene therapy is provided in Section (III)(B)(1), entitled "Expression Systems."

Viral vector systems have been indicated as highly efficient in transferring genes to mammals containing deficient genes. See, for example, Crystal *Am. J. Med.* 92(6A): 44S–52S (1992); Lemarchand et al. *Proc. Nat'l Acad. Sci. USA* 89(14):6482–6486 (1992) the disclosures of which are hereby incorporated by reference.

The viral vector can also be conveniently administered to a patient. For example, administration may be accomplished through, for example, liquid lavage, direct injection, or through ex vivo treatment of cells, followed by reinfusion of such cells into the patient. Particularly preferred tissues for delivery of vectors including the HH gene are the liver and the gut. It will be appreciated that liquid lavage or direct injection can be utilized for delivery of the vector to the gut, while direct injection will presumably be necessary for delivery to the liver.

EXAMPLE 5

HH Therapy: Protein Replacement Therapy

As discussed above, also provided in accordance with the invention is a therapy for HH disease involving replacement of the IH protein product. Where a patient is diagnosed as having HH disease and is not producing, or is underproducing, the normal HH gene product, such patient can be treated by replacing the normal HH gene product to assist the patient's body in combating HH disease.

The HH gene product can be produced through the methods discussed above in connection with the Section entitled "Protein Purification" above.

Delivery of the HH gene product can be accomplished as discussed in connection with Section entitled "Therapeutics" above.

EXAMPLE 6

HH Therapy: Drug Design and Screening

As discussed above in connection with the Section entitled "Pharmacological," the HH gene and parts and portions thereof can be utilized for drug screening. Cell-based and cell-free assays are envisioned in accordance with the invention. As discussed above, a variety of drugs and other therapeutics have been proposed to have activity in HH disease. Compounds such as those described can be assayed in cellular systems containing the HH gene or the mutations therein. Cellular functions such as HH protein folding, iron uptake, transport, metabolism, receptor-like activities, other upstream or downstream processes, such as gene transcription and other signaling events, and the like can be assayed. Each of these functions can be analyzed using conventional techniques that are well known in the art.

It is expected that through use of such assays, compounds can be rapidly screened for potential activity in HH disease and compounds showing high activity can be used for the construction of combinatorial libraries. Candidates from the combinatorial libraries can be re-assayed and those with better activity than the parent compound can be analyzed for clinical development.

EXAMPLE 7

HH Study: Animal Models of HH Disease

As discussed above, through knowledge of the gene-associated mutations responsible for HH disease, it is now possible to prepare transgenic animals as models of the HH disease. Such animals are useful in both understanding the mechanisms of HH disease as well as use in drug discovery efforts. The animals can be used in combination with cell-based or cell-free assays for drug screening programs.

In preparation of transgenic animals in accordance with the invention, genes within embryonic stem cells (ES cells) can be inactivated by homologous recombination. See Capecci supra. (1989). Specifically, an isogenic mouse genomic library (i.e., an Sv-129 library) can be screened with a human HH gene cDNA probe. The resultant clones from the library are then sequenced to ensure sequence identity to the mouse HH gene homologous cDNA. A targeting vector is then constructed from the mouse genomic DNA consisting of two approximately 3 kb genomic fragments from the mouse HH gene as 5' and 3' homologous arms. These arms would be chosen to flank a region critical to the function of the HH gene product, such as exon 4 (the immunoglobulin-like region which contains the proposed critical β-2-microglobulin interactive domain and essential disulfide linkage). However, other regions could also be targeted.

In place of exon 4, negative and positive selectable markers can be placed, for example, to abolish the activity of the HH gene. As a positive selectable marker a neo gene under control of phosphoglycerate kinase (pgk-1) promoter may be used and as a negative selectable marker the 5' arm of the vector can be flanked by a pgk-1 promoted herpes simplex thymidine kinase (HSV-TK) gene can be used.

The vector is then transfected into R1 ES cells and the transfectants are subjected to positive and negative selection (i.e., G418 and gancyclovir, respectively, where neo and HSV-TK are used). PCR is then used to screen for surviving colonies for the desired homologous recombination events. These are confirmed by Southern blot analysis.

Subsequently, several mutant clones are picked and injected into C57BL/6 blastocytes to produce high-percentage chimeric animals. The animals are then mated to C57BL/6 females. Heterozygous offspring are then mated to produce homozygous mutants. Such mutant offspring can then be tested for the HH gene mutation by Southern blot analysis. In addition, these animals are tested by RT-PCR to assess whether the targeted homologous recombination results in the ablation of the HH gene mRNA. These results are confirmed by Northern blot analysis and RNase protection assays.

Once established, the HH gene −/− mice can be studied for the development of HH-like disease and can also be utilized to examine which cells and tissue-types are involved in the HH disease process. The animals can also be used to introduce the mutant or normal HH gene or for the introduction of the homologous gene to that species (i.e., mouse) and containing the 24d1, 24d2, or other disease causing mutations. Methods for the above-described transgenic procedures are well known to those versed in the art and are described in detail by Murphy and Carter supra (1993).

The techniques described above, can also be used to introduce the 24d1 or 24d2 mutations, or other homologous mutations in the animal, into the homologous animal gene. As will be appreciated, similar techniques to those described above, can be utilized for the creation of many transgenic animal lines, i.e., pig, sheep, goat, ape, orangutan, primate, or the like, and mice are only demonstrative.

INCORPORATION BY REFERENCE

To the extent that any reference (including books, articles, papers, patents, and patent applications) cited herein is not already incorporated by reference, they are hereby expressly incorporated by reference in their entirety.

EQUIVALENTS

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. An isolated nucleic acid up to 11 kb in length comprising a nucleic acid sequence selected from the group consisting of:
   (a) nucleic acid sequences having SEQ ID NO:1;
   (b) nucleic acid sequences having SEQ ID NO:3; SEQ ID NO:5, or SEQ ID NO:7;
   (c) nucleic acid sequences having SEQ ID NO:9; and
   (d) nucleic acid sequences having SEQ ID NO:10, SEQ ID NO:11, or SEQ ID NO:12.

2. The isolated nucleic acid of claim 1, wherein said nucleic acid is cDNA.

3. The nucleic acid of claim 1, wherein the nucleic acid is a nucleic acid sequence having SEQ ID NO:1.

4. The nucleic acid sequence of claim 1, wherein the nucleic acid is a nucleic acid sequence selected from the group consisting of SEQ ID NO:3, SEQ ID NO:5, and SEQ ID NO:7.

5. The nucleic acid sequence of claim 1, wherein the nucleic acid is a nucleic acid sequence selected from the group consisting of SEQ ID NO:10, SEQ ID NO:11, and SEQ ID NO:12.

6. A method for diagnosing a patient as having an increased risk of developing HH disease, comprising:
   providing DNA or RNA from the individual; and
   assessing the DNA or RNA for the presence or absence of an HH-associated allele A having a base mutation designated herein 24d1 (A) in combination with assessing the DNA or RNA for the HH-associated allele G having a base mutation designated herein 24d2 (G),
   wherein, as a result, the absence of the alleles indicates the absence of the HH gene mutation in the genome of the individual and the presence of the alleles indicates the presence of the HH gene mutation in the genome of the individual and an increase risk of developing HH disease.

7. The method of claim 6, wherein the assessing step is performed by a process which comprises subjecting the DNA or RNA to amplification using oligonucleotide primers flanking the base-pair mutation 24d1 (A).

8. The method of claim 7, wherein the assessing step further comprises an oligonucleotide ligation assay.

9. The method of claim 8, wherein the assessing step further comprises providing a housing having a first well that is adapted for conducting an oligonucleotide ligation assay and providing a signal when 24d1A is present in the DNA or RNA and a second well that is adapted for conducting an oligonucleotide ligation assay and providing a signal when 24d1G is present in the DNA or RNA.

10. The method of claim 9, wherein the assessing step further comprises determining whether the individual is homozygous or heterozygous for 24d1A, wherein when the individual is heterozygous for 24d1A a signal will be observed in both the first and second wells upon conducting the oligonucleotide ligation assay and when the individual is homozygous for 24d1A a signal will be observed in the first well upon conducting the oligonucleotide ligation assay.

11. The method of claim 7, wherein DNA is amplified with oligonucleotide primers of SEQ ID NO:13 and SEQ ID NO:14.

12. The method of claim 11, wherein the assessing step further comprises an oligonucleotide ligation assay.

13. The method of claim 12, wherein the oligonucleotide ligation assay is accomplished using oligonucleotides of SEQ ID NO:15, SEQ ID NO:16, and SEQ ID NO:17.

14. The method of claim 7, wherein RNA is amplified with oligonucleotide primers of SEQ ID NO:18 and SEQ ID NO:19.

15. The method of claim 14, wherein the assessing step further comprises an oligonucleotide ligation assay.

16. The method of claim 15, wherein the oligonucleotide ligation assay is accomplished using oligonucleotides of SEQ ID NO:15, SEQ ID NO:16, and SEQ ID NO:17.

17. The method of claim 6, wherein the assessing step is performed by a process which comprises subjecting the DNA or RNA to amplification using oligonucleotide primers flanking 24d2 (G).

18. The method of claim 17, wherein the assessing step further comprises an oligonucleotide ligation assay.

19. The method of claim 18, wherein the assessing step further comprises providing a housing having a first well that is adapted for conducting an oligonucleotide ligation assay and providing a signal when 24d2 (G) is present in the DNA or RNA and a second well that is adapted for conducting an oligonucleotide ligation assay and providing a signal when 24d2 (C) is present in the DNA or RNA.

20. The method of claim 19, wherein the assessing step further comprises detecting whether the DNA or RNA is homozygous or heterozygous for 24d2 (G), wherein when the DNA or RNA is heterozygous for 24d2 (G) a signal will be observed in both the first and second wells upon conducting the oligonucleotide ligation assay and when the DNA or RNA is homozygous for 24d2 (G) a signal will be observed in the first well upon conducting the oligonucleotide ligation assay.

21. The method of claim 17, wherein DNA is amplified with oligonucleotide primers of SEQ ID NO:24 and SEQ ID NO:25.

22. The method of claim 21, wherein the assessing step further comprises an oligonucleotide ligation assay.

23. The method of claim 22, wherein the oligonucleotide ligation assay is accomplished using oligonucleotides of SEQ ID NO:26, SEQ ID NO:27, and SEQ ID NO:28.

24. An oligonucleotide of at least 8 consecutive nucleotides selected from a sequence unique to SEQ ID NO:1, 3, 5, or 7 or the complement of SEQ ID NO:1, 3, 5, or 7.

25. The oligonucleotide of claim 24, wherein the oligonucleotide is a member of an oligonucleotide pair for amplification of an HH nucleic acid sequence.

26. An oligonucleotide of at least 9 consecutive nucleotides selected from a sequence unique to SEQ ID NO:1, 3, 5, or 7 or the complement of SEQ ID NO:1, 3, 5, or 7.

27. The oligonucleotide of claim 26, wherein the oligonucleotide is a member of an oligonucleotide pair for amplification of an HH nucleic acid sequence.

28. An oligonucleotide of at least 10 consecutive nucleotides selected from a sequence unique to SEQ ID NO:1, 3, 5, or 7.

29. The oligonucleotide of claim 28, wherein the oligonucleotide is a member of an oligonucleotide pair for amplification of an HH nucleic acid sequence.

30. An oligonucleotide of at least 11 consecutive nucleotides selected from a sequence unique to SEQ ID NO:1, 3, 5, or 7 or the complement of SEQ ID NO:1, 3, 5, or 7.

31. The oligonucleotide of claim 30, wherein the oligonucleotide is a member of an oligonucleotide pair for amplification of an HH nucleic acid sequence.

32. An oligonucleotide of at least 12 consecutive nucleotides selected from a sequence unique to SEQ ID NO:1, 3, 5, or 7 or the complement of SEQ ID NO:1, 3, 5, or 7.

33. The oligonucleotide of claim 32, wherein the oligonucleotide is a member of an oligonucleotide pair for amplification of an HH nucleic acid sequence.

34. An oligonucleotide of at least 13 consecutive nucleotides selected from a sequence unique to SEQ ID NO:1, 3, 5, or 7 or the complement of SEQ ID NO:1, 3, 5, or 7.

35. The oligonucleotide of claim 34, wherein the oligonucleotide is a member of an oligonucleotide pair for amplification of an HH nucleic acid sequence.

36. An oligonucleotide of at least 14 consecutive nucleotides selected from a sequence unique to SEQ ID NO:1, 3, 5, or 7 or the complement of SEQ ID NO:1, 3, 5, or 7.

37. The oligonucleotide of claim 36, wherein the oligonucleotide is a member of an oligonucleotide pair for amplification of an HH nucleic acid sequence.

38. An oligonucleotide of at least 15 consecutive nucleotides selected from a sequence unique to SEQ ID NO:1, 3, 5, or 7 or the complement of SEQ ID NO:1, 3, 5, or 7.

39. The oligonucleotide of claim 38, wherein the oligonucleotide is a member of an oligonucleotide pair for amplification of an HH nucleic acid sequence.

40. An oligonucleotide of at least 16 consecutive nucleotides selected from a sequence unique to SEQ ID NO:1, 3, 5, or 7 or the complement of SEQ ID NO:1, 3, 5, or 7.

41. The oligonucleotide of claim 40, wherein the oligonucleotide is a member of an oligonucleotide pair for amplification of an HH nucleic acid sequence.

42. An oligonucleotide of at least 17 consecutive nucleotides selected from a sequence unique to SEQ ID NO:1, 3, 5, or 7 or the complement of SEQ ID NO:1, 3, 5, or 7.

43. The oligonucleotide of claim 42, wherein the oligonucleotide is a member of an oligonucleotide pair for amplification of an HH nucleic acid sequence.

44. An oligonucleotide of at least 18 consecutive nucleotides selected from a sequence unique to SEQ ID NO:1, 3, 5, or 7 or the complement of SEQ ID NO:1, 3, 5, or 7.

45. The oligonucleotide of claim 44, wherein the oligonucleotide is a member of an oligonucleotide pair for amplification of an HH nucleic acid sequence.

46. An oligonucleotide of at least 8 consecutive nucleotides selected from a sequence unique to SEQ ID NO:9, 10, 11 or 12 or the complement of SEQ ID NO:9, 10, 11, or 12.

47. The oligonucleotide of claim 46, wherein the oligonucleotide is a member of an oligonucleotide pair for amplification of an HH nucleic acid sequence.

48. An oligonucleotide of at least 9 consecutive nucleotides selected from a sequence unique to SEQ ID NO:9, 10, 11 or 12 or the complement of SEQ ID NO:9, 10, 11, or 12.

49. The oligonucleotide of claim 48, wherein the oligonucleotide is a member of an oligonucleotide pair for amplification of an HH nucleic acid sequence.

50. An oligonucleotide of at least 10 consecutive nucleotides selected from a sequence unique to SEQ ID NO:9, 10, 11 or 12 or the complement of SEQ ID NO:9, 10, 11, or 12.

51. The oligonucleotide of claim 50, wherein the oligonucleotide is a member of an oligonucleotide pair for amplification of an HH nucleic acid sequence.

52. An oligonucleotide of at least 11 consecutive nucleotides selected from a sequence unique to SEQ ID NO:9, 10, 11 or 12 or the complement of SEQ ID NO:9, 10, 11, or 12.

53. The oligonucleotide of claim 52, wherein the oligonucleotide is a member of an oligonucleotide pair for amplification of an HH nucleic acid sequence.

54. An oligonucleotide of at least 12 consecutive nucleotides selected from a sequence unique to SEQ ID NO:9, 10, 11 or 12 or the complement of SEQ ID NO:9, 10, 11, or 12.

55. The oligonucleotide of claim 54, wherein the oligonucleotide is a member of an oligonucleotide pair for amplification of an HH nucleic acid sequence.

56. An oligonucleotide of at least 13 consecutive nucleotides selected from a sequence unique to SEQ ID NO:9, 10, 11 or 12 or the complement of SEQ ID NO:9, 10, 11, or 12.

57. The oligonucleotide of claim 56, wherein the oligonucleotide is a member of an oligonucleotide pair for amplification of an HH nucleic acid sequence.

58. An oligonucleotide of at least 14 consecutive nucleotides selected from a sequence unique to SEQ ID NO:9, 10, 11 or 12 or the complement of SEQ ID NO:9, 10, 11, or 12.

59. The oligonucleotide of claim 58, wherein the oligonucleotide is a member of an oligonucleotide pair for amplification of an HH nucleic acid sequence.

60. An oligonucleotide of at least 15 consecutive nucleotides selected from a sequence unique to SEQ ID NO:9, 10, 11 or 12 or the complement of SEQ ID NO:9, 10, 11, or 12.

61. The oligonucleotide of claim 60, wherein the oligonucleotide is a member of an oligonucleotide pair for amplification of an HH nucleic acid sequence.

62. An oligonucleotide of at least 16 consecutive nucleotides selected from a sequence unique to SEQ ID NO:9, 10, 11 or 12 or the complement of SEQ ID NO:9, 10, 11, or 12.

63. The oligonucleotide of claim 62, wherein the oligonucleotide is a member of an oligonucleotide pair for amplification of an HH nucleic acid sequence.

64. An oligonucleotide of at least 17 consecutive nucleotides selected from a sequence unique to SEQ ID NO:9, 10, 11 or 12 or the complement of SEQ ID NO:9, 10, 11, or 12.

65. The oligonucleotide of claim 64, wherein the oligonucleotide is a member of an oligonucleotide pair for amplification of an HH nucleic acid sequence.

66. An oligonucleotide of at least 18 consecutive nucleotides selected from a sequence unique to SEQ ID NO:9, 10, 11 or 12 or the complement of SEQ ID NO:9, 10, 11, or 12.

67. The oligonucleotide of claim 66, wherein the oligonucleotide is a member of an oligonucleotide pair for amplification of an HH nucleic acid sequence.

* * * * *